US 8,207,300 B2

United States Patent
Parmigiani et al.

(10) Patent No.: US 8,207,300 B2
(45) Date of Patent: Jun. 26, 2012

(54) CTSP CANCER-TESTIS ANTIGENS

(75) Inventors: Raphael Bessa Parmigiani, Sao Paulo (BR); Maria Dulcetti Vibranovski, Sao Paulo (BR); Sandro Jose de Souza, Sao Paulo (BR); Anamaria Aranha Camargo, Sao Paulo (BR)

(73) Assignee: Ludwig Institute for Cancer Research Ltd., New York, NY (US)

( * ) Notice: Subject to any disclaimer, the term of this patent is extended or adjusted under 35 U.S.C. 154(b) by 560 days.

(21) Appl. No.: 12/087,954

(22) PCT Filed: Jan. 29, 2007

(86) PCT No.: PCT/US2007/002486
§ 371 (c)(1),
(2), (4) Date: Oct. 24, 2008

(87) PCT Pub. No.: WO2007/123591
PCT Pub. Date: Nov. 1, 2007

(65) Prior Publication Data
US 2009/0181021 A1    Jul. 16, 2009

Related U.S. Application Data

(60) Provisional application No. 60/763,345, filed on Jan. 30, 2006.

(51) Int. Cl.
*A61K 39/395* (2006.01)
*A61K 35/12* (2006.01)
*C07K 14/00* (2006.01)

(52) U.S. Cl. .................. 530/350; 424/184.1; 424/277.1

(58) Field of Classification Search .................. None
See application file for complete search history.

(56) References Cited

U.S. PATENT DOCUMENTS

| 2003/0175250 | A1* | 9/2003 | Jager et al. ............. 424/93.7 |
| 2003/0194704 | A1* | 10/2003 | Penn et al. ............. 435/6 |
| 2004/0029197 | A1 | 2/2004 | Takimoto et al. |
| 2004/0181048 | A1* | 9/2004 | Wang ............. 536/24.3 |
| 2005/0196754 | A1* | 9/2005 | Drmanac et al. ............. 435/6 |

FOREIGN PATENT DOCUMENTS

| WO | WO-01/75067 A2 | 10/2001 |
| WO | WO-03/045427 A2 | 6/2003 |

OTHER PUBLICATIONS

Sequnece search result 2010.*
GenBank Accession No. AAS72276; Dramanac et al.; Feb. 13, 2002.
GenBank Accession No. ACH81576; Penn et al.; Jul. 29, 2004.
EMBL Accession No. AK097631; Isogai et al.; created Jul. 16, 2002, last updated Sep. 14, 2006.
Akcakanat et al., NY-ESO-1 expression and its serum immunoreactivity in esophageal cancer. Cancer Chemother Pharmacol. Jul. 2004;54(1):95-100. Epub Apr. 30, 2004.
Aradhya et al., Multiple pathogenic and benign genomic rearrangements occur at a 35 kb duplication involving the NEMO and LAGE2 genes. Hum Mol Genet. Oct. 15, 2001;10(22):2557-67.
Bodey, Cancer-testis antigens: promising targets for antigen directed antineoplastic immunotherapy. Expert Opin Biol Ther. Aug. 2002;2(6):577-84.
Chen et al., Immunodominant CD4+ responses identified in a patient vaccinated with full-length NY-ESO-1 formulated with ISCOMATRIX adjuvant. Proc Natl Acad Sci U S A. Jun. 22, 2004;101(25):9363-8. Epub Jun. 14, 2004.
Coral et al., 5-aza-2'-deoxycytidine-induced expression of functional cancer testis antigens in human renal cell carcinoma: immunotherapeutic implications. Clin Cancer Res. Aug. 2002;8(8):2690-5.
Davis et al., Recombinant NY-ESO-1 protein with ISCOMATRIX adjuvant induces broad integrated antibody and CD4(+) and CD8(+) T cell responses in humans. Proc Natl Acad Sci U S A. Jul. 20, 2004;101(29):10697-702. Epub Jul. 13, 2004.
De Smet et al., DNA methylation is the primary silencing mechanism for a set of germ line- and and tumor-specific genes with a CpG-rich promoter. Mol Cell Biol. Nov. 1999;19(11):7327-35.
Dunn et al., Cancer immunoediting: from immunosurveillance to tumor escape. Nat Immunol. Nov. 2002:3(11):991-8.
Dunn et al., The three Es of cancer immunoediting. Annu Rev Immunol. 2004;22:329-60.
Egland et al., Characterization of overlapping XAGE-1 transcripts encoding a cancer testis antigen expressed in lung, breast, and other types of cancers. Mol Cancer Ther. May 2002;1(7):441-50.
Fosså et al., NY-ESO-1 protein expression and humoral immune responses in prostate cancer. Prostate. Jun. 1, 2004;59(4):440-7.
Güre et al., The SSX gene family: characterization of 9 complete genes. Int J Cancer. Oct. 10, 2002;101(5):448-53.
Gure et al., SSX: a multigene family with several members transcribed in normal testis and human cancer. Int J Cancer. Sep. 17, 1997;72(6):965-71.
Han et al., Long-term biochemical disease-free and cancer-specific survival following anatomic radical retropubic prostatectomy. The 15-year Johns Hopkins experience. Urol Clin North Am. Aug. 2001;28(3):555-65. e-publication 11 pages.
Huang et al., Novel development-related alternative splices in human testis identified by cDNA microarrays. J Androl. Mar.-Apr. 2005;26(2):189-96.
Jäger et al., Identification of a tissue-specific putative transcription factor in breast tissue by serological screening of a breast cancer library. Cancer Res. Mar. 1, 2001;61(5):2055-61.
Jäger et al., Induction of primary NY-ESO-1 immunity: CD8+ T lymphocyte and antibody responses in peptide-vaccinated patients with NY-ESO-1+ cancers. Proc Natl Acad Sci U S A. Oct. 24, 2000;97(22):12198-203.

(Continued)

*Primary Examiner* — Lei Yao
(74) *Attorney, Agent, or Firm* — Wolf, Greenfield & Sacks, P.C.

(57) ABSTRACT

The invention relates to CTSP polypeptides and the nucleic acid molecules that encode them. The invention further relates to the use of the nucleic acid molecules, polypeptides and fragments thereof in methods and compositions for the diagnosis, prognosis and treatment of diseases, such as cancer. More specifically, the invention relates to the discovery of a novel cancer/testis (CT) antigen, CTSP-1.

11 Claims, 7 Drawing Sheets

OTHER PUBLICATIONS

Jäger et al., Humoral immune responses of cancer patients against "Cancer-Testis" antigen NY-ESO-1: correlation with clinical events. Int J Cancer. Oct. 22, 1999;84(5):506-10.

Kufer et al., Heterogeneous expression of MAGE-A genes in occult disseminated tumor cells: a novel multimarker reverse transcription-polymerase chain reaction for diagnosis of micrometastatic disease. Cancer Res. Jan. 1, 2002;62(1):251-61.

Lea et al., Autoimmunogenicity of the human sperm protein Sp17 in vasectomized men and identification of linear B cell epitopes. Fertil Steril. Feb. 1997;67(2):355-61.

Lethé et al., LAGE-1, a new gene with tumor specificity. Int J Cancer. Jun. 10, 1998;76(6):903-8.

Lucas et al., A new MAGE gene with ubiquitous expression does not code for known MAGE antigens recognized by T cells. Cancer Res. Aug. 15, 1999;59(16):4100-3.

Maio et al., Analysis of cancer/testis antigens in sporadic medullary thyroid carcinoma: expression and humoral response to NY-ESO-1. J Clin Endocrinol Metab. Feb. 2003;88(2):748-54.

Marchand et al., Tumor regressions observed in patients with metastatic melanoma treated with an antigenic peptide encoded by gene MAGE-3 and presented by HLA-A1. Int J Cancer. Jan. 18, 1999;80(2):219-30.

McCurdy et al., MAGE Xp-2: a member of the MAGE gene family isolated from an expression library using systemic lupus erythematosus sera. Mol Genet Metab. Jan. 1998;63(1):3-13.

Nakada et al., NY-ESO-1 mRNA expression and immunogenicity in advanced prostate cancer. Cancer Immun. Jul. 31, 2003;3:10.

Nelson et al., The role of inflammation in the pathogenesis of prostate cancer. J Urol. Nov. 2004;172(5 Pt 2):S6-11; discussion S11-2.

Old, Cancer/Testis (CT) antigens—a new link between gametogenesis and cancer. Cancer Immun. Mar. 30, 2001;1:1.

Parmigani et al., Characterization of a cancer/testis (CT) antigen gene family capable of eliciting humoral response in cancer patients. Proc Natl Acad Sci U S A. Nov. 28, 2006;103(48):18066-71. Epub Nov. 17, 2006.

Pöld et al., Identification of a new, unorthodox member of the MAGE gene family. Genomics. Jul. 15, 1999;59(2):161-7.

Prikler et al., [Adaptive immunotherapy of the advanced prostate cancer—cancer testis antigen (CTA) as possible target antigens]. Aktuelle Urol. Aug. 2004;35(4):326-30. German. English abstract only.

Reymond et al., Nineteen additional unpredicted transcripts from human chromosome 21. Genomics. Jun. 2002;79(6):824-32.

Rocha et al., Recognition of melanoma cell antigens with antibodies present in sera from patients with vitiligo. Int J Dermatol. Nov. 2000;39(11):840-3.

Scanlan et al., Cancer/testis antigens: an expanding family of targets for cancer immunotherapy. Immunol Rev. Oct. 2002;188:22-32.

Scanlan et al., The cancer/testis genes: Review, standardization, and commentary. Cancer Immun. Jan. 23, 2004;4:1-15.

Sharma et al., Frequency of NY-ESO-1 and Lage-1 expression in bladder cancer and evidence of a new NY-ESO-1 T-cell epitope in a patient with bladder cancer. Cancer Immun. Dec. 18, 2003;3:19.

Shimura et al., Reduced infiltration of tumor-associated macrophages in human prostate cancer: association with cancer progression. Cancer Res. Oct. 15, 2000;60(20):5857-61.

Simpson et al., Cancer/testis antigens, gametogenesis and cancer. Nat Rev Cancer. Aug. 2005;5(8):615-25.

Stockert et al., A survey of the humoral immune response of cancer patients to a panel of human tumor antigens. J Exp Med. Apr. 20, 1998;187(8):1349-54.

Sugita et al., NY-ESO-1 expression and immunogenicity in malignant and benign breast tumors. Cancer Res. Mar. 15, 2004;64(6):2199-204.

Vesalainen Histological grade, perineural infiltration, tumour-infiltrating lymphocytes and apoptosis as determinants of long-term prognosis in prostatic adenocarcinoma. Eur J Cancer. 1994;30A(12):1797-803. Abstract only.

Weber et al., Expression of the MAGE-1 tumor antigen is up-regulated by the demethylating 5-aza-2'-deoxycytidine. Cancer Res. Apr. 1994;54(7):1766-71.

Yakirevich et al., Expression of the MAGE-A4 and NY-ESO-1 cancer-testis antigens in serous ovarian neoplasms. Clin Cancer Res. Dec. 15, 2003;9(17):6453-60.

Zendman et al., Cancer/testis-associated genes: identification, expression profile, and putative function. J Cell Physiol. Mar. 2003;194(3):272-88.

* cited by examiner

SEQUENCE LISTING

<160> NUMBER OF SEQ ID NOS: 57

<210> SEQ ID NO 1
<211> LENGTH: 3915

```
<212> TYPE: DNA
<213> ORGANISM: Homo sapiens

<400> SEQUENCE: 1
ggagaggctg gagtgtccaa aagcttggcc gactgagatt gctagtcgtg tcagggcggg      60
tgcgggactg aagaagggcg agggcgagcg gcggggactg gggaagggcg agcagcggga     120
ggcacgggct ctctctagca ggtggctgca gccatggaga ggctctgtgc cgccgctgtc     180
aagggccaga cgggcccaga gcgcccaagc cccttcagtc agctggtcta caccaacaac     240
gactcttacg tgattcacca tgggatctc aggaagatcc acaaagctgc ctcccgggcc      300
aagcctggaa gctggagagg atgatgaaga agacgacaat ggacctgaac ataagagatg     360
cgaagaagag gactgctcta cactgggcct gtgccaatgg ccatgcagaa gtagtaacac     420
ttctggtaga tagaaagtgc cagcttgacg tccttgatgg cgaaaacagg acaactctga     480
tgaaggctct gcaatgccag agggaggctt gtgcaaatat ctccatagat tctggtgctg     540
atccaaatat tgtagatgtg tatggcaaca cagctgtcca ttatgctgtt aacagtgaga     600
atttgtcagt ggtggcaaaa ttgctgtcct gtggtacaga cattaaagtg aagaacaagt     660
tagtgtaaaa ctacaagaaa gtaaaatttg cctgcataaa ttgagtcaac atgtaaaatt     720
taggagacat gcagaaatct ggatttcctc ttaaaggatt gaatcttgtg tctcttgagc     780
ccgtatgact gtttggcagc cacttcctta gtgacccatt tagagcagga gtgcctgaca     840
ttggcatttg gaatcttggg atcattgata gaagagaatc aagctggcca cacaccactt     900
ttattggcca taggaaaag aagtgagcaa attgtgaat ttttactgac aaaaaatgca       960
aatgcaaatg gagttgataa gtttaaatgc acagccctca tgcttgccat atgtcatgga    1020
tcatcagaga tagttggcaa gcttcttcag caaaatgttg acatctgtgc tgaagctaca    1080
tgcggaatga ttgcagaacg ttatgctgtt gcttgtggat ttaatctcta agtgtttaca    1140
tttaaaggct agcattcatc aacaactttt ggaatataaa caaagatat ctaaaaattc     1200
tcaaaatagt aatccagaag gaacatctga aggaacacct gacgaggctg cacccttggc    1260
ggaaagaaca cctgacacgg ctgaaagctt ggtggaaaga acacctgacg aataggatac    1320
agtgaattcc tcttcaaaga ttttagcctg taaacatcct ttaaaattca agaggggga     1380
agattaagta caatgagttc tgagttcctc atcaaagaac aaatatgtca gtatgttcag    1440
cttctccgtt ctttgttctc cgttttaaag tttaacttcc tcgttcgtta tgcctccttg    1500
cccctagttt cattaaacaa cccccttcta gcctctaaca cctgctttgt ctttagtcat    1560
tcttagtaac ctgctctgtc cttagtcatc cttagacacc tgctctgtaa ctgtcttttcc   1620
cgctgaaact actcaccctg ccactccagc tcatacccct gccctctttg aaatagccaa    1680
tctgaattgg cttagagtgt gcagtccaac cctatccaat agggaaaaga cacaacagta    1740
gggactagct gcgttagaaa taagaacact ttccctcc ttgtccggtg tgatcttgcc      1800
tttgctccat ctgcaagacc actcttccat agaagtaaat ttgccttgct gtaaaaactt    1860
gttgctggag tgctgacggt tctttgtggc accgaaaatt attttccaaa aatttgaggg    1920
cccacccaac attcccattc tcctctgggg gagggtccag tcctctccct tgaggaggtg    1980
caccccgctg cctcgttgca gtggccataa aggtaaggaa tcaagactca actggtgcga    2040
ttaataaacc cgggctctca gcaacgtgga aagaaacagg ccagcaactc tggggaaagg    2100
atcttcacat accgtggcga ccagtgtgct cttgccattg ctccatccgc aagactcacc    2160
cttctataga agtaaatttg ccttgctgga gtgctaactc ttctttgtgt caccaaaaag    2220
ttatttccaa catgaaggtg cacccttggt ggagggaaca tctgacgaag ttcaatgttt    2280
```

-continued

```
ggggaaagca atatctggaa agattgaaca gtcagcagga gaaacaccta ggaaaattac      2340
aaggcctgtg aaagaaacat ctgagaaatt tgcatggcca caagaaaggc cttcaaagac      2400
cacacgggag gaaaaagaaa catctgtaaa gactgaatga gtggcaggag taacatttaa      2460
taaaattgaa gttttggaag aaggaacatc taagatgatc acatgtccta caaaaaaaca      2520
gctacaaaag caagtacaaa tggtatactg ttgatgtggt tgataattct ggtatccaag      2580
aagaaatctc ccaagatcct acctaacttt ttgtaactaa agcggcatac atacacaggt      2640
agtgggaaaa tgtctagagt gattcaacta gcctatcaaa aatcttggat gcagttcttt      2700
cttgtgaaag agcaagggaa cttaaaaaat atccctgtgg gccaggcgcc atggctcaca      2760
cctgtaatct catcactttg ggaggccaag gcgggcagat catgacgtca ggagatcaag      2820
accatcctgg ctaacacagt gaaacccgt ctctactaaa aatacaaaaa aaaaaattag      2880
ccgggcgtgg tggcaggtga ctatagtccc agctactcgg gaggctgagg caggagaatg      2940
gcatgaaccc gggaggcgga gcttgcagtg agtggagatc gcgccactgc actccagcct      3000
aggcaacaga gcgagactcc gtcaaaaaaa ataaagaaa aaaaaatccc tgtgaacaac      3060
ttacagcaaa aatgaaacaa atgaaaaata agcttcgtgt actacaaaag gaactaacag      3120
aagcaaaata aataaaatca tagagaatca aaaacttaaa agagaacaag agctctgcag      3180
tgtgagattg actttaaacc aagaagaaga gaagagaaga aatgccaata tattaaatga      3240
aaaattaggg aagaattagg aaaaatcgaa gagcaacaaa agaaaaagtt agaagtgaag      3300
caacttgagc tcactctccg aatatacaaa atatggaatt gaagactgta agaagtaatt      3360
tgaatcagct caatcaatcg ctgggccgca atctgtcacc aaggctaggg tgcagtggca      3420
caatcatgga tcactgcagc ctcaaactct ggggctcaag cagacctcct gtctcagcct      3480
accaagtagc tgggaccaca ggccatatga aatggaggca atttgtttat cagtctgagt      3540
ctccagaact cctgaatttt ttgccaagga aactggagaa actctcgtcc aggtaccaac      3600
caaggagatt atttctacaa agaaggaac agacactgaa tgactcattt cccttcctct      3660
cacatggaag cagaattaga cactcctgcc agcctgaccc aagtctgtac aggacatcct      3720
gaaatgtctt aaagattccc gggtgattgt gagaggattc ctagtgacca tggactgatg      3780
accgtatgtt gatccaggta ggaaagactc aagctgatta taaatagaaa atggaactgc      3840
cctggtacag ctccagaacc tggatctatg tgtgatatca cctgttctga ttagctaggt      3900
cttaggtaag agaaa                                                      3915
```

<210> SEQ ID NO 2
<211> LENGTH: 3829
<212> TYPE: DNA
<213> ORGANISM: Homo sapiens

<400> SEQUENCE: 2

```
ggagaggctg gagtgtccaa aagcttggcc gactgagatt gctagtcgtg tcagggcggg       60
tgcgggactg aagaagggcg agggcgagcg gcggggactg gggaagggcg agcagcggga      120
ggcacgggct ctctctagca ggtggctgca gccatggaga ggctctgtgc cgccgctgtc      180
aagggccaga cgggcccaga gcgcccaagc cccttcagtc agctggtcta caccaacaac      240
gactcttacg tgattcacca tggggatctc aggaagatcc acaaagctgc ctcccgggcc      300
aagcctggaa gctggagagg atgatgaaga agacgacaat ggacctgaac ataagagatg      360
cgaagaagag gactgctcta cactgggcct gtgccaatgg ccatgcagaa gtagtaacac      420
ttctggtaga tagaaagtgc cagcttgacg tccttgatgg cgaaaacagg acaactctga      480
```

```
tgaaggctct gcaatgccag agggaggctt gtgcaaatat tctcatagat tctggtgctg    540
atccaaatat tgtagatgtg tatggcaaca cagctgtcca ttatgctgtt aacagtgaga    600
atttgtcagt ggtggcaaaa ttgctgtcct gtggtacaga cattaaagtg aagaacaagt    660
tagtgtaaaa ctacaagaaa gtaaaatttg cctgcataaa ttgagtcaac atgtaaaatt    720
taggagacat gcagaaatct ggatttcctc ttaaaggatt gaatcttgtg tctcttgagc    780
ccgtatgact gtttgggctg ccacacacc acttttattg gccataagga aaagaagtga    840
gcaaattgtg gaatttttac tgacaaaaaa tgcaaatgca atggagttga taagtttaa    900 atgcacagcc ctcatgcttg ccatatgtca tggatcatca gagatagttg gcaagcttct    960
tcagcaaaat gttgacatct gtgctgaagc tacatgcgga atgattgcag aacgttatgc   1020
tgttgcttgt ggatttaatc tctaagtgtt tacatttaaa ggctagcatt catcaacaac   1080
ttttggaata taaacaaaag atatctaaaa attctcaaaa tagtaatcca gaaggaacat   1140
ctgaaggaac acctgacgag gctgcaccct ggcggaaaag aacacctgac acggctgaaa   1200
gcttggtgga agaacacct gacgaatagg atacagtgaa ttcctcttca aagattttag   1260
cctgtaaaca tcctttaaaa ttcaagaggg gggaagatta agtacaatga gttctgagtt   1320
cctcatcaaa gaacaaatat gtcagtatgt tcagcttctc cgttctttgt tctccgtttt   1380
aaagtttaac ttcctcgttc gttatgcctc cttgccccta gtttcattaa caacccccct   1440
tctagcctct aacacctgct ttgtctttag tcattcttag taacctgctc tgtccttagt   1500
catccttaga cacctgctct gtaactgtct ttcccgctga aactactcac cctgccactc   1560
cagctcatac ccctgccctc tttgaaatag ccaatctgaa ttggcttaga gtgtgcagtc   1620
caaccctatc caatagggaa aagacacaac agtagggact agctgcgtta gaaataagaa   1680
cactttcccc tcccttgtcc ggtgtgatct tgcctttgct ccatctgcaa gaccactctt   1740
ccatagaagt aaatttgcct tgctgtaaaa acttgttgct ggagtgctga cggttctttg   1800
tggcaccgaa aattattttc caaaaatttg agggcccacc caacattccc attctcctct   1860
gggggagggt ccagtcctct cccttgagga ggtgcacccc gctgcctcgt tgcagtggcc   1920
ataaaggtaa ggaatcaaga ctcaactggt gcgattaata aacccgggct ctcagcaacg   1980
tggaaagaaa caggccagca actctgggga aaggatcttc acataccgtg cgaccagtg   2040 tgctcttgcc attgctccat ccgcaagact caccttcta tagaagtaaa tttgccttgc   2100
tggagtgcta actcttcttt gtgtcaccaa aaagttattt ccaacatgaa ggtgcaccct   2160
tggtggaggg aacatctgac gaagttcaat gtttgggaa agcaatatct ggaaagattg   2220
aacagtcagc aggagaaaca cctaggaaaa ttacaaggcc tgtgaaagaa acatctgaga   2280
aatttgcatg gccacaagaa aggccttcaa agaccacacg ggaggaaaaa gaaacatctg   2340
taaagactga atgagtggca ggagtaacat ttaataaaat tgaagttttg gaagaaggaa   2400
catctaagat gatcacatgt cctacaaaaa aacagctaca aaagcaagta caaatggtat   2460
actgttgatg tggttgataa ttctggtatc caagaagaaa tctcccaaga tcctacctaa   2520 cttttttgtaa ctaaagcggc atacatacac aggtagtggg aaaatgtcta gagtgattca   2580
actagcctat caaaaatctt ggatgcagtt cttcttgtg aaagagcaag gaacttaaa   2640 aaatatccct gtgggccagg cgccatggct cacacctgta atctcatcac tttgggaggc   2700
caaggcgggc agatcatgac gtcaggagat caagaccatc ctggctaaca cagtgaaacc   2760
ccgtctctac taaaaataca aaaaaaaaaa ttagccgggc gtggtggcag gtgactatag   2820
tcccagctac tcgggaggct gaggcaggag aatggcatga acccgggagg cggagcttgc   2880
```

| | |
|---|---|
| agtgagtgga gatcgcgcca ctgcactcca gcctaggcaa cagagcgaga ctccgtcaaa | 2940 |
| aaaaataaaa gaaaaaaaaa tccctgtgaa caacttacag caaaaatgaa acaaatgaaa | 3000 |
| aataagcttc gtgtactaca aaaggaacta acagaagcaa aataaataaa atcatagaga | 3060 |
| atcaaaaact taaaagagaa caagagctct gcagtgtgag attgactta aaccaagaag | 3120 |
| aagagaagag aagaaatgcc aatatattaa atgaaaaatt agggaagaat taggaaaaat | 3180 |
| cgaagagcaa caaagaaaa agttagaagt gaagcaactt gagctcactc tccgaatata | 3240 |
| caaaatatgg aattgaagac tgtaagaagt aatttgaatc agctcaatca atcgctgggc | 3300 |
| cgcaatctgt caccaaggct agggtgcagt ggcacaatca tggatcactg cagcctcaaa | 3360 |
| ctctggggct caagcagacc tcctgtctca gcctaccaag tagctgggac cacaggccat | 3420 |
| atgaaatgga ggcaatttgt ttatcagtct gagtctccag aactcctgaa tttttttgcca | 3480 |
| aggaaactgg agaaactctc gtccaggtac caaccaagga gattatttct acaaaagaag | 3540 |
| gaacagacac tgaatgactc atttcccttc ctctcacatg gaagcagaat tagacactcc | 3600 |
| tgccagcctg acccaagtct gtacaggaca tcctgaaatg tcttaaagat tcccgggtga | 3660 |
| ttgtgagagg attcctagtg accatggact gatgaccgta tgttgatcca ggtaggaaag | 3720 |
| actcaagctg attataaata gaaatggaa ctgccctggt acagctccag aacctggatc | 3780 |
| tatgtgtgat atcacctgtt ctgattagct aggtcttagg taagagaaa | 3829 |

<210> SEQ ID NO 3
<211> LENGTH: 3778
<212> TYPE: DNA
<213> ORGANISM: Homo sapiens

<400> SEQUENCE: 3

| | |
|---|---|
| ggagaggctg gagtgtccaa aagcttggcc gactgagatt gctagtcgtg tcagggcggg | 60 |
| tgcgggactg aagaagggcg agggcgagcg gcgggactg gggaagggcg agcagcggga | 120 |
| ggcacgggct ctctctagca ggtggctgca gccatggaga ggctctgtgc cgccgctgtc | 180 |
| aagggccaga cgggcccaga gcgcccaagc cccttcagtc agctggtcta caccaacaac | 240 |
| gactcttacg tgattcacca tggggatctc aggaagatcc acaaagctgc ctcccgggcc | 300 |
| aagcctggaa gctggagagg atgatgaaga agacgacaat ggacctgaac ataagagatg | 360 |
| cgaagaagag gactgctcta cactgggcct gtgccaatgg ccatgcagaa gtagtaacac | 420 |
| ttctggtaga tagaaagtgc cagcttgacg tccttgatgg cgaaaacagg acaactctga | 480 |
| tgaaggctct gcaatgccag agggaggctt gtgcaaatat tctcatagat tctggtgctg | 540 |
| atccaaatat tgtagatgtg tatggcaaca cagctgtcca ttatgctgtt aacagtgaga | 600 |
| atttgtcagt ggtggcaaaa ttgctgtcct gtggtacaga cattaaagtg aagaacaagc | 660 |
| agccacttcc ttagtgaccc atttagcaga ggagtgcctg acattggcat ttggaatctt | 720 |
| gggatcattg atagaagaga atcaagctgg ccacacacca cttttattgg ccataaggaa | 780 |
| aagaagtgag caaattgtgg aattttact gacaaaaaat gcaaatgcaa atggagttga | 840 |
| taagtttaaa tgcacagccc tcatgcttgc catatgtcat ggatcatcag agatagttgg | 900 |
| caagcttctt cagcaaaatg ttgacatctg tgctgaagct acatgcggaa tgattgcaga | 960 |
| acgttatgct gttgcttgtg gatttaatct ctaagtgttt acatttaaag gctagcattc | 1020 |
| atcaacaact tttggaatat aaacaaaaga tatctaaaaa ttctcaaaat agtaatccag | 1080 |
| aaggaacatc tgaaggaaca cctgacgagg ctgcacccttt ggcggaaaga acacctgaca | 1140 |
| cggctgaaag cttggtggaa agaacacctg acgaatagga tacagtgaat tcctcttcaa | 1200 |

```
agattttagc ctgtaaacat cctttaaaat tcaagagggg ggaagattaa gtacaatgag    1260
ttctgagttc ctcatcaaag aacaaatatg tcagtatgtt cagcttctcc gttctttgtt    1320
ctccgtttta aagtttaact tcctcgttcg ttatgcctcc ttgcccctag tttcattaaa    1380
caaccccctt ctagcctcta cacctgcttt tgtctttagt cattcttagt aacctgctct    1440
gtccttagtc atccttagac acctgctctg taactgtctt tcccgctgaa actactcacc    1500
ctgccactcc agctcatacc cctgccctct ttgaaatagc caatctgaat tggcttagag    1560
tgtgcagtcc aaccctatcc aatagggaaa agacacaaca gtagggacta gctgcgttag    1620
aaataagaac actttccct cccttgtccg gtgtgatctt gcctttgctc catctgcaag    1680
accactcttc catagaagta aatttgcctt gctgtaaaaa cttgttgctg gagtgctgac    1740
ggttctttgt ggcaccgaaa attattttcc aaaaatttga gggcccaccc aacattccca    1800
ttctcctctg ggggagggtc cagtcctctc ccttgaggag gtgcacccg ctgcctcgtt    1860 gcagtggcca taaggtaag gaatcaagac tcaactggtg cgattaataa acccgggctc    1920
tcagcaacgt ggaaagaaac aggccagcaa ctctggggaa aggatcttca cataccgtgg    1980
cgaccagtgt gctcttgcca ttgctccatc cgcaagactc acccttctat agaagtaaat    2040
ttgccttgct ggagtgctaa ctcttctttg tgtcaccaaa aagttatttc caacatgaag    2100 gtgcacccctt ggtggaggga acatctgacg aagttcaatg tttggggaaa gcaatatctg    2160
gaaagattga acagtcagca ggagaaacac ctaggaaaat tacaaggcct gtgaaagaaa    2220
catctgagaa atttgcatgg ccacaagaaa ggccttcaaa gaccacacgg gaggaaaaag    2280
aaacatctgt aaagactgaa tgagtggcag gagtaacatt taataaaatt gaagttttgg    2340
aagaaggaac atctaagatg atcacatgtc ctacaaaaaa acagctacaa aagcaagtac    2400
aaatggtata ctgttgatgt ggttgataat tctggtatcc aagaagaaat ctcccaagat    2460
cctacctaac tttttgtaac taaagcggca tacatacaca ggtagtggga aaatgtctag    2520
agtgattcaa ctagcctatc aaaaatcttg gatgcagttc tttcttgtga agagcaagg    2580 gaacttaaaa aatatccctg tgggccaggc gccatggctc acacctgtaa tctcatcact    2640
ttgggaggcc aaggcgggca gatcatgacg tcaggagatc aagaccatcc tggctaacac    2700
agtgaaaccc cgtctctact aaaaatacaa aaaaaaaat tagccgggcg tggtggcagg    2760
tgactatagt cccagctact cgggaggctg aggcaggaga atggcatgaa cccgggaggc    2820
ggagcttgca gtgagtggag atcgcgccac tgcactccag cctagcaac agagcgagac    2880 tccgtcaaaa aaaataaaag aaaaaaaaat ccctgtgaac aacttacagc aaaaatgaaa    2940
caaatgaaaa ataagcttcg tgtactacaa aaggaactaa cagaagcaaa ataaataaaa    3000
tcatagagaa tcaaaaactt aaaagagaac aagagctctg cagtgtgaga ttgactttaa    3060
accaagaaga agagaagaga agaaatgcca atatattaaa tgaaaaatta gggaagaatt    3120
aggaaaaatc gaagagcaac aaaagaaaaa gttagaagtg aagcaacttg agctcactct    3180
ccgaatatac aaaatatgga attgaagact gtaagaagta atttgaatca gctcaatcaa    3240
tcgctgggcc gcaatctgtc accaaggcta gggtgcagtg gcacaatcat ggatcactgc    3300
agcctcaaac tctggggctc aagcagacct cctgtctcag cctaccaagt agctgggacc    3360
acaggccata tgaaatggag gcaatttgtt tatcagtctg agtctccaga actcctgaat    3420
tttttgccaa ggaaactgga gaaactctcg tccaggtacc aaccaaggag attatttcta    3480
caaaagaagg aacagacact gaatgactca tttcccttcc tctcacatgg aagcagaatt    3540
agacactcct gccagcctga cccaagtctg tacaggacat cctgaaatgt cttaaagatt    3600
```

```
cccgggtgat tgtgagagga ttcctagtga ccatggactg atgaccgtat gttgatccag    3660
gtaggaaaga ctcaagctga ttataaatag aaaatggaac tgccctggta cagctccaga    3720
acctggatct atgtgtgata tcacctgttc tgattagcta ggtcttaggt aagagaaa      3778

<210> SEQ ID NO 4
<211> LENGTH: 3752
<212> TYPE: DNA
<213> ORGANISM: Homo sapiens

<400> SEQUENCE: 4
ggagaggctg gagtgtccaa aagcttggcc gactgagatt gctagtcgtg tcagggcggg      60
tgcgggactg aagaagggcg agggcgagcg gcggggactg gggaagggcg agcagcggga    120
ggcacgggct ctctctagca ggtggctgca gccatggaga ggctctgtgc cgccgctgtc    180
aagggccaga cgggcccaga gcgcccaagc cccttcagtc agctggtcta caccaacaac    240
gactcttacg tgattcacca tggggatctc aggaagatcc acaaagctgc ctcccgggcc    300
aagcctggaa gctggagagg atgatgaaga agacgacaat ggacctgaac ataagagatg    360
cgaagaagag gactgctcta cactgggcct gtgccaatgg ccatgcagaa gtagtaacac    420
ttctggtaga tagaaagtgc cagcttgacg tccttgatgg cgaaaacagg acaactctga    480
tgaaggctct gcaatgccag agggaggctt gtgcaaatat tctcatagat tctggtgctg    540
atccaaatat tgtagatgtg tatggcaaca cagctgtcca ttatgctgtt aacagtgaga    600
atttgtcagt ggtggcaaaa ttgctgtcct gtggtacaga cattaaagtg aagaacaagt    660
tagtgtaaaa ctacaagaaa gtaaaatttg cctgcataaa ttgagtcaac atgtaaaatt    720
taggagacat gcagaaatct ggatttcctc ttaaaggatt gaatcttgtg tctcttgagc    780
ccgtatgact gtttggcagc acttcctta gtgacccatt tagagcagga gtgcctgaca     840
ttggcatttg gaatcttggg atcattgata agagagaatc aagctggcca cacaccactt    900
ttattggcca taaggaaaag aagtgagcaa attgtggaat ttttactgac aaaaaatgca    960
aatgcaaatg gagttgataa gtttaaatgc attcatcaac aacttttgga atataaacaa    1020
aagatatcta aaaattctca aaatagtaat ccagaaggaa catctgaagg aacacctgac    1080
gaggctgcac ccttggcgga agaacacct gacacggctg aaagcttggt ggaaagaaca     1140
cctgacgaat aggatacagt gaattcctct tcaaagattt tagcctgtaa acatcccttta    1200 aaattcaaga gggggaaga ttaagtacaa tgagttctga gttcctcatc aaagaacaaa     1260
tatgtcagta tgttcagctt ctccgttctt tgttctccgt tttaaagttt aacttcctcg    1320
ttcgttatgc ctccttgccc ctagtttcat taaacaaccc ccttctagcc tctaacacct    1380
gctttgtctt tagtcattct tagtaacctg ctctgtcctt agtcatcctt agacacctgc    1440
tctgtaactg tctttcccgc tgaaactact caccctgcca ctccagctca tacccctgcc    1500
ctctttgaaa tagccaatct gaattggctt agagtgtgca gtccaaccct atccaatagg    1560
gaaaagacac aacagtaggg actagctgcg ttagaaataa gaacactttc ccctcccttg    1620
tccggtgtga tcttgccttt gctccatctg caagaccact cttccataga agtaaatttg    1680
ccttgctgta aaaacttgtt gctggagtgc tgacggttct tgtggcacc gaaaattatt      1740 ttccaaaaat ttgagggccc acccaacatt cccattctcc tctggggag gtccagtcc       1800 tctcccttga ggaggtgcac cccgctgcct cgttgcagtg ccataaagg taaggaatca      1860 agactcaact ggtgcgatta ataaacccgg gctctcagca acgtgaaag aaacaggcca      1920 gcaactctgg ggaaaggatc ttcacatacc gtggcgacca gtgtgctctt gccattgctc    1980
```

| | |
|---|---|
| catccgcaag actcacccct ctatagaagt aaatttgcct tgctggagtg ctaactcttc | 2040 |
| tttgtgtcac caaaaagtta tttccaacat gaaggtgcac ccttggtgga gggaacatct | 2100 |
| gacgaagttc aatgtttggg gaaagcaata tctggaaaga ttgaacagtc agcaggagaa | 2160 |
| acacctagga aaattacaag gcctgtgaaa gaaacatctg agaaatttgc atggccacaa | 2220 |
| gaaaggcctt caaagaccac acgggaggaa aaagaaacat ctgtaaagac tgaatgagtg | 2280 |
| gcaggagtaa catttaataa aattgaagtt ttggaagaag aacatctaa gatgatcaca | 2340 |
| tgtcctacaa aaaacagct acaaagcaa gtacaaatgg tatactgttg atgtggttga | 2400 |
| taattctggt atccaagaag aaatctccca agatcctacc taactttttg taactaaagc | 2460 |
| ggcatacata cacaggtagt gggaaaatgt ctagagtgat tcaactagcc tatcaaaaat | 2520 |
| cttggatgca gttctttctt gtgaaagagc aagggaactt aaaaaatatc cctgtgggcc | 2580 |
| aggcgccatg gctcacacct gtaatctcat cactttggga ggccaaggcg gcagatcat | 2640 |
| gacgtcagga gatcaagacc atcctggcta acacagtgaa accccgtctc tactaaaaat | 2700 |
| acaaaaaaaa aaattagccg ggcgtggtgg caggtgacta tagtcccagc tactcgggag | 2760 |
| gctgaggcag gagaatggca tgaacccggg aggcggagct tgcagtgagt ggagatcgcg | 2820 |
| ccactgcact ccagcctagg caacagagcg agactccgtc aaaaaaaata aagaaaaaa | 2880 |
| aaatccctgt gaacaactta cagcaaaaat gaaacaaatg aaaaataagc ttcgtgtact | 2940 |
| acaaaaggaa ctaacagaag caaaataaat aaaatcatag gaatcaaaa acttaaaaga | 3000 |
| gaacaagagc tctgcagtgt gagattgact ttaaaccaag aagaagagaa gagaagaaat | 3060 |
| gccaatatat taaatgaaaa attagggaag aattaggaaa aatcgaagag caacaaaaga | 3120 |
| aaaagttaga agtgaagcaa cttgagctca ctctccgaat atacaaaata tggaattgaa | 3180 |
| gactgtaaga agtaatttga atcagctcaa tcaatcgctg ggccgcaatc tgtcaccaag | 3240 |
| gctagggtgc agtggcacaa tcatggatca ctgcagcctc aaactctggg gctcaagcag | 3300 |
| acctcctgtc tcagcctacc aagtagctgg gaccacaggc catatgaaat ggaggcaatt | 3360 |
| tgtttatcag tctgagtctc cagaactcct gaattttttg ccaaggaaac tggagaaact | 3420 |
| ctcgtccagg taccaaccaa ggagattatt tctacaaaag aaggaacaga cactgaatga | 3480 |
| ctcatttccc ttcctctcac atggaagcag aattagacac tcctgccagc ctgacccaag | 3540 |
| tctgtacagg acatcctgaa atgtcttaaa gattcccggg tgattgtgag aggattccta | 3600 |
| gtgaccatgg actgatgacc gtatgttgat ccaggtagga aagactcaag ctgattataa | 3660 |
| atagaaaatg gaactgccct ggtacagctc cagaacctgg atctatgtgt gatatcacct | 3720 |
| gttctgatta gctaggtctt aggtaagaga aa | 3752 |

<210> SEQ ID NO 5
<211> LENGTH: 3692
<212> TYPE: DNA
<213> ORGANISM: Homo sapiens

<400> SEQUENCE: 5

| | |
|---|---|
| ggagaggctg gagtgtccaa aagcttggcc gactgagatt gctagtcgtg tcagggcggg | 60 |
| tgcgggactg aagaagggcg agggcgagcg gcggggactg gggaagggcg agcagcggga | 120 |
| ggcacgggct ctctctagca ggtggctgca gccatggaga ggctctgtgc cgccgctgtc | 180 |
| aagggccaga cgggcccaga gcgcccaagc cccttcagtc agctggtcta caccaacaac | 240 |
| gactcttacg tgattcacca tggggatctc aggaagatcc acaaagctgc ctcccgggcc | 300 |
| aagcctggaa gctggagagg atgatgaaga agacgacaat ggacctgaac ataagagatg | 360 |

```
cgaagaagag gactgctcta cactgggcct gtgccaatgg ccatgcagaa gtagtaacac    420
ttctggtaga tagaaagtgc cagcttgacg tccttgatgg cgaaaacagg acaactctga    480
tgaaggctct gcaatgccag agggaggctt gtgcaaatat tctcatagat tctggtgctg    540
atccaaatat tgtagatgtg tatggcaaca cagctgtcca ttatgctgtt aacagtgaga    600
atttgtcagt ggtggcaaaa ttgctgtcct gtggtacaga cattaaagtg aagaacaagg    660
ctggccacac accacttttta ttggccataa ggaaaagaag tgagcaaatt gtggaatttt    720
tactgacaaa aaatgcaaat gcaaatggag ttgataagtt taaatgcaca gccctcatgc    780
ttgccatatg tcatggatca tcagagatag ttggcaagct tcttcagcaa atgttgaca    840 tctgtgctga agctacatgc ggaatgattg cagaacgtta tgctgttgct tgtggattta    900
atctctaagt gtttacattt aaaggctagc attcatcaac aacttttgga atataaacaa    960
aagatatcta aaattctca aaatagtaat ccagaaggaa catctgaagg aacacctgac    1020
gaggctgcac ccttggcgga aagaacacct gacacggctg aaagcttggt ggaaagaaca    1080
cctgacgaat aggatacagt gaattcctct tcaaagattt tagcctgtaa acatccttta    1140
aaattcaaga gggggaaga ttaagtacaa tgagttctga gttcctcatc aaagaacaaa    1200
tatgtcagta tgttcagctt ctccgttctt tgttctccgt tttaaagttt aacttcctcg    1260
ttcgttatgc ctccttgccc ctagtttcat taaacaaccc ccttctagcc tctaacacct    1320
gctttgtctt tagtcattct tagtaacctg ctctgtcctt agtcatcctt agacacctgc    1380
tctgtaactg tcttttcccgc tgaaactact caccctgcca ctccagctca tacccctgcc    1440
ctctttgaaa tagccaatct gaattggctt agagtgtgca gtccaaccct atccaatagg    1500
gaaaagacac aacagtaggg actagctgcg ttagaaataa gaacactttc ccctcccttg    1560
tccggtgtga tcttgccttt gctccatctg caagaccact cttccataga agtaaatttg    1620
ccttgctgta aaaacttgtt gctggagtgc tgacggttct ttgtggcacc gaaaattatt    1680
ttccaaaaat ttgagggccc acccaacatt cccattctcc tctggggag ggtccagtcc    1740 tctcccttga ggaggtgcac cccgctgcct cgttgcagtg gccataaagg taaggaatca    1800
agactcaact ggtgcgatta ataaacccgg gctctcagca acgtggaaag aaacaggcca    1860
gcaactctgg ggaaaggatc ttcacatacc gtggcgacca gtgtgctctt gccattgctc    1920
catccgcaag actcacccctt ctatagaagt aaatttgcct tgctggagtg ctaactcttc    1980
tttgtgtcac caaaaagtta tttccaacat gaaggtgcac ccttggtgga gggaacatct    2040
gacgaagttc aatgtttggg gaaagcaata tctggaaaga ttgaacagtc agcaggagaa    2100
acacctagga aaattacaag gcctgtgaaa gaaacatctg agaaatttgc atggccacaa    2160
gaaaggcctt caaagaccac acgggaggaa aaagaaacat ctgtaaagac tgaatgagtg    2220
gcaggagtaa catttaataa aattgaagtt ttggaagaag gaacatctaa gatgatcaca    2280
tgtcctacaa aaaacagct acaaaagcaa gtacaaatgg tatactgttg atgtggttga    2340
taattctggt atccaagaag aaatctccca agatcctacc taacttttg taactaaagc    2400 ggcatacata cacaggtagt gggaaaatgt ctagagtgat tcaactagcc tatcaaaaat    2460
cttggatgca gttctttctt gtgaaagagc aagggaactt aaaaaatatc cctgtgggcc    2520
aggcgccatg gctcacacct gtaatctcat cactttggga ggccaaggcg gcagatcat    2580 gacgtcagga gatcaagacc atcctggcta acacagtgaa accccgtctc tactaaaaat    2640 acaaaaaaa aaattagccg ggcgtggtgg caggtgacta tagtcccagc tactcgggag    2700
gctgaggcag gagaatggca tgaacccggg aggcggagct tgcagtgagt ggagatcgcg    2760
```

```
ccactgcact ccagcctagg caacagagcg agactccgtc aaaaaaaata aagaaaaaa    2820 aaatccctgt gaacaactta cagcaaaaat gaaacaaatg aaaataagc ttcgtgtact     2880 acaaaaggaa ctaacagaag caaaataaat aaaatcatag agaatcaaaa acttaaaaga    2940
gaacaagagc tctgcagtgt gagattgact ttaaaccaag aagaagagaa gagaagaaat    3000
gccaatatat taaatgaaaa attagggaag aattaggaaa aatcgaagag caacaaaaga    3060
aaaagttaga agtgaagcaa cttgagctca ctctccgaat atacaaaata tggaattgaa    3120
gactgtaaga agtaatttga atcagctcaa tcaatcgctg ggccgcaatc tgtcaccaag    3180
gctagggtgc agtggcacaa tcatggatca ctgcagcctc aaactctggg gctcaagcag    3240
acctcctgtc tcagcctacc aagtagctgg gaccacaggc catatgaaat ggaggcaatt    3300
tgtttatcag tctgagtctc cagaactcct gaattttttg ccaaggaaac tggagaaact    3360
ctcgtccagg taccaaccaa ggagattatt tctacaaaag aaggaacaga cactgaatga    3420
ctcatttccc ttcctctcac atggaagcag aattagacac tcctgccagc ctgacccaag    3480
tctgtacagg acatcctgaa atgtcttaaa gattcccggg tgattgtgag aggattccta    3540
gtgaccatgg actgatgacc gtatgttgat ccaggtagga aagactcaag ctgattataa    3600
atagaaaatg gaactgccct ggtacagctc cagaacctgg atctatgtgt gatatcacct    3660
gttctgatta gctaggtctt aggtaagaga aa                                 3692

<210> SEQ ID NO 6
<211> LENGTH: 3666
<212> TYPE: DNA
<213> ORGANISM: Homo sapiens

<400> SEQUENCE: 6
ggagaggctg gagtgtccaa aagcttggcc gactgagatt gctagtcgtg tcagggcggg     60
tgcgggactg aagaagggcg agggcgagcg gcggggactg gggaagggcg agcagcggga    120
ggcacgggct ctctctagca ggtggctgca gccatggaga ggctctgtgc cgccgctgtc    180
aagggccaga cgggcccaga gcgcccaagc cccttcagtc agctggtcta caccaacaac    240
gactcttacg tgattcacca tggggatctc aggaagatcc acaaagctgc ctcccgggcc    300
aagcctggaa gctggagagg atgatgaaga agacgacaat ggacctgaac ataagagatg    360
cgaagaagag gactgctcta cactgggcct gtgccaatgg ccatgcagaa gtagtaacac    420
ttctggtaga tagaaagtgc cagcttgacg tccttgatgg cgaaaacagg acaactctga    480
tgaaggctct gcaatgccag agggaggctt gtgcaaatat tctcatagat tctggtgctg    540
atccaaatat tgtagatgtg tatggcaaca cagctgtcca ttatgctgtt aacagtgaga    600
atttgtcagt ggtggcaaaa ttgctgtcct gtggtacaga cattaaagtg aagaacaagt    660
tagtgtaaaa ctacaagaaa gtaaaatttg cctgcataaa ttgagtcaac atgtaaaatt    720
taggagacat gcagaaatct ggatttcctc ttaaaggatt gaatcttgtg tctcttgagc    780
ccgtatgact gtttgggctg ccacacacc actttttattg gccataagga aaagaagtga    840
gcaaattgtg gaatttttac tgacaaaaaa tgcaaatgca aatggagttg ataagtttaa    900
atgcattcat caacaacttt tggaatataa acaaagata tctaaaaatt ctcaaaatag    960
taatccagaa ggaacatctg aaggaacacc tgacgaggct gcacccttgg cggaaagaac    1020
acctgacacg gctgaaagct tggtggaaag aacacctgac gaataggata cagtgaattc    1080
ctcttcaaag attttagcct gtaaacatcc tttaaaattc aagagggggg aagattaagt    1140
acaatgagtt ctgagttcct catcaaagaa caaatatgtc agtatgttca gcttctccgt    1200
```

```
tctttgttct ccgttttaaa gtttaacttc ctcgttcgtt atgcctcctt gcccctagtt    1260
tcattaaaca accccttct agcctctaac acctgctttg tctttagtca ttcttagtaa    1320
cctgctctgt ccttagtcat ccttagacac ctgctctgta actgtctttc ccgctgaaac    1380
tactcaccct gccactccag ctcatacccc tgccctcttt gaaatagcca atctgaattg    1440
gcttagagtg tgcagtccaa ccctatccaa tagggaaaag acacaacagt agggactagc    1500
tgcgttagaa ataagaacac tttcccctcc cttgtccggt gtgatcttgc ctttgctcca    1560
tctgcaagac cactcttcca tagaagtaaa tttgccttgc tgtaaaaact tgttgctgga    1620
gtgctgacgg ttcttgtgg caccgaaaat tattttccaa aaatttgagg gcccacccaa    1680
cattcccatt ctcctctggg ggagggtcca gtcctctccc ttgaggaggt gcaccccgct    1740
gcctcgttgc agtggccata aggtaagga atcaagactc aactggtgcg attaataaac    1800
ccgggctctc agcaacgtgg aaagaaacag gccagcaact ctggggaaag gatcttcaca    1860
taccgtggcg accagtgtgc tcttgccatt gctccatccg caagactcac ccttctatag    1920
aagtaaattt gccttgctgg agtgctaact cttctttgtg tcaccaaaaa gttattccca    1980
acatgaaggt gcacccttgg tggagggaac atctgacgaa gttcaatgtt tggggaaagc    2040
aatatctgga aagattgaac agtcagcagg agaaacacct aggaaaatta caaggcctgt    2100
gaaagaaaca tctgagaaat ttgcatggcc acaagaaagg ccttcaaaga ccacacggga    2160
ggaaaaagaa acatctgtaa agactgaatg agtggcagga gtaacattta ataaaattga    2220
agttttggaa gaaggaacat ctaagatgat cacatgtcct acaaaaaaac agctacaaaa    2280
gcaagtacaa atggtatact gttgatgtgg ttgataattc tggtatccaa gaagaaatct    2340
cccaagatcc tacctaactt tttgtaacta agcggcata catacacagg tagtgggaaa    2400
atgtctagag tgattcaact agcctatcaa aaatcttgga tgcagttctt tcttgtgaaa    2460
gagcaaggga acttaaaaaa tatccctgtg ggccaggcgc catggctcac acctgtaatc    2520
tcatcacttt gggaggccaa ggcgggcaga tcatgacgtc aggagatcaa gaccatcctg    2580
gctaacacag tgaaaccccg tctctactaa aaatacaaaa aaaaaatta gccgggcgtg    2640 gtggcaggtg actatagtcc cagctactcg ggaggctgag gcaggagaat ggcatgaacc    2700
cgggaggcgg agcttgcagt gagtggagat cgcgccactg cactccagcc taggcaacag    2760
agcgagactc cgtcaaaaaa aataaaagaa aaaaaaatcc ctgtgaacaa cttacagcaa    2820
aaatgaaaca aatgaaaaat aagcttcgtg tactacaaaa ggaactaaca gaagcaaaat    2880
aaataaaatc atagagaatc aaaaacttaa aagagaacaa gagctctgca gtgtgagatt    2940
gactttaaac caagaagaag agaagagaag aaatgccaat atattaaatg aaaaattagg    3000
gaagaattag gaaaaatcga agagcaacaa aagaaaaagt tagaagtgaa gcaacttgag    3060
ctcactctcc gaatatacaa aatatggaat tgaagactgt aagaagtaat ttgaatcagc    3120
tcaatcaatc gctgggccgc aatctgtcac caaggctagg gtgcagtggc acaatcatgg    3180
atcactgcag cctcaaactc tggggctcaa gcagacctcc tgtctcagcc taccaagtag    3240
ctgggaccac aggccatatg aaatggaggc aatttgttta tcagtctgag tctccagaac    3300
tcctgaattt tttgccaagg aaactggaga aactctcgtc caggtaccaa ccaaggagat    3360
tatttctaca aagaaggaa cagacactga atgactcatt tcccttcctc tcacatgaa    3420 gcagaattag acactcctgc cagcctgacc caagtctgta caggacatcc tgaaatgtct    3480
taaagattcc cgggtgattg tgagaggatt cctagtgacc atggactgat gaccgtatgt    3540
tgatccaggt aggaaagact caagctgatt ataaatagaa aatggaactg ccctggtaca    3600
```

```
gctccagaac ctggatctat gtgtgatatc acctgttctg attagctagg tcttaggtaa    3660
gagaaa                                                                3666

<210> SEQ ID NO 7
<211> LENGTH: 3615
<212> TYPE: DNA
<213> ORGANISM: Homo sapiens

<400> SEQUENCE: 7
ggagaggctg gagtgtccaa aagcttggcc gactgagatt gctagtcgtg tcagggcggg      60
tgcgggactg aagaagggcg agggcgagcg gcggggactg gggaagggcg agcagcggga    120
ggcacgggct ctctctagca ggtggctgca gccatggaga ggctctgtgc cgccgctgtc    180
aagggccaga cgggcccaga gcgcccaagc cccttcagtc agctggtcta caccaacaac    240
gactcttacg tgattcacca tgggatctc aggaagatcc acaaagctgc ctcccgggcc    300
aagcctggaa gctggagagg atgatgaaga agacgacaat ggacctgaac ataagagatg    360
cgaagaagag gactgctcta cactgggcct gtgccaatgg ccatgcagaa gtagtaacac    420
ttctggtaga tagaaagtgc cagcttgacg tccttgatgg cgaaaacagg acaactctga    480
tgaaggctct gcaatgccag agggaggctt gtgcaaatat tctcatagat tctggtgctg    540
atccaaatat tgtagatgtg tatggcaaca cagctgtcca ttatgctgtt aacagtgaga    600
atttgtcagt ggtggcaaaa ttgctgtcct gtggtacaga cattaaagtg aagaacaagc    660
agccacttcc ttagtgaccc atttagagca ggagtgcctg acattggcat ttggaatctt    720
gggatcattg atagaagaga atcaagctgg ccacacacca cttttattgg ccataaggaa    780
aagaagtgag caaattgtgg aattttact gacaaaaaat gcaaatgcaa atggagttga    840
taagtttaaa tgcattcatc aacaactttt ggaatataaa caaagatat ctaaaaattc    900 tcaaaatagt aatccagaag gaacatctga aggaacacct gacgaggctg cacccttggc    960
ggaaagaaca cctgacacgg ctgaaagctt ggtggaaaga cacctgacg aataggatac   1020 agtgaattcc tcttcaaaga ttttagcctg taaacatcct ttaaaattca agaggggggga   1080 agattaagta caatgagttc tgagttcctc atcaaagaac aaatatgtca gtatgttcag   1140
cttctccgtt ctttgttctc cgttttaaag tttaacttcc tcgttcgtta tgcctccttg   1200
cccctagttt cattaaacaa ccccccttcta gcctctaaca cctgctttgt ctttagtcat   1260
tcttagtaac ctgctctgtc cttagtcatc cttagacacc tgctctgtaa ctgtctttcc   1320
cgctgaaact actcacccctg ccactccagc tcatacccct gccctctttg aaatagccaa   1380
tctgaattgg cttagagtgt gcagtccaac cctatccaat agggaaaaga cacaacagta   1440
gggactagct gcgttagaaa taagaacact ttcccctccc ttgtccggtg tgatcttgcc   1500
tttgctccat ctgcaagacc actcttccat agaagtaaat ttgccttgct gtaaaaactt   1560
gttgctggag tgctgacggt tctttgtggc accgaaaatt attttccaaa aatttgaggg   1620
cccacccaac attcccattc tcctctgggg gagggtccag tcctctccct tgaggaggtg   1680
caccccgctg cctcgttgca gtggccataa aggtaaggaa tcaagactca actggtgcga   1740
ttaataaacc cgggctctca gcaacgtgga aagaaacagg ccagcaactc tggggaaagg   1800
atcttcacat accgtggcga ccagtgtgct cttgccattg ctccatccgc aagactcacc   1860
cttctataga agtaaatttg ccttgctgga gtgctaactc ttctttgtgt caccaaaaag   1920
ttatttccaa catgaaggtg cacccttggt ggagggaaca tctgacgaag ttcaatgttt   1980
ggggaaagca atatctggaa agattgaaca gtcagcagga gaaacaccta ggaaaattac   2040
```

```
aaggcctgtg aaagaaacat ctgagaaatt tgcatggcca caagaaaggc cttcaaagac    2100
cacacgggag gaaaaagaaa catctgtaaa gactgaatga gtggcaggag taacatttaa    2160
taaaattgaa gttttggaag aaggaacatc taagatgatc acatgtccta caaaaaaaca    2220
gctacaaaag caagtacaaa tggtatactg ttgatgtggt tgataattct ggtatccaag    2280
aagaaatctc ccaagatcct acctaacttt ttgtaactaa agcggcatac atacacaggt    2340
agtgggaaaa tgtctagagt gattcaacta gcctatcaaa aatcttggat gcagttcttt    2400
cttgtgaaag agcaagggaa cttaaaaaat atccctgtgg gccaggcgcc atggctcaca    2460
cctgtaatct catcactttg ggaggccaag gcgggcagat catgacgtca ggagatcaag    2520
accatcctgg ctaacacagt gaaacccccgt ctctactaaa aatacaaaaa aaaaaattag    2580
ccgggcgtgg tggcaggtga ctatagtccc agctactcgg gaggctgagg caggagaatg    2640
gcatgaaccc gggaggcgga gcttgcagtg agtggagatc gcgccactgc actccagcct    2700
aggcaacaga gcgagactcc gtcaaaaaaa ataaagaaa aaaaaatccc tgtgaacaac    2760
ttacagcaaa aatgaaacaa atgaaaaata agcttcgtgt actacaaaag gaactaacag    2820
aagcaaaata aataaaatca tagagaatca aaaacttaaa agagaacaag agctctgcag    2880
tgtgagattg actttaaacc aagaagaaga gaagagaaga aatgccaata tattaaatga    2940
aaaattaggg aagaattagg aaaaatcgaa gagcaacaaa agaaaaagtt agaagtgaag    3000
caacttgagc tcactctccg aatatacaaa atatggaatt gaagactgta agaagtaatt    3060
tgaatcagct caatcaatcg ctgggccgca atctgtcacc aaggctaggg tgcagtggca    3120
caatcatgga tcactgcagc ctcaaactct ggggctcaag cagacctcct gtctcagcct    3180
accaagtagc tgggaccaca ggccatatga atgaggca atttgtttat cagtctgagt    3240
ctccagaact cctgaatttt ttgccaagga aactggagaa actctcgtcc aggtaccaac    3300
caaggagatt atttctacaa aagaaggaac agacactgaa tgactcattt cccttcctct    3360
cacatggaag cagaattaga cactcctgcc agcctgaccc aagtctgtac aggacatcct    3420
gaaatgtctt aaagattccc gggtgattgt gagaggattc ctagtgacca tggactgatg    3480
accgtatgtt gatccaggta ggaaagactc aagctgatta taaatagaaa atggaactgc    3540
cctggtacag ctccagaacc tggatctatg tgtgatatca cctgttctga ttagctaggt    3600
cttaggtaag agaaa                                                    3615

<210> SEQ ID NO 8
<211> LENGTH: 3529
<212> TYPE: DNA
<213> ORGANISM: Homo sapiens

<400> SEQUENCE: 8
ggagaggctg gagtgtccaa aagcttggcc gactgagatt gctagtcgtg tcagggcggg     60
tgcgggactg aagaagggcg agggcgagcg gcggggactg gggaagggcg agcagcggga    120
ggcacgggct ctctctagca ggtggctgca gccatggaga ggctctgtgc cgccgctgtc    180
aagggccaga cgggcccaga gcgcccaagc cccttcagtc agctggtcta caccaacaac    240
gactcttacg tgattcacca tgggatctc aggaagatcc acaaagctgc ctcccgggcc    300
aagcctggaa gctggagagg atgatgaaga agacgacaat ggacctgaac ataagagatg    360
cgaagaagag gactgctcta cactgggcct gtgccaatgg ccatgcagaa gtagtaacac    420
ttctggtaga tagaaagtgc cagcttgacg tccttgatgg cgaaaacagg acaactctga    480
tgaaggctct gcaatgccag agggaggctt gtgcaaatat tctcatagat tctggtgctg    540
```

```
atccaaatat tgtagatgtg tatggcaaca cagctgtcca ttatgctgtt aacagtgaga    600
atttgtcagt ggtggcaaaa ttgctgtcct gtggtacaga cattaaagtg aagaacaagg    660
ctggccacac accactttta ttggccataa ggaaaagaag tgagcaaatt gtggaatttt    720
tactgacaaa aaatgcaaat gcaaatggag ttgataagtt taaatgcatt catcaacaac    780
ttttggaata taaacaaaag atatctaaaa attctcaaaa tagtaatcca gaaggaacat    840
ctgaaggaac acctgacgag gctgcaccct tggcggaaag aacacctgac acggctgaaa    900
gcttggtgga agaacacct gacgaatagg atacagtgaa ttcctcttca aagattttag     960
cctgtaaaca tcctttaaaa ttcaagaggg gggaagatta agtacaatga gttctgagtt   1020
cctcatcaaa gaacaaatat gtcagtatgt tcagcttctc cgttctttgt tctccgtttt   1080
aaagtttaac ttcctcgttc gttatgcctc cttgccccta gtttcattaa caaccccct    1140 tctagcctct aacacctgct ttgtctttag tcattcttag taacctgctc tgtccttagt   1200
catccttaga cacctgctct gtaactgtct ttcccgctga aactactcac cctgccactc   1260
cagctcatac ccctgccctc tttgaaatag ccaatctgaa ttggcttaga gtgtgcagtc   1320
caaccctatc caatagggaa aagacacaac agtagggact agctgcgtta gaataagaa    1380 cactttcccc tccttgtcc ggtgtgatct tgcctttgct ccatctgcaa gaccactctt   1440
ccatagaagt aaatttgcct tgctgtaaaa acttgttgct ggagtgctga cggttctttg   1500

tggcaccgaa aattatttct caaaaatttg agggcccacc caacattccc attctcctct   1560
gggggagggt ccagtcctct cccttgagga ggtgcacccc gctgcctcgt tgcagtggcc   1620
ataaaggtaa ggaatcaaga ctcaactggt gcgattaata aacccgggct ctcagcaacg   1680
tggaaagaaa caggccagca actctgggga aaggatcttc acataccgtg gcgaccagtg   1740

tgctcttgcc attgctccat ccgcaagact cacccttcta tagaagtaaa tttgccttgc   1800

tggagtgcta actcttcttt gtgtcaccaa aaagttattt ccaacatgaa ggtgcaccct   1860

tggtggaggg aacatctgac gaagttcaat gtttgggaa agcaatatct ggaaagattg    1920
aacagtcagc aggagaaaca cctaggaaaa ttacaaggcc tgtgaaagaa acatctgaga   1980
aatttgcatg ccacaagaa aggccttcaa agaccacacg ggaggaaaaa gaaacatctg   2040

taaagactga atgagtggca ggagtaacat ttaataaaat tgaagttttg gaagaaggaa   2100
catctaagat gatcacatgt cctacaaaaa aacagctaca aaagcaagta caaatggtat   2160
actgttgatg tggttgataa ttctggtatc caagaagaaa tctcccaaga tcctacctaa   2220 cттттттgтaa ctaaagcggc atacatacac aggtagtggg aaaatgtcta gagtgattca   2280
actagcctat caaaatctt ggatgcagtt ctttcttgtg aaagagcaag gaacttaaa    2340 aaatatccct gtgggccagg cgccatggct cacacctgta atctcatcac tttgggaggc   2400
caaggcgggc agatcatgac gtcaggagat caagaccatc ctggctaaca cagtgaaacc   2460
ccgtctctac taaaaataca aaaaaaaaaa ttagccgggc gtggtggcag gtgactatag   2520

tcccagctac tcgggaggct gaggcaggag aatggcatga acccgggagg cggagcttgc   2580
agtgagtgga gatcgcgcca ctgcactcca gcctaggcaa cagagcgaga ctccgtcaaa   2640
aaaaataaaa gaaaaaaaaa tccctgtgaa caacttacag caaaaatgaa acaaatgaaa   2700
aataagcttc gtgtactaca aaaggaacta acagaagcaa ataaataaa atcatagaga   2760 atcaaaaact taaaagagaa caagagctct gcagtgtgag attgacctta aaccaagaag   2820
aagagaagag aagaaatgcc aatatattaa atgaaaaatt agggaagaat taggaaaaat   2880
cgaagagcaa caaaagaaaa agttagaagt gaagcaactt gagctcactc tccgaatata   2940
```

| | |
|---|---|
| caaaatatgg aattgaagac tgtaagaagt aatttgaatc agctcaatca atcgctgggc | 3000 |
| cgcaatctgt caccaaggct agggtgcagt ggcacaatca tggatcactg cagcctcaaa | 3060 |
| ctctggggct caagcagacc tcctgtctca gcctaccaag tagctgggac cacaggccat | 3120 |
| atgaaatgga ggcaatttgt ttatcagtct gagtctccag aactcctgaa ttttttgcca | 3180 |
| aggaaactgg agaaactctc gtccaggtac caaccaagga gattatttct acaaaagaag | 3240 |
| gaacagacac tgaatgactc atttcccttc ctctcacatg gaagcagaat tagacactcc | 3300 |
| tgccagcctg acccaagtct gtacaggaca tcctgaaatg tcttaaagat tcccgggtga | 3360 |
| ttgtgagagg attcctagtg accatggact gatgaccgta tgttgatcca ggtaggaaag | 3420 |
| actcaagctg attataaata gaaaatggaa ctgccctggt acagctccag aacctggatc | 3480 |
| tatgtgtgat atcacctgtt ctgattagct aggtcttagg taagagaaa | 3529 |

```
<210> SEQ ID NO 9
<211> LENGTH: 3923
<212> TYPE: DNA
<213> ORGANISM: Homo sapiens

<400> SEQUENCE: 9
```

| | |
|---|---|
| ggagaggttg gagtgtccaa aagcttggcc cgactgagat ttctagtctt gtcagggcgg | 60 |
| atgcagggac tgaagaaggg cgagggcgag cggcgggac tggggaaggg cgagcagcgg | 120 |
| gaggcacggg ctctctctag caggtggctg cagccatgga gaggctctct gccgcccctg | 180 |
| tcaagggcca gacgggccca gagcgcccga gccccttcag tcagctggtc tacaccaaca | 240 |
| acgactctta cgtgattcac catggggatc tcaggaagat ccacaaagct gcctcccggg | 300 |
| gccaagcctg gaagctggag aggatgatga agaagacgac aatggacctg aacataagag | 360 |
| atgcgaagaa gaggactgct ctatactggg cctgtgccaa tggccatgca gaagtagtaa | 420 |
| cacttctggt agatagaaag tgtcagcttg acgtccttga tggtgaaaac aggaccattc | 480 |
| tgatgaaggc tctgcaatgc cagagggagg cttgtgcaaa tattctcata gattctggtg | 540 |
| ctgatccaaa tattgtagat gtgtatggca acacagctgt ccattatgct gttaacagtg | 600 |
| agaatttgtc agtggtggca aaattgctgt cctgtggtgc agacatcgaa gtgaagaaca | 660 |
| agttagtgta aaactacagg aaagtaaaat ttgcctgcat aaattgagtc aacatgtaaa | 720 |
| atttaggaga catgcagaaa tctggatttc ctcttaaagg attgaatctt gtgtcttttg | 780 |
| agcccgtatg actgtttgag ccacttcctt agtgacccat ttagagcagg agtgcctgac | 840 |
| attggcattt ggaatcttgg aatcattgat agaagagaat caagctggcc acacaccact | 900 |
| tttactggcc ataaggaaaa gaagtgagga aattgtggaa ttttttactga caaaaaatgc | 960 |
| aaatgcaaat gcagttgata agtttaaatg cacagccctc atgcttgcca tatgtcatgg | 1020 |
| atcatcagag atagttggca agcttcttca gcaaaatgtt gacatctgtg ctgaagctac | 1080 |
| atgtggaatg attgcagaac gttatgctgt tgcttgtgga tttaatctct aagtgtttac | 1140 |
| atttaaaggc tagcgttcat caacaacttt tggaatataa acaaaagata tctaaaaatt | 1200 |
| ctcaaaatag taatccagaa ggaacatctg aaggaacacc tgatgaggct gcacccttgg | 1260 |
| cggaaagaac acctgacacg gctgaaagct tggtggaaag aacacctgat gaataggata | 1320 |
| cagtgaattc ctcttcaaag attttagcct gtaaacatcc tttaaaattc aagaggggga | 1380 |
| agattaagta caatgagttc tgagttcctc atcaaagaac aaatatgtca gtatgttcag | 1440 |
| cttctctgtt ctttgttctc cgtttttaaag tttaacttcc tcgttcgtta tgcctccttg | 1500 |
| cccctagttt cattaaacag ccccccttcta gcctctaaca cctgctttgt ctttagtcat | 1560 |

```
tcttagtaac ctgctctgtc cttagtcatc cttagacacc tgctctgtaa ctgtctttcc    1620
cgctgaaact actcaccctg ccactccagc tcatacccct gccctcttta aatagccaat    1680
ctgaattggc ttagagtgtg cagtccaacc ctatccaata gggaaaagac acaacagtag    1740
ggactagctg cgttagaaat aagaacactt tcccctccct tgtccggtgt gatcttgcca    1800
ttgctccatc tgcaagacca ctcttccata gaagtaaatt tgccttgctg taaaaacttg    1860
ttgctggagt gctgacggtt ctttgcggcg ctgaaaattt attttccaca aatttaaggg    1920
cccacccagc attcccattc tcctctaggg gagggtccag tcctctccct tgaggaggcg    1980
caccccgctg cctcgttgca gtggccataa aggtaaggaa tcaagactca actggtgcga    2040
ttaataaacc cgggctctca gcaacgtgga aagaaacagg ccagcaactt tggggaaagg    2100
atcttcacat accgtggcga ccagtgtgct cttgccattg ctccatccgc aagactcagc    2160
cttctataga agtaaatttg ccttgctgga agtgctaact cttctttgtg tcaccaaaaa    2220
gttatttcca acatgaagct gcacccttgg tagagggaac atctgacgaa gttcaatgtt    2280
tggggaaagc aatatctgga aagattgaac agtcagcagg agaaacacct aggaaaatta    2340
caaggcctgt gaacgaaaca tctgagaaat ttgcatggcc acgagaaaga cctacaaaga    2400
ccacatggaa ggaaaaagaa acatctgtaa agactgaatg agtggcagga gtaacatcta    2460
ataaaattga agttttggaa gaaggaacat ctaagatgat cacatgtcct ataaaaaaaa    2520
cagctacaaa agcaagtaca aatggtatac tgttgatgtg gttgataatt ctggtatcca    2580
agaagaaatc tcccaagatc ctacctaact ttttgtaact aaagcagcat acatacagag    2640
gtagtgggaa aatgtctaga ctgattcaac tagcctatca aaaatcttgg atgcagttct    2700
ttcttgtgaa agagcaaggg aacttaaaaa atatccctgt gggccaggcg ccatggctca    2760
tgcctgtaat ctcatcactt tgggaggcca aggcgggcag atcatgaggt caggagatca    2820
agaccatcct ggctaacaca gtgaaacccc gtctctacta aaaatacaaa aaaaattag    2880 ctggccgtag tggcaggtga cagtagtccc agctactcgg gaagctgagt caggagaatg    2940
gcatgaaccc gggaggcgga gcttgcagtg agtggagatc gcgccactgc actccagcct    3000
aggcaacaga gcgagactcc gtcgaaaaaa agaaaaaaaa aaagaaaaa aaatccctgt    3060 gaacaactta cagcaaaaat gaaacaaatg aaaaataagc ttcgtgtact acaaaaggaa    3120
ctaacagaag caaagaaat aaaatcatag agaatcaaaa agttaaaaga gaacaagagc    3180
tctgcactgt gagattgact ttaaaccaag aagaagagaa gagaagaaat gccaatatat    3240
taaatgaaaa aattagggaa gaattaggaa aaatcgaaga gcaacaaaag aaaaagttag    3300
aagtgaagca acttgaactc actctccgaa tatacaaaat atggaattga agactgtaag    3360
aagtaatttg aatcagctca atcaatcgct gggctgcaat ctgtcaccaa ggctggggtg    3420
cagtggcaca atcatggatc actgcagcct caaactctgg ggctcaagca gacctcctgt    3480
ctcagcctca caagtagctg ggaccacagg ccatatgaaa tggaggcaat tgtttatca    3540 gtctgagtct ccagaactcc tgaattttt gccaaggaaa ctggagaaac tctcgtccag    3600
gtaccaacca aggagattat ttctacaaaa gaaggaacag acactgaatg actcatttcc    3660
cttcctctaa catggaagca gaattagaca ctcctgccag cctgacccaa gtgtgtacag    3720
gacatcctga aatgtcttaa agattcccgg gtgattgtga gaggattcct agtgaccatg    3780
gactgatgac cacatgttga tccaggtagg aaagactcaa gctgattcta catagaaaat    3840
ggaactgccc tggtacagct ccagaacctg gatctatgtg tgatatcacc tgttctgatt    3900
agctaggtct taggtaagag aaa                                            3923
```

<210> SEQ ID NO 10
<211> LENGTH: 3938
<212> TYPE: DNA
<213> ORGANISM: Homo sapiens

<400> SEQUENCE: 10

| | | | | | | |
|---|---|---|---|---|---|---|
| ggtgaggctg | gagtgtccaa | aagcttggcc | cgactgagat | ttctactggt | gtcagggcgg | 60 |
| gtgcggggac | tgaagaaggg | caagggcgag | cggcgggac | tgggaaaggg | cgagcagcgg | 120 |
| gaggtgcggg | cgctctctag | caggtggctg | cagccatgga | gaggctctct | gccgccgctg | 180 |
| tcaagggcca | gacgggcctg | gagtgcccga | gccccttcag | tcagctggtc | tacaccaata | 240 |
| atgactctta | agtgattcac | catggggatc | tcaggaagat | ccacaaagct | gcctcccggg | 300 |
| gccaagcctg | gaagctggag | aggatgatga | agaaaacgac | aatggacccg | aacataagag | 360 |
| atgcgaagaa | gaggactgca | ctacactggg | cctgtgccaa | tggccatgca | gaagtagtaa | 420 |
| cacttctggt | agatagaaag | tgccagcttg | acgtccttga | tggtgaaaac | gggacacctc | 480 |
| tgatgaaggc | tgtgcaatgc | cagagggaag | tttgtgcaaa | tattctcata | gattctggtg | 540 |
| ctgatccaaa | tattgtagat | gtgtatgtca | acacagctgt | ccattatgct | gtttatggtg | 600 |
| agaatttgtc | agtggtggca | aaattgctgt | cctgtggtgc | agacatcaaa | gtgaagaaca | 660 |
| agttagcata | aaactacagg | aaagtaaaat | ttgcctgcat | aaattgagtc | aacatgtaaa | 720 |
| atttaggaga | catgcagaaa | tctggatttc | ctcttaaagg | attgaatctg | gtgtctcttg | 780 |
| agcctgtatg | actgtttgag | ccacttcctt | agtgacccat | ttagagcagg | agtgcctgac | 840 |
| attgtcatct | ggaatcttgg | gatcattgag | agaagagaat | caagctggcc | acacaccact | 900 |
| tttactggcc | ataaggaaaa | gaagtgagca | aattgtggaa | ttttactga | caaaaaatgc | 960 |
| aaatgcaaat | gcaaattcag | ttgataagtt | taaatgcaca | gccctcatgc | ttgccatatg | 1020 |
| tcatggatca | tcagagatag | ttggcatggt | tcttcagcaa | aatgttgaca | tctgtgctgt | 1080 |
| agatacgtgt | ggaatgattg | cagaacgtta | tgctgttgct | tgtggattta | atctgtaagt | 1140 |
| gtttacattt | aaaggttagg | cattcatcaa | caacttttgg | aatacaaaca | aaagatatct | 1200 |
| aaaaattctc | aaaataacaa | tccagaagga | acatctgaag | gaacacctga | cgaggctgca | 1260 |
| cccttgacag | aaagaacacc | tgacatggct | gaaagcttgg | tggaaagaac | acctgacgaa | 1320 |
| taggatacag | tgaattcatc | ttcaaagatt | ttagcctgta | aaaatccttt | aaaattcaag | 1380 |
| agggggaaga | ttaagtacag | tgagttctga | gttcctcatc | aaaaaaaaaa | tatgtcagta | 1440 |
| tgtccagctt | ctctgttctt | ttttctccgt | tttaaagttt | aacttcctcg | ttcgttatgc | 1500 |
| ctccttgccc | ctagtttcat | taaacaaccc | cctcctagcc | tctaaccct | gctttgtctt | 1560 |
| tagtcattct | tagtcacctg | ctctgtcctt | agtcatcctt | agacacctgc | tctgtaactg | 1620 |
| gctttcccgc | tgaaactact | cacccctgcca | ctccagctta | taccoctact | ctcttgaaa | 1680 |
| tagccaatct | gaattagctt | agagtgtgca | gtccaaccct | atccaatagg | gaaaagacac | 1740 |
| aacagtaggg | actagctgtg | ttaggaataa | gaacactttc | ccctcccttg | tccggtgtga | 1800 |
| tcttgccatt | gctccatctg | caagaccact | cttccataga | agtaattttg | ccttgctgta | 1860 |
| aaaacttgtg | gctggagtgc | tgactgttct | ttgtggcacc | aaaaatttat | tttccacaaa | 1920 |
| tttgggggcc | cacccagcat | tcccattctc | ctctggggga | gggtccagtc | ctctcccatg | 1980 |
| aggaggcgca | ccccgctgcc | ttgttgcagt | ggccataaag | gtaaggaatc | aagactcaac | 2040 |
| tggtgcgatt | aataaacctg | ggctctcagc | aacgtgaaa | gaaacaggcc | agcatctttg | 2100 |
| gggaaaggat | cttcacatgc | cgtggtgacc | agtgtgctct | tgccattgct | ccatcctcaa | 2160 |

```
gactcaccct tctatagaag taaatttgcc ttgctggatg ctaactcttc tttgtggcac    2220
caaaaagtta tttccaacac gaagctgcac ccttggagga gggaacatct gacgaagttc    2280
aatgcttggg gaaaacaata tctggaaaga ttgaacagtc agcaggagaa acacctagga    2340
aaattacaag acctgtgaaa aaaaatctga gaaatttgca tggccacaag aaagacctac    2400
aaagaccaca tgtgaggaag aagaaacatc tgtaaagact gaatgcgtgg caggagtaac    2460
atctaataaa attgaagttt tggaagaagg aacatctaag atgatcacat gtcctacaaa    2520
aaaacagcta caaagcaag tacaaatggt atacttttga tgtgattgat atttctggta    2580
tccaagaaga aatctcccaa gatcctacct aacttttgt aactaaagca gcatacatac    2640
acagggagtg ggaaaatgtc tagactgatt caactagcct atcaaaaatc ttggatgcag    2700
ttctttcttg tgaaagagca agggaactta aaaaatatcc ctgtgagcca ggtgctgtgg    2760
ctcatgcctg taatcccatc actttgggag gccaaggcgg gcagatcatg aggtcaggag    2820
atcaagacca tccttgctaa cacagtgaaa ccccgtctct actaaaaata caaaaaaaaa    2880
tattagccgg gcatgctggc gggtgcctgt agtcccagct actcaggagg ctgaggcagg    2940
agaatggcgt gaacccagga ggtggagctt gcagtgagtg gagaacccac cactgcactc    3000
cagcctaggc aacagagaga gactccgtca aaaaaaaaa aaaaagaaa aagaaaaaa    3060 aagaaaaaaa atccctgtga caacttaca gcaaaaatga aacaaatgaa aataagctt    3120 cgtgtactac aaaatgaact atcagaacca aagaaataa atcatagag aatcaaaaag    3180 ttaaaagaga acaagagctc tgcagtctga gattgacttt aaaacaagaa taagagaaga    3240
aatgccaata tattaaaaga aaaaatagga aagaattagg aaaattcgaa gagctgcaaa    3300
agaaaaagtt agaagtgaag caacttgaac tcgctctccg aatatacaag atatggaatt    3360
gaagatggta agaagtaatt tgaatcagct caatcaatcg ctgacacggt ctcactctgt    3420
caccaaggct ggggtgcagt ggcacaatca tggatcactg cagcctcaaa ctctgggct    3480 caaacagacc gcctgtctca gcctccctag tagctgggac tataggccat atgaaatgga    3540
ggcaatttgt ttatcagtct gagtctccag aactcctgaa ttttttgcca aggaaactgg    3600
agaaactctc atccgggtac caaccaagga gattctttct acaaaagaag gaacagacat    3660
gaatgactca cttcccttcc tctaacatgg aagcagaatt agacactcct gccagcctga    3720
cccaagtctg tacaggatat cctgaaatgt tttaaagatt cccggatgat tgtgagagga    3780
ttcctagtga ccatggactg atgacccat gatgatccag gcaggaaaga ctcaagctga    3840
ctctaaatag aaaatggaac tgccctggta tagctccaga acctggatct acatgtgata    3900
tcacctgttc tgattagcta gctcttaggt aagagaaa                           3938
```

<210> SEQ ID NO 11
<211> LENGTH: 3907
<212> TYPE: DNA
<213> ORGANISM: Homo sapiens

<400> SEQUENCE: 11

```
ggagaggctg gagtgtccaa aagcttggcc gactgagatt tctagtcgtg tcagggcggg     60
tgcagggact gaagaagggc aaggggcgag tggcgggac tggggaaggg cgagcagcgg    120
gaggcacggg ctctctctag caggtggctg cagccatgga gaggctctgt gccaccgctg    180
tcaagggcca gacgggccca gagcgcccaa gccccttcag tcagctgttc tacaccaaca    240
acgactctta cgtgattcac catgggggatc tcaggaagat ccacaaagct gcctcccggg    300
ccaagcctgg aagctggaga ggatgatgaa gaagacgaca atggacctga acataagaga    360
```

```
tgcgaagaag aggactgctc tacactgggc ctgtgccaat ggccatgcag aagtagtaac    420
acttctggca gatagaaagt accagcttga cgtccttgat ggtgaaaaca ggacaactct    480
gatgaaggct ctgcaatgcc agagggaggc ttgtgcaaat attctcatag attctggtgc    540
tgatccaaat attgtaggtg tgtatggcaa cacagctgtc cattatgctg ttaacagtga    600
gaatttgtca gtggtggcaa aattgctgtc ctgtggtgca gacattgaat tgaagaacaa    660
gttagtgtaa aactacaaga aagtaaaatt tgcctgcata aattgagtca acatgtaaaa    720
tttaggagac atgcagaaat ctggatttcc tcttaaagga ttgaatcttg agcccgtata    780
actgtttgag ccacttcctt agtgactcat ttagagcagg agtgcctgac attggcattt    840
ggaatcttgg gatcattgat agaagagaat caagctggcc acacaccact tttattggcc    900
ataaggaaaa gaagtgagca aattgtggaa ttttttactga caaaaaatgc aaatgcaatt    960
gcagttgata agtttaaatg cacagccctc atgcttgcca tatgtcatgg atcatcagag   1020
atagttggca tggttcttca gcaaaatgtt gacatctgtg ctgaagctac atgtggaatg   1080
attgcagaac gttatgctgt tgcttgtgga tttaatctct aagtgtttac atttaaaggc   1140
tagcattcat caacaacttt tggaatataa acaaaagata tctaaaaatt ctcaaaatag   1200
taatccagaa ggaacatctg aaggaacact tgatgaggct gcacccttgg cagaaagaac   1260
acctgacacg gctgaaagct tggtggaaag aacacctgat gaataggata cagtgaattc   1320
ctcttcaaag attttagcct gtaaatatcc tttaaaattc aagaggggga agattaagta   1380
caatgagttc tgagttcctc atcaaagaac aaatatgtca gtatgttcag cttctctgtt   1440
ctttgttctc cgttttaaag tttaacttcc tcgttcgtta tgcctccttg ccctagtt   1500 cattaaacaa ccccccttcta gcctctaaca cctgctttgt ctttagtcat tcttagtaac   1560
ctgctctgtc cttagtcatc cttagacacc tgctctgtaa ctgtctttcc cactgaaact   1620
actcaccctg ccactccagc tcatacccct gccctctttg aaatagccaa tctgaattgg   1680
cttagagtgt gcagtccaac cctatccaat agggaaaaga cacaacagta gggactagct   1740
gagttagaaa taagaacact ttcccctccc ttgtctggtg tgatcttgcc tttgctccat   1800
ctgcaagacc actcttccat agaagtaaat ttgccttgct gtaaaaactt gttgctggag   1860
tgctgacggt tctttgcggc aacgaaaatt attttccaca aatttgaggg cccacccagc   1920
attcccattc tcctctgggg gagggtccag tcctctccct tgaggaggcg caccccgctg   1980
cctcgttgca gtggccataa aggtaaggaa tcaagactca actggtgcga ttaataaatc   2040
cgggctctca gcaacgtgga aagaaacaga ccagcaactt tggggaaagg atcttcacat   2100
accgtggcga ccagtatgct cttgccattg ctccatccgc aagactcacc tttctataga   2160
agtaaatttg ccttgctgga gtgctaactc ttctttgtgt catcaaaaag ttatttccaa   2220
catgaagctg cacccttggt ggagggaaca tctgacgaag ttcaatgttt ggggaaagca   2280
atatctggaa agattgaaca gtcagcagga gaaacaccta ggaaaattac aaggcctgtg   2340
aaagaaacat ctgagaaatt tgcatggcca caagaaagac cttcaagac cacacaggag   2400 gaaaagaaa catctgtaaa gactgaatga gtggcaggag taacatctaa taaaattgaa   2460
gttttggaag aaggaacatc taagatgatc acatgtccta caaaaaaaca gctacaaaag   2520
caagtacaaa tggtatactg ttgatgtggt tgataattct ggtatccaag aagaaatctc   2580
ccaagatcct acctaacttt ttgtaactaa agcggcatac atacacaggt agtgggaaaa   2640
tgtctagagt gattcaacta gcctatcaaa aatcttggat gcagttattt cttgtgaaag   2700
agcaagggaa cttaaaaaat atccctgtgg gccaggcgcc atggctcacg cctgtaatct   2760
```

```
catcactttg ggaggccaag gcgggcagat catgaggtca ggagatcaag accatcctgg    2820
ctaacacagc gaaaccccgt ctctactaaa aatacaaaaa aaaaaaaaaa ttagccaggc    2880
gtggtggcag gtgactgtag tcccagctac tcgggaggct gaggcaggag aatggcatga    2940
acccgggagg cagagcttgc agtgagtgga gatcgcacca ctgcactcca gcctaggcaa    3000
cagagcaaga ctccgtcaaa aaaaaaaaa agaaaaaaa aatccctgtg aacaacttac      3060
agcaaaaatg aaacaaatga aaataagct tcgtgtacta cagaaggaac taacagaagc     3120
aaaagaaata aaatcataga gaatcaaaaa cttaaaagag aacaagagct ctgcagtgtg    3180
agattgactt taaaccaaga agaagagaag aaatgccaat atattaaatg aaaaaattag    3240
ggaagaatta ggaaaaatcg aagagcaaca aagaaaaag ttagaagtga agcaacttga     3300
actcactctc cgaatataca aaatatggaa ttgaagactg taagaagtaa tttgaatcag    3360
ctcaatcaat cgctgggccg caatctgtaa ccaaggctgg ggtgcagtgg cacaatcatg    3420
gatcactgca gcctcaaact ctggggctca agcagacctc ctgtctcagc ctcccaagta    3480
gctgggacca caggccatat gaaatggagg caatttgttt atcagtctga gtctccagaa    3540
ctcctgaatt ttttgccaag gaaactggag aaactcttgt ccaggtacca accaaggaga    3600
ttatttctac aaaagaagga acagacactg aatgactcat ttcccttcct ctaacatgga    3660
agcagaatta gacactcctg ccagcctgac ccaagtctgt acaggacatc ctgaaatgtc    3720
ttaaagattc ccgggtgatt gtgagaggat cctagtgac catggactga tgaccatatg     3780
ttgatccatg taggaaagac tcaagctgat tctaaataga aaatgaaact gccctggtac    3840
agctccagaa cctggatcta tgagtgatat cacctgttct gattagctag gtcttaggta    3900
agagaaa                                                              3907

<210> SEQ ID NO 12
<211> LENGTH: 579
<212> TYPE: DNA
<213> ORGANISM: Homo sapiens

<400> SEQUENCE: 12
gcaatgccag agggaggctt gtgcaaatat tctcatagat tctggtgctg atccaaatat      60
tgtagatgtg tatggcaaca cagctgtcca ttatgctgtt aacagtgaga atttgtcagt     120
ggtggcaaaa ttgctgtcct gtggtacaga cattaaagtg aagaacaagg ctggccacac    180
accactttta ttggccataa ggaaaagaag tgagcaaatt gtggaatttt tactgacaaa    240
aaaatgcaaa tgcaaatgga gttgataagt ttaaatgcat tcatcaacaa cttttggaat    300
ataaacaaaa gatatctaaa aattctcaaa atagtaatcc agaaggaaca tctgaaggaa    360
cacctgacga ggctgcaccc ttggcggaaa gaacacctga cacggctgaa agcttggtgg    420
aaagaacacc tgacgaatag gatacagtga attcctcttc aaagatttta gcctgtaaac    480
atcctttaaa attcaagagg ggggaagatt aagtacaatg agttctgagt tcctcatcaa    540
agaacaaata tgtcagtaaa aaaaaaaaa aaaaaaaa                             579

<210> SEQ ID NO 13
<211> LENGTH: 115
<212> TYPE: PRT
<213> ORGANISM: Homo sapiens

<400> SEQUENCE: 13

Met Met Lys Lys Thr Thr Met Asp Leu Asn Ile Arg Asp Ala Lys Lys
 1               5                  10                  15
```

Arg Thr Ala Leu His Trp Ala Cys Ala Asn Gly His Ala Glu Val Val
            20                  25                  30

Thr Leu Leu Val Asp Arg Lys Cys Gln Leu Asp Val Leu Asp Gly Glu
        35                  40                  45

Asn Arg Thr Thr Leu Met Lys Ala Leu Gln Cys Gln Arg Glu Ala Cys
 50                  55                  60

Ala Asn Ile Leu Ile Asp Ser Gly Ala Asp Pro Asn Ile Val Asp Val
 65                  70                  75                  80

Tyr Gly Asn Thr Ala Val His Tyr Ala Val Asn Ser Glu Asn Leu Ser
                85                  90                  95

Val Val Ala Lys Leu Leu Ser Cys Gly Thr Asp Ile Lys Val Lys Asn
            100                 105                 110

Lys Leu Val
        115

<210> SEQ ID NO 14
<211> LENGTH: 115
<212> TYPE: PRT
<213> ORGANISM: Homo sapiens

<400> SEQUENCE: 14

Met Met Lys Lys Thr Thr Met Asp Leu Asn Ile Arg Asp Ala Lys Lys
 1               5                  10                  15

Arg Thr Ala Leu His Trp Ala Cys Ala Asn Gly His Ala Glu Val Val
            20                  25                  30

Thr Leu Leu Val Asp Arg Lys Cys Gln Leu Asp Val Leu Asp Gly Glu
        35                  40                  45

Asn Arg Thr Thr Leu Met Lys Ala Leu Gln Cys Gln Arg Glu Ala Cys
 50                  55                  60

Ala Asn Ile Leu Ile Asp Ser Gly Ala Asp Pro Asn Ile Val Asp Val
 65                  70                  75                  80

Tyr Gly Asn Thr Ala Val His Tyr Ala Val Asn Ser Glu Asn Leu Ser
                85                  90                  95

Val Val Ala Lys Leu Leu Ser Cys Gly Thr Asp Ile Lys Val Lys Asn
            100                 105                 110

Lys Leu Val
        115

<210> SEQ ID NO 15
<211> LENGTH: 117
<212> TYPE: PRT
<213> ORGANISM: Homo sapiens

<400> SEQUENCE: 15

Met Met Lys Lys Thr Thr Met Asp Leu Asn Ile Arg Asp Ala Lys Lys
 1               5                  10                  15

Arg Thr Ala Leu His Trp Ala Cys Ala Asn Gly His Ala Glu Val Val
            20                  25                  30

Thr Leu Leu Val Asp Arg Lys Cys Gln Leu Asp Val Leu Asp Gly Glu
        35                  40                  45

Asn Arg Thr Thr Leu Met Lys Ala Leu Gln Cys Gln Arg Glu Ala Cys
 50                  55                  60

Ala Asn Ile Leu Ile Asp Ser Gly Ala Asp Pro Asn Ile Val Asp Val
 65                  70                  75                  80

Tyr Gly Asn Thr Ala Val His Tyr Ala Val Asn Ser Glu Asn Leu Ser
                85                  90                  95

Val Val Ala Lys Leu Leu Ser Cys Gly Thr Asp Ile Lys Val Lys Asn

Lys Gln Pro Leu Pro
        115

<210> SEQ ID NO 16
<211> LENGTH: 115
<212> TYPE: PRT
<213> ORGANISM: Homo sapiens

<400> SEQUENCE: 16

Met Met Lys Lys Thr Thr Met Asp Leu Asn Ile Arg Asp Ala Lys Lys
1               5                   10                  15

Arg Thr Ala Leu His Trp Ala Cys Ala Asn Gly His Ala Glu Val Val
            20                  25                  30

Thr Leu Leu Val Asp Arg Lys Cys Gln Leu Asp Val Leu Asp Gly Glu
        35                  40                  45

Asn Arg Thr Thr Leu Met Lys Ala Leu Gln Cys Gln Arg Glu Ala Cys
    50                  55                  60

Ala Asn Ile Leu Ile Asp Ser Gly Ala Asp Pro Asn Ile Val Asp Val
65                  70                  75                  80

Tyr Gly Asn Thr Ala Val His Tyr Ala Val Asn Ser Glu Asn Leu Ser
                85                  90                  95

Val Val Ala Lys Leu Leu Ser Cys Gly Thr Asp Ile Lys Val Lys Asn
            100                 105                 110

Lys Leu Val
        115

<210> SEQ ID NO 17
<211> LENGTH: 195
<212> TYPE: PRT
<213> ORGANISM: Homo sapiens

<400> SEQUENCE: 17

Met Met Lys Lys Thr Thr Met Asp Leu Asn Ile Arg Asp Ala Lys Lys
1               5                   10                  15

Arg Thr Ala Leu His Trp Ala Cys Ala Asn Gly His Ala Glu Val Val
            20                  25                  30

Thr Leu Leu Val Asp Arg Lys Cys Gln Leu Asp Val Leu Asp Gly Glu
        35                  40                  45

Asn Arg Thr Thr Leu Met Lys Ala Leu Gln Cys Gln Arg Glu Ala Cys
    50                  55                  60

Ala Asn Ile Leu Ile Asp Ser Gly Ala Asp Pro Asn Ile Val Asp Val
65                  70                  75                  80

Tyr Gly Asn Thr Ala Val His Tyr Ala Val Asn Ser Glu Asn Leu Ser
                85                  90                  95

Val Val Ala Lys Leu Leu Ser Cys Gly Thr Asp Ile Lys Val Lys Asn
            100                 105                 110

Lys Ala Gly His Thr Pro Leu Leu Ala Ile Arg Lys Arg Ser Glu
        115                 120                 125

Gln Ile Val Glu Phe Leu Leu Thr Lys Asn Ala Asn Ala Asn Gly Val
    130                 135                 140

Asp Lys Phe Lys Cys Thr Ala Leu Met Leu Ala Ile Cys His Gly Ser
145                 150                 155                 160

Ser Glu Ile Val Gly Lys Leu Leu Gln Gln Asn Val Asp Ile Cys Ala
                165                 170                 175

Glu Ala Thr Cys Gly Met Ile Ala Glu Arg Tyr Ala Val Ala Cys Gly
            180                 185                 190

Phe Asn Leu
        195

<210> SEQ ID NO 18
<211> LENGTH: 115
<212> TYPE: PRT
<213> ORGANISM: Homo sapiens

<400> SEQUENCE: 18

Met Met Lys Lys Thr Thr Met Asp Leu Asn Ile Arg Asp Ala Lys Lys
1               5                   10                  15

Arg Thr Ala Leu His Trp Ala Cys Ala Asn Gly His Ala Glu Val Val
            20                  25                  30

Thr Leu Leu Val Asp Arg Lys Cys Gln Leu Asp Val Leu Asp Gly Glu
        35                  40                  45

Asn Arg Thr Thr Leu Met Lys Ala Leu Gln Cys Gln Arg Glu Ala Cys
    50                  55                  60

Ala Asn Ile Leu Ile Asp Ser Gly Ala Asp Pro Asn Ile Val Asp Val
65                  70                  75                  80

Tyr Gly Asn Thr Ala Val His Tyr Ala Val Asn Ser Glu Asn Leu Ser
                85                  90                  95

Val Val Ala Lys Leu Leu Ser Cys Gly Thr Asp Ile Lys Val Lys Asn
            100                 105                 110

Lys Leu Val
        115

<210> SEQ ID NO 19
<211> LENGTH: 117
<212> TYPE: PRT
<213> ORGANISM: Homo sapiens

<400> SEQUENCE: 19

Met Met Lys Lys Thr Thr Met Asp Leu Asn Ile Arg Asp Ala Lys Lys
1               5                   10                  15

Arg Thr Ala Leu His Trp Ala Cys Ala Asn Gly His Ala Glu Val Val
            20                  25                  30

Thr Leu Leu Val Asp Arg Lys Cys Gln Leu Asp Val Leu Asp Gly Glu
        35                  40                  45

Asn Arg Thr Thr Leu Met Lys Ala Leu Gln Cys Gln Arg Glu Ala Cys
    50                  55                  60

Ala Asn Ile Leu Ile Asp Ser Gly Ala Asp Pro Asn Ile Val Asp Val
65                  70                  75                  80

Tyr Gly Asn Thr Ala Val His Tyr Ala Val Asn Ser Glu Asn Leu Ser
                85                  90                  95

Val Val Ala Lys Leu Leu Ser Cys Gly Thr Asp Ile Lys Val Lys Asn
            100                 105                 110

Lys Gln Pro Leu Pro
        115

<210> SEQ ID NO 20
<211> LENGTH: 202
<212> TYPE: PRT
<213> ORGANISM: Homo sapiens

<400> SEQUENCE: 20

Met Met Lys Lys Thr Thr Met Asp Leu Asn Ile Arg Asp Ala Lys Lys
1               5                   10                  15

Arg Thr Ala Leu His Trp Ala Cys Ala Asn Gly His Ala Glu Val Val

```
                    20                  25                  30
Thr Leu Leu Val Asp Arg Lys Cys Gln Leu Asp Val Leu Asp Gly Glu
            35                  40                  45
Asn Arg Thr Thr Leu Met Lys Ala Leu Gln Cys Gln Arg Glu Ala Cys
 50                  55                  60
Ala Asn Ile Leu Ile Asp Ser Gly Ala Asp Pro Asn Ile Val Asp Val
 65                  70                  75                  80
Tyr Gly Asn Thr Ala Val His Tyr Ala Val Asn Ser Glu Asn Leu Ser
                85                  90                  95
Val Val Ala Lys Leu Leu Ser Cys Gly Thr Asp Ile Lys Val Lys Asn
                100                 105                 110
Lys Ala Gly His Thr Pro Leu Leu Ala Ile Arg Lys Arg Ser Glu
                115                 120                 125
Gln Ile Val Glu Phe Leu Leu Thr Lys Asn Ala Asn Ala Asn Gly Val
            130                 135                 140
Asp Lys Phe Lys Cys Ile His Gln Gln Leu Leu Glu Tyr Lys Gln Lys
145                 150                 155                 160
Ile Ser Lys Asn Ser Gln Asn Ser Asn Pro Glu Gly Thr Ser Glu Gly
                165                 170                 175
Thr Pro Asp Glu Ala Ala Pro Leu Ala Glu Arg Thr Pro Asp Thr Ala
                180                 185                 190
Glu Ser Leu Val Glu Arg Thr Pro Asp Glu
                195                 200

<210> SEQ ID NO 21
<211> LENGTH: 115
<212> TYPE: PRT
<213> ORGANISM: Homo sapiens

<400> SEQUENCE: 21

Met Met Lys Lys Thr Thr Met Asp Leu Asn Ile Arg Asp Ala Lys Lys
 1               5                  10                  15
Arg Thr Ala Leu Tyr Trp Ala Cys Ala Asn Gly His Ala Glu Val Val
                20                  25                  30
Thr Leu Leu Val Asp Arg Lys Cys Gln Leu Asp Val Leu Asp Gly Glu
            35                  40                  45
Asn Arg Thr Ile Leu Met Lys Ala Leu Gln Cys Gln Arg Glu Ala Cys
 50                  55                  60
Ala Asn Ile Leu Ile Asp Ser Gly Ala Asp Pro Asn Ile Val Asp Val
 65                  70                  75                  80
Tyr Gly Asn Thr Ala Val His Tyr Ala Val Asn Ser Glu Asn Leu Ser
                85                  90                  95
Val Val Ala Lys Leu Leu Ser Cys Gly Ala Asp Ile Glu Val Lys Asn
                100                 105                 110
Lys Leu Val
        115

<210> SEQ ID NO 22
<211> LENGTH: 115
<212> TYPE: PRT
<213> ORGANISM: Homo sapiens

<400> SEQUENCE: 22

Met Met Lys Lys Thr Thr Met Asp Pro Asn Ile Arg Asp Ala Lys Lys
 1               5                  10                  15
Arg Thr Ala Leu His Trp Ala Cys Ala Asn Gly His Ala Glu Val Val
                20                  25                  30
```

Thr Leu Leu Val Asp Arg Lys Cys Gln Leu Asp Val Leu Asp Gly Glu
        35                  40                  45

Asn Gly Thr Pro Leu Met Lys Ala Val Gln Cys Gln Arg Glu Val Cys
 50                  55                  60

Ala Asn Ile Leu Ile Asp Ser Gly Ala Asp Pro Asn Ile Val Asp Val
 65                  70                  75                  80

Tyr Val Asn Thr Ala Val His Tyr Ala Val Tyr Gly Glu Asn Leu Ser
                 85                  90                  95

Val Val Ala Lys Leu Leu Ser Cys Gly Ala Asp Ile Lys Val Lys Asn
                100                 105                 110

Lys Leu Ala
        115

<210> SEQ ID NO 23
<211> LENGTH: 115
<212> TYPE: PRT
<213> ORGANISM: Homo sapiens

<400> SEQUENCE: 23

Met Met Lys Lys Thr Thr Met Asp Leu Asn Ile Arg Asp Ala Lys Lys
 1               5                  10                  15

Arg Thr Ala Leu His Trp Ala Cys Ala Asn Gly His Ala Glu Val Val
                20                  25                  30

Thr Leu Leu Ala Asp Arg Lys Tyr Gln Leu Asp Val Leu Asp Gly Glu
        35                  40                  45

Asn Arg Thr Thr Leu Met Lys Ala Leu Gln Cys Gln Arg Glu Ala Cys
 50                  55                  60

Ala Asn Ile Leu Ile Asp Ser Gly Ala Asp Pro Asn Ile Val Gly Val
 65                  70                  75                  80

Tyr Gly Asn Thr Ala Val His Tyr Ala Val Asn Ser Glu Asn Leu Ser
                 85                  90                  95

Val Val Ala Lys Leu Leu Ser Cys Gly Ala Asp Ile Glu Leu Lys Asn
                100                 105                 110

Lys Leu Val
        115

<210> SEQ ID NO 24
<211> LENGTH: 68
<212> TYPE: PRT
<213> ORGANISM: Homo sapiens

<400> SEQUENCE: 24

Met Gln Met Gln Met Glu Leu Ile Ser Leu Asn Ala Phe Ile Asn Asn
 1               5                  10                  15

Phe Trp Asn Ile Asn Lys Arg Tyr Leu Lys Ile Leu Lys Ile Val Ile
                20                  25                  30

Gln Lys Glu His Leu Lys Glu His Leu Thr Arg Leu His Pro Trp Arg
        35                  40                  45

Lys Glu His Leu Thr Arg Leu Lys Ala Trp Trp Lys Glu His Leu Thr
 50                  55                  60

Asn Arg Ile Gln
 65

<210> SEQ ID NO 25
<211> LENGTH: 19
<212> TYPE: DNA
<213> ORGANISM: Artificial sequence
<220> FEATURE:

<223> OTHER INFORMATION: Synthetic oligonucleotide

<400> SEQUENCE: 25
ctgaaagctt ggtggaaag                                                    19

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
gttccttctt ccaaaacttc                                                   20

<210> SEQ ID NO 27
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 27
aagactgaat gagtggcag                                                    19

<210> SEQ ID NO 28
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 28
ctgattcaaa ttacttctta cag                                               23

<210> SEQ ID NO 29
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 29
ccatggctca cacctgtaat ctcatcac                                          28

<210> SEQ ID NO 30
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 30
cgacgtggac tatccatgaa cgcacgcagt cggtac                                 36

<210> SEQ ID NO 31
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 31
gaaaaagtta gaagtgaagc aacttgag                                          28

<210> SEQ ID NO 32

<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 32
tcgagcggcc gcccgggcag gtcgacgtgg actatccatg aacgca    46

<210> SEQ ID NO 33
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 33
gctgtccatt atgctgttaa c    21

<210> SEQ ID NO 34
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 34
ttttgagaat ttttagatat c    21

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
cctgtggtgc agacatcg    18

<210> SEQ ID NO 36
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 36
attccaaaag ttgttgatga ac    22

<210> SEQ ID NO 37
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 37
ctgtccatta tgctgtttat g    21

<210> SEQ ID NO 38
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 38

```
aatttttaga tatcttttgt ttg                                              23
```

<210> SEQ ID NO 39
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 39

```
tgctgatcca aatattgtag g                                                21
```

<210> SEQ ID NO 40
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 40

```
catttaaact tatcaactgc aa                                               22
```

<210> SEQ ID NO 41
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 41

```
cgggatccat gaagaagacg acaatg                                           26
```

<210> SEQ ID NO 42
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 42

```
cggaattcct attcgtcagg tgttct                                           26
```

<210> SEQ ID NO 43
<211> LENGTH: 370
<212> TYPE: DNA
<213> ORGANISM: Homo sapiens

<400> SEQUENCE: 43

```
ggagaggctg gagtgtccaa aagcttggcc gactgagatt gctagtcgtg tcagggcggg      60
tgcgggactg aagaagggcg agggcgagcg gcggggactg gggaagggcg agcagcggga     120
ggcacgggct ctctctagca ggtggctgca gccatggaga ggctctgtgc cgccgctgtc     180
aagggccaga cgggcccaga gcgcccaagc cccttcagtc agctggtcta caccaacaac     240
gactcttacg tgattcacca tggggatctc aggaagatcc acaaagctgc ctcccgggcc     300
aagcctggaa gctggagagg atgatgaaga agacgacaat ggacctgaac ataagagatg     360
cgaagaagag                                                            370
```

<210> SEQ ID NO 44
<211> LENGTH: 115
<212> TYPE: DNA
<213> ORGANISM: Homo sapiens

<400> SEQUENCE: 44

```
gactgctcta cactgggcct gtgccaatgg ccatgcagaa gtagtaacac ttctggtaga      60
tagaaagtgc cagcttgacg tccttgatgg cgaaaacagg acaactctga tgaag          115

<210> SEQ ID NO 45
<211> LENGTH: 174
<212> TYPE: DNA
<213> ORGANISM: Homo sapiens

<400> SEQUENCE: 45
gctctgcaat gccagaggga ggcttgtgca aatattctca tagattctgg tgctgatcca      60
aatattgtag atgtgtatgg caacacagct gtccattatg ctgttaacag tgagaatttg     120
tcagtggtgg caaaattgct gtcctgtggt acagacatta aagtgaagaa caag           174

<210> SEQ ID NO 46
<211> LENGTH: 137
<212> TYPE: DNA
<213> ORGANISM: Homo sapiens

<400> SEQUENCE: 46
ttagtgtaaa actacaagaa agtaaaattt gcctgcataa attgagtcaa catgtaaaat      60
ttaggagaca tgcagaaatc tggatttcct cttaaaggat tgaatcttgt gtctcttgag     120
cccgtatgac tgtttgg                                                   137

<210> SEQ ID NO 47
<211> LENGTH: 86
<212> TYPE: DNA
<213> ORGANISM: Homo sapiens

<400> SEQUENCE: 47
cagccacttc cttagtgacc catttagagc aggagtgcct gacattggca tttggaatct      60
tgggatcatt gatagaagag aatcaa                                          86

<210> SEQ ID NO 48
<211> LENGTH: 107
<212> TYPE: DNA
<213> ORGANISM: Homo sapiens

<400> SEQUENCE: 48
gctggccaca caccactttt attggccata aggaaaagaa gtgagcaaat tgtggaattt      60
ttactgacaa aaaatgcaaa tgcaaatgga gttgataagt ttaaatg                   107

<210> SEQ ID NO 49
<211> LENGTH: 163
<212> TYPE: DNA
<213> ORGANISM: Homo sapiens

<400> SEQUENCE: 49
cacagccctc atgcttgcca tatgtcatgg atcatcagag atagttggca agcttcttca      60
gcaaaatgtt gacatctgtg ctgaagctac atgcggaatg attgcagaac gttatgctgt     120
tgcttgtgga tttaatctct aagtgtttac atttaaaggc tag                       163

<210> SEQ ID NO 50
<211> LENGTH: 65
<212> TYPE: DNA
<213> ORGANISM: Homo sapiens

<400> SEQUENCE: 50
cattcatcaa caacttttgg aatataaaca aaagatatct aaaaattctc aaaatagtaa      60
```

-continued

| tccag | 65 |

<210> SEQ ID NO 51
<211> LENGTH: 907
<212> TYPE: DNA
<213> ORGANISM: Homo sapiens

<400> SEQUENCE: 51

| aaggaacatc tgaaggaaca cctgacgagg ctgcacccstt ggcggaaaga acacctgaca | 60 |
| cggctgaaag cttggtggaa agaacacctg acgaatagga tacagtgaat tcctcttcaa | 120 |
| agattttagc ctgtaaacat cctttaaaat tcaagagggg ggaagattaa gtacaatgag | 180 |
| ttctgagttc ctcatcaaag aacaaatatg tcagtatgtt cagcttctcc gttctttgtt | 240 |
| ctccgtttta aagtttaact tcctcgttcg ttatgcctcc ttgcccctag tttcattaaa | 300 |
| caacccctt ctagcctcta cacctgcttt tgtctttagt cattcttagt aacctgctct | 360 |
| gtccttagtc atccttagac acctgctctg taactgtctt tcccgctgaa actactcacc | 420 |
| ctgccactcc agctcatacc cctgccctct ttgaaatagc caatctgaat tggcttagag | 480 |
| tgtgcagtcc aaccctatcc aatagggaaa agacacaaca gtagggacta gctgcgttag | 540 |
| aaataagaac actttcccct cccttgtccg gtgtgatctt gcctttgctc catctgcaag | 600 |
| accactcttc catagaagta aatttgcctt gctgtaaaaa cttgttgctg gagtgctgac | 660 |
| ggttctttgt ggcaccgaaa attatttttcc aaaaatttga gggcccaccc aacattccca | 720 |
| ttctcctctg ggggagggtc cagtcctctc ccttgaggag gtgcaccccg ctgcctcgtt | 780 |
| gcagtggcca taaaggtaag gaatcaagac tcaactggtg cgattaataa acccgggctc | 840 |
| tcagcaacgt ggaaagaaac aggccagcaa ctctggggaa aggatcttca cataccgtgg | 900 |
| cgaccag | 907 |

<210> SEQ ID NO 52
<211> LENGTH: 418
<212> TYPE: DNA
<213> ORGANISM: Homo sapiens

<400> SEQUENCE: 52

| tgtgctcttg ccattgctcc atccgcaaga ctcacccttc tatagaagta aatttgcctt | 60 |
| gctggagtgc taactcttct tgtgtcacc aaaaagttat ttccaacatg aaggtgcacc | 120 |
| cttggtggag ggaacatctg acgaagttca atgtttgggg aaagcaatat ctggaaagat | 180 |
| tgaacagtca gcaggagaaa cacctaggaa aattacaagg cctgtgaaag aaacatctga | 240 |
| gaaatttgca tggccacaag aaaggccttc aaagaccaca cgggaggaaa agaaacatc | 300 |
| tgtaaagact gaatgagtgg caggagtaac atttaataaa attgaagttt tggaagaagg | 360 |
| aacatctaag atgatcacat gtcctacaaa aaaacagcta caaaagcaag tacaaatg | 418 |

<210> SEQ ID NO 53
<211> LENGTH: 120
<212> TYPE: DNA
<213> ORGANISM: Homo sapiens

<400> SEQUENCE: 53

| gtatactgtt gatgtggttg ataattctgg tatccaagaa gaaatctccc aagatcctac | 60 |
| ctaactttt gtaactaaag cggcatacat acacaggtag tgggaaaatg tctagagtga | 120 |

<210> SEQ ID NO 54
<211> LENGTH: 524
<212> TYPE: DNA

<213> ORGANISM: Homo sapiens

<400> SEQUENCE: 54

| | | |
|---|---|---|
| ttcaactagc ctatcaaaaa tcttggatgc agttctttct tgtgaaagag caagggaact | 60 |
| taaaaaatat ccctgtgggc caggcgccat ggctcacacc tgtaatctca tcactttggg | 120 |
| aggccaaggc gggcagatca tgacgtcagg agatcaagac catcctggct aacacagtga | 180 |
| aaccccgtct ctactaaaaa tacaaaaaaa aaaattagcc gggcgtggtg gcaggtgact | 240 |
| atagtcccag ctactcggga ggctgaggca ggagaatggc atgaacccgg gaggcggagc | 300 |
| ttgcagtgag tggagatcgc gccactgcac tccagcctag caacagagc gagactccgt | 360 |
| caaaaaaat aaagaaaaa aaatccctg tgaacaactt acagcaaaaa tgaaacaaat | 420 |
| gaaaataag cttcgtgtac tacaaaagga actaacagaa gcaaaataaa taaaatcata | 480 |
| gagaatcaaa aacttaaaag agaacaagag ctctgcagtg tgag | 524 |

<210> SEQ ID NO 55
<211> LENGTH: 197
<212> TYPE: DNA
<213> ORGANISM: Homo sapiens

<400> SEQUENCE: 55

| | | |
|---|---|---|
| attgacttta aaccaagaag aagagaagag aagaaatgcc aatatattaa atgaaaaatt | 60 |
| agggaagaat taggaaaaat cgaagagcaa caaagaaaa agttagaagt gaagcaactt | 120 |
| gagctcactc tccgaatata caaaatatgg aattgaagac tgtaagaagt aatttgaatc | 180 |
| agctcaatca atcgctg | 197 |

<210> SEQ ID NO 56
<211> LENGTH: 118
<212> TYPE: DNA
<213> ORGANISM: Homo sapiens

<400> SEQUENCE: 56

| | | |
|---|---|---|
| ggccgcaatc tgtcaccaag gctagggtgc agtggcacaa tcatggatca ctgcagcctc | 60 |
| aaactctggg gctcaagcag acctcctgtc tcagcctacc aagtagctgg gaccacag | 118 |

<210> SEQ ID NO 57
<211> LENGTH: 414
<212> TYPE: DNA
<213> ORGANISM: Homo sapiens

<400> SEQUENCE: 57

| | | |
|---|---|---|
| gccatatgaa atggaggcaa tttgtttatc agtctgagtc tccagaactc ctgaattttt | 60 |
| tgccaaggaa actggagaaa ctctcgtcca ggtaccaacc aaggagatta tttctacaaa | 120 |
| agaaggaaca gacactgaat gactcatttc ccttcctctc acatggaagc agaattagac | 180 |
| actcctgcca gcctgaccca agtctgtaca ggacatcctg aaatgtctta aagattcccg | 240 |
| ggtgattgtg agaggattcc tagtgaccat ggactgatga ccgtatgttg atccaggtag | 300 |
| gaaagactca agctgattat aaatagaaaa tggaactgcc ctggtacagc tccagaacct | 360 |
| ggatctatgt gtgatatcac ctgttctgat tagctaggtc ttaggtaaga gaaa | 414 |

CTSP CANCER-TESTIS ANTIGENS

RELATED APPLICATION

This application is a national stage filing under 35 U.S.C. §371 of international application PCT/US2007/002486, filed Jan. 29, 2007, which was published under PCT Article 21(2) in English, and claims the benefit under 35 U.S.C. §119(e) of U.S. provisional patent application Ser. No. 60/763,345, filed Jan. 30, 2006, the contents of which are incorporated herein by reference in their entirety.

FIELD OF THE INVENTION

The invention relates to a family of cancer-testis antigens and the nucleic acid molecules that encode them. The invention further relates to the use of the nucleic acid molecules, polypeptides and fragments thereof in methods and compositions for the diagnosis, prognosis and treatment of diseases, such as cancer. More specifically, the invention relates to the discovery of a novel cancer/testis (CT) antigen, CTSP-1.

BACKGROUND OF THE INVENTION

CT antigens are predominantly expressed in normal gametogenic tissues as well as in different histological types of tumors (Scanlan et al., 2002, Immunol Rev. 188:22-32. Review; Scanlan et al., 2004, Cancer Immun. 4:1. Review; Simpson et al., 2005, Nat Rev Cancer. 5(8):615-25. Review; Zendman et al., 2003, J Cell Physiol. 194(3):272-88. Review). In testis, CT antigens are expressed exclusively in cells of the germ cell lineage, although there is a marked variation in the protein expression pattern during different stages of sperm development. Likewise, a heterogeneous expression is also observed in tumors (Scanlan et al., 2002, Immunol Rev. 188:22-32. Review; Zendman et al., 2003, J Cell Physiol. 194(3):272-88. Review). Methylation status of the promoter region seems to be the main, but not the only regulator of their specific expression pattern (Scanlan et al., 2002, Immunol Rev. 188:22-32. Review; Simpson et al., 2005, Nat Rev Cancer. 5(8):615-25. Review; Zendman et al., 2003, J Cell Physiol. 194(3):272-88. Review). Most CT antigens have no defined biological function but their involvement in signaling, transcription, translation and chromosomal recombination has been proposed (Simpson et al., 2005, Nat Rev Cancer. 5(8):615-25. Review; Zendman et al., 2003, J Cell Physiol. 194(3):272-88. Review). It has also been proposed that the aberrant expression of CT antigens in tumors recapitulates portions of the germline gene expression programme and is related to some characteristics of the neoplastic phenotype such as immortality, invasiveness, immune evasion and metastatic capacity (Simpson et al., 2005, Nat Rev Cancer. 5(8):615-25. Review; Old, L J., 2001, Cancer Immun. 1:1).

Due to their restricted expression pattern, CT antigens are considered to be ideal targets for cancer immunotherapy (Scanlan et al., 2002, Immunol Rev. 188:22-32. Review; Bodey, 2002, Expert Opin Biol Ther. 2(6):577-84. Review). Indeed, a small subset of patients immunized with the known CT antigens MAGE-A and NY-ESO-1 have shown clinical benefits following immunization (Chen et al., 2004, Proc. Natl. Acad. Sci. U.S.A. 101: 9363-9368; Davis et al., 2004, Proc. Natl. Acad. Sci. U.S.A. 101:10697-10702; Jager et al., 2000, Proc. Natl. Acad. Sci. U.S.A. 97: 12198-12203; Marchand et al., 1999, Int. J. Cancer. 80: 219-230). However, because CT antigens are expressed in only a small subset of human tumors and in only a fraction of cases of a given tumor type, the identification of additional CT antigens is crucial for improving current immunotherapy protocols. Presently, 44 distinct CT-antigen families have been described, of which several have multiple members resulting in a total of 89 transcripts (Simpson et al., 2005, Nat Rev Cancer. 5(8):615-25. Review).

The identification of additional CT antigens and other genes having a tumor-associated expression profile is needed for the development of additional therapeutics and diagnostics to permit effective treatment and diagnosis of a broader group of cancer patients.

SUMMARY OF THE INVENTION

During the process of identification of novel genes located on human chromosome 21 (HC21) (Reymond et al., 2002, Genomics 79: 824-832), we found a gene (C21ORF99) which is predominantly expressed in normal testis and has a high similarity to the amino-terminal region of the breast differentiation antigen NYBR-1 (Jager et al., 2001, Cancer Res. 61: 2055-2061). In this work, we refined the characterization of the C21ORF99 gene structure and renamed it to CTSP-1. We found that CTSP-1 has a restricted expression pattern in normal tissues characteristic of CT antigens and is expressed at a high frequency in tumor cell lines and in tumor samples. We also found that CTSP-1 is part of a highly conserved gene family dispersed throughout the genome and that some members of this family have also an expression pattern characteristic of CT antigens. Antibodies against members of this gene family were frequently detected in plasma samples from patients with a wide spectrum of tumors.

According to one aspect of the invention, an isolated nucleic acid molecule is provided that is selected from the group consisting of:

(a) complements of nucleic acid molecules that hybridize under high stringency conditions to a second nucleic acid molecule including a nucleotide sequence set forth as any of SEQ ID NOs: 1-11, wherein the complements exclude SEQ ID NO: 12, (b) nucleic acid molecules that differ from the nucleic acid molecules of (a) in codon sequence due to the degeneracy of the genetic code, and (c) full-length complements of (a) or (b).

In some embodiments, the isolated nucleic acid molecule includes, or preferably consists of, a nucleotide sequence set forth as any of SEQ ID NOs: 1-11. In preferred embodiments, the isolated nucleic acid molecule is a CTSP-1 nucleic acid molecule that includes, or preferably consists of, a nucleotide sequence set forth as any of SEQ ID NOs: 1-8, a protein-coding portion thereof, or an alternatively spliced product thereof.

According to a second aspect of the invention, isolated nucleic acid molecules are provide that include, or preferably consist of, one or more of SEQ ID NOs:43-57 or full-length complements thereof, wherein the nucleic acid molecule does not consist of SEQ ID NO:12.

According to a third aspect of the invention, an isolated nucleic acid molecule is provided that includes (a) a nucleotide sequence that is at least about 90% identical to a nucleotide sequence set forth as any of SEQ ID NOs: 1-11 or a full-length complement thereof, or (b) a nucleotide sequence that is at least about 90% identical to a nucleotide sequence set forth as any of SEQ ID NOs:43-57 or a full-length complement thereof, wherein the nucleotide sequence does not consist of SEQ ID NO: 12.

In some embodiments, the nucleic acid molecule comprises a nucleotide sequence that is at least about 95% identical, preferably at least about 97% identical, more preferably at least about 98% identical, and most preferably at least about 99% identical to the nucleotide sequence.

According to a fourth aspect of the invention, compositions are provided that include any of the foregoing isolated nucleic acid molecules and a carrier, or any of the foregoing isolated nucleic acid molecules attached to a solid substrate.

According to a fifth aspect of the invention, kits are provided that include one or more nucleic acid molecules that hybridize under high stringency conditions to a nucleotide sequence set forth as any of SEQ ID NOs:1-11 and 43-57.

In some embodiments, the one or more nucleic acid molecules are detectably labeled. In other embodiments, the one or more nucleic acid molecules consist of a first primer and a second primer, wherein the first primer and the second primer are constructed and arranged to selectively amplify at least a portion of a nucleic acid molecule that comprises a nucleotide sequence set forth as any of SEQ ID NOs:1-11 and 43-57. In further embodiments, the one or more nucleic acids are bound to a solid substrate.

According to a sixth aspect of the invention, expression vectors including any of the foregoing isolated nucleic acid molecules, operably linked to a promoter, are provided. Also provided are isolated host cells transformed or transfected with the expression vectors. In some embodiments, the host cells express a MHC molecule, preferably recombinantly. In some preferred embodiments, the host cell is a dendritic cell.

Also provided in accordance with the invention are compositions that include the foregoing isolated host cells and a carrier.

According to a seventh aspect of the invention, isolated polypeptides encoded by any of the foregoing isolated nucleic acid molecules are provided, as are fragments of the polypeptides that are at least eight amino acids in length. In some embodiments, the isolated polypeptide includes, or preferably consists of, an amino acid sequence set forth as any of SEQ ID NOs: 13-23.

According to an eighth aspect of the invention, compositions including any of the foregoing isolated polypeptides and a carrier are provided; preferably the compositions also include an adjuvant. Also provided are compositions including any of the foregoing isolated polypeptides attached to a solid substrate.

In some embodiments, the compositions further include at least one additional cancer-testis antigen polypeptide, preferably a NY-ESO-1, MAGE or SSX polypeptide, preferably also containing a carrier and/or an adjuvant.

According to a ninth aspect of the invention, isolated antibodies or antigen-binding fragments thereof are provided that selectively bind to the foregoing isolated polypeptides. In some embodiments, the antibody is a monoclonal antibody, a human antibody, a domain antibody, a humanized antibody, a single chain antibody or a chimeric antibody. In other embodiments, the isolated antigen-binding fragment thereof of claim A 16, wherein the antibody fragment is a F(ab')$_2$, Fab, Fd, or Fv fragment. Also provided are compositions including any of the foregoing isolated antibodies or antigen-binding fragments and a carrier, or attached to a solid substrate. Kits including the isolated antibodies or antigen-binding fragments also are provided.

According to a tenth aspect of the invention, methods of diagnosing cancer in a subject are provided. The methods include obtaining a biological sample from the subject, and determining the presence in the biological sample of an antibody that binds specifically to one or more polypeptides encoded by a nucleotide sequence set forth as any of SEQ ID NO: 1-11. The presence of the antibody is indicative of the subject having cancer.

In some embodiments, the step of determining the presence of the antibody includes contacting the biological sample with one or more polypeptides encoded by a nucleic acid molecule comprising (1) a nucleotide sequence set forth as any of SEQ ID NOs: 1-11 or (2) a nucleotide sequence that is at least 90% identical to the nucleotide sequence of (1), and determining the binding of the antibody to the polypeptide. In certain embodiments, the nucleic acid molecule includes a nucleotide sequence set forth as any of SEQ ID NO: 1-8. In other embodiments, the polypeptide includes an amino acid sequence set forth as any of SEQ ID NOs: 13-23, preferably SEQ ID NOS: 13-20, or a fragment thereof that is at least eight amino acids in length. Preferably the polypeptide is produced recombinantly and/or is bound to a substrate.

In other embodiments, the step of determining the binding of the antibody with the polypeptide is performed with an ELISA-based method.

In preferred embodiments of the methods, the biological sample is blood or serum.

According to an eleventh aspect of the invention, methods for diagnosing cancer in a subject are provided. The methods include obtaining a biological sample from a subject, and determining the expression in the biological sample of a polypeptide or a nucleic acid molecule that encodes the polypeptide, wherein the nucleic acid molecule includes (1) a nucleotide sequence set forth as any of SEQ ID NOs: 1-11 or (2) a nucleotide sequence that is at least 90% identical to the nucleotide sequence of (1). The expression in the biological sample of the polypeptide or the nucleic acid molecule that encodes it is indicative of the subject having cancer.

In some embodiments, the nucleic acid molecule includes the nucleotide sequence set forth as any of SEQ ID NOs: 1-8. In other embodiments, the polypeptide includes an amino acid sequence set forth as any of SEQ ID NOs: 13-23, preferably SEQ ID NOS: 13-20, or a fragment thereof that is at least eight amino acids in length.

In other embodiments, the step of determining the expression of the polypeptide or the nucleic acid molecule that encodes the polypeptide includes contacting the biological sample with an agent that selectively binds to the polypeptide or the nucleic acid molecule that encodes the polypeptide.

In some embodiments, the agent is a nucleic acid probe or a nucleic acid primer. Optionally, the expression of the nucleic acid molecule is determined by nucleic acid hybridization using the nucleic acid probe or nucleic acid amplification using the nucleic acid primer. Preferably the nucleic acid amplification is real-time RT-PCR or RT-PCR·Preferably the nucleic acid hybridization is performed using a nucleic acid microarray containing the nucleic acid probe.

In some embodiments, the agent is a polypeptide, preferably an antibody or antigen-binding fragment thereof, more preferably a monoclonal antibody or a F(ab')$_2$, Fab, Fd, or Fv fragment. In certain embodiments, the antibody or antigen-binding fragment is labeled with a detectable label, preferably a fluorescent or radioactive label.

In preferred embodiments of the methods, the sample comprises tissue, cells, and/or blood.

According to a twelfth aspect of the invention, methods for determining onset, progression, or regression of cancer in a subject are provided. The methods include obtaining from a subject a first biological sample at a first time, determining the expression in the first sample of a polypeptide or a nucleic acid molecule that encodes the polypeptide, wherein the nucleic acid molecule includes (1) a nucleotide sequence set forth as any of SEQ ID NOs: 1-11 or (2) a nucleotide sequence that is at least 90% identical to the nucleotide sequence of (1), obtaining from the subject a second biological sample at a second time subsequent to the first time, determining the expression in the second sample of the polypeptide or the nucleic acid molecule that encodes the polypeptide, and comparing the expression in the first sample to the expression in the second sample as a determination of the onset, progression, or regression of the cancer. An increase in expression in the second sample compared to the first sample is indicative of onset or progression of the cancer, and a decrease in the expression in the second sample compared to the first sample is indicative of regression of the cancer.

In some embodiments, the nucleic acid molecule includes the nucleotide sequence set forth as any of SEQ ID NOs: 1-8. In other embodiments, the polypeptide includes an amino acid sequence set forth as any of SEQ ID NOs: 13-23, preferably SEQ ID NOS: 13-20, or a fragment thereof that is at least eight amino acids in length.

In other embodiments, the step of determining the expression of the polypeptide or the nucleic acid molecule that encodes the polypeptide includes contacting first biological sample and the second biological sample with an agent that selectively binds to the polypeptide or the nucleic acid molecule that encodes the polypeptide.

In some embodiments, the agent is a nucleic acid probe or a nucleic acid primer. Optionally, the expression of the nucleic acid molecule is determined by nucleic acid hybridization using the nucleic acid probe or nucleic acid amplification using the nucleic acid primer. Preferably the nucleic acid amplification is real-time RT-PCR or RT-PCR. Preferably the nucleic acid hybridization is performed using a nucleic acid microarray containing the nucleic acid probe.

In some embodiments, the agent is a polypeptide, preferably an antibody or antigen-binding fragment thereof, more preferably a monoclonal antibody or a F(ab')$_2$, Fab, Fd, or Fv fragment. In certain embodiments, the antibody or antigen-binding fragment is labeled with a detectable label, preferably a fluorescent or radioactive label.

In preferred embodiments of the methods, the sample comprises tissue, cells, and/or blood.

According to a thirteenth aspect of the invention, methods for treating cancer in a subject are provided. The methods include administering to the subject an agent that stimulates an immune response to a polypeptide encoded by a nucleic acid molecule comprising a nucleotide sequence that is at least 90% identical to the nucleotide sequence set forth as any of SEQ ID NOs: 1-111.

In some embodiments, the nucleic acid molecule includes the nucleotide sequence set forth as any of SEQ ID NOs:1-11, preferably SEQ ID NOs: 1-8. In other embodiments, the polypeptide includes an amino acid sequence set forth as any of SEQ ID NOs: 13-23, preferably SEQ ID NOS: 13-20, or a fragment thereof that is at least eight amino acids in length.

In some embodiments, the agent that stimulates the immune response is a nucleic acid that encodes the polypeptide operably linked to a promoter; the polypeptide; a cell that expresses the polypeptide, preferably a cell that also expresses a MHC molecule; a peptide fragment of the polypeptide; or a complex of a peptide fragment of the polypeptide and a MHC molecule. Optionally the agent further comprises an adjuvant or a cytokine.

In some embodiments, the immune response elicited by an agent or agents according to the invention is a B cell response. In some embodiments, the immune response elicited by an agent or agents according to the invention is a T cell response, preferably a CD4+ T cell and/or CD8+ T cell response.

According to a fourteenth aspect of the invention, methods for treating cancer in a subject are provided. The methods include administering to a subject an effective amount of an antibody or antigen-binding fragment thereof that specifically binds to a polypeptide that comprises an amino acid sequence set forth as any of SEQ ID NOs: 13-23, or a peptide fragment thereof, or a complex of the peptide fragment and a MHC or HLA molecule.

In some embodiments, the antibody is a monoclonal antibody, preferably a chimeric, human, or humanized antibody, or a single chain antibody. In other embodiments, the antigen-binding fragment is a F(ab')$_2$, Fab, Fd, or Fv fragment.

In still other embodiments, the antibody or antigen-binding fragment thereof is bound to a cytotoxic agent, preferably one selected from the group consisting of: calicheamicin, esperamicin, methotrexate, doxorubicin, melphalan, chlorambucil, ARA-C, vindesine, mitomycin C, cisplatinum, etopside, bleomycin and 5-fluorouracil. In further embodiments, the cytotoxic agent is a radioisotope, preferably one that emits α radiation, β radiation or γ radiation. In particular embodiments, the radioisotope is selected from the group consisting of: $^{225}$Ac, $^{211}$At, $^{212}$Bi, $^{213}$Bi, $^{186}$Rh, $^{188}$Rh, $^{177}$Li, $^{90}$Y, $^{131}$I, $^{67}$Cu, $^{125}$I, $^{123}$I, $^{77}$Br, $^{153}$S, $^{166}$Bo, $^{64}$Cu, $^{212}$Pb, $^{224}$Ra and $^{223}$R.

The invention also involves the use of the genes, gene products, fragments thereof, agents which bind thereto, and other compositions and molecules described herein in the preparation of medicaments. A particular medicament is for treating cancer.

Yet another aspect of the invention provides methods for assessing the prognosis of a subject with prostate cancer. Accordingly, these methods include the steps of obtaining one or more biological samples from a subject (e.g., blood, serum, plasma, tissue biopsy, etc.) and determining the presence or absence of anti-CTSP-1 antibodies in the sample(s). The absence of anti-CTSP-1 antibodies in the biological sample is indicative of poor prognosis (e.g., shortened biochemical recurrence-free interval), whereas the presence of anti-CTSP-1 antibodies in the biological sample is indicative of good prognosis (e.g., longer survival as compared to subjects without detectable anti-CTSP-1 antibodies).

In some embodiments, the steps of obtaining a biological sample and determining the absence or presence of anti-CTSP-1 antibodies in the sample may be repeated one or more times (e.g., about 1-12 months after the first sample is obtained).

In some embodiments, the method of assessing the prognosis for a subject diagnosed with prostate cancer may further comprise measuring a non-anti-CTSP-1 antibody prostate cancer marker, such as PSA, PSMA and PAP.

Yet in other embodiments, the methods of assessing the prognosis for a subject diagnosed with prostate cancer may further include measuring the level or presence of another prostate cancer marker, such as NY-ESO-1. In some cases, the method includes determining the presence or absence of NY-ESO-1 mRNA and/or NY-ESO-1 polypeptide in a biological sample. The presence of NY-ESO-1 mRNA and/or NY-ESO-1 polypeptide in the biological sample is indicative of poor prognosis. In some cases, the method includes determining the presence or absence anti-NY-ESO-1 antibodies in a biological sample. The presence of anti-NY-ESO-1 antibodies in the biological sample is indicative of poor prognosis.

These and other aspects of the invention will be described in further detail in connection with the detailed description of the invention.

NYBR-1, NYBR-1.1 and C21 ORF99 sequences were aligned to the genomic sequence of the human chromosome 21 (HC21). Exons are represented as boxes and lines correspond to introns. RT-PCR and RACE primers are represented with arrows and triangles correspond to polyadenylation signals. Repetitive elements (LTR and Alu) are represented as black boxes.

Figure 2:
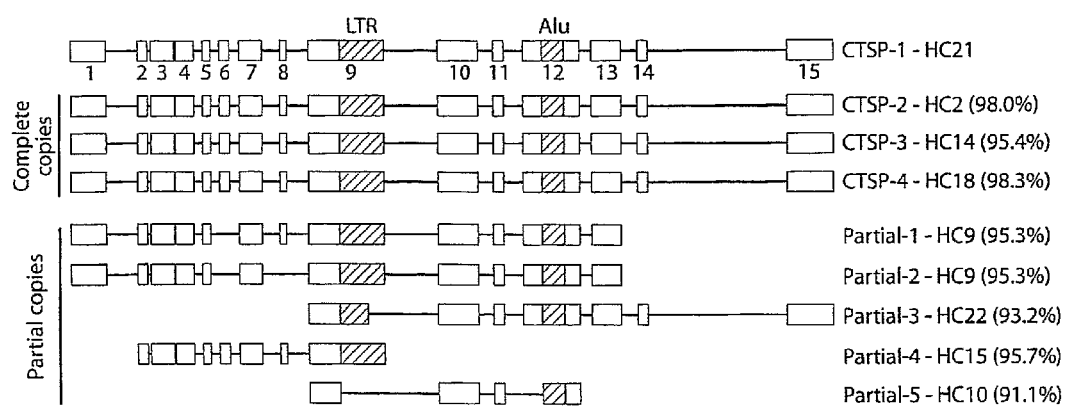

FIG. 2 provides a schematic representation of the exon/intron structure of the CTSP-1 family members. Complete and partial copies are represented with their corresponding chromosomal location and similarity to CTSP-1 consensus sequence. Repetitive elements (LTR and Alu) are represented as black boxes and exons are numbered from 1 to 15.

Figure 3A:
Figure 3B:
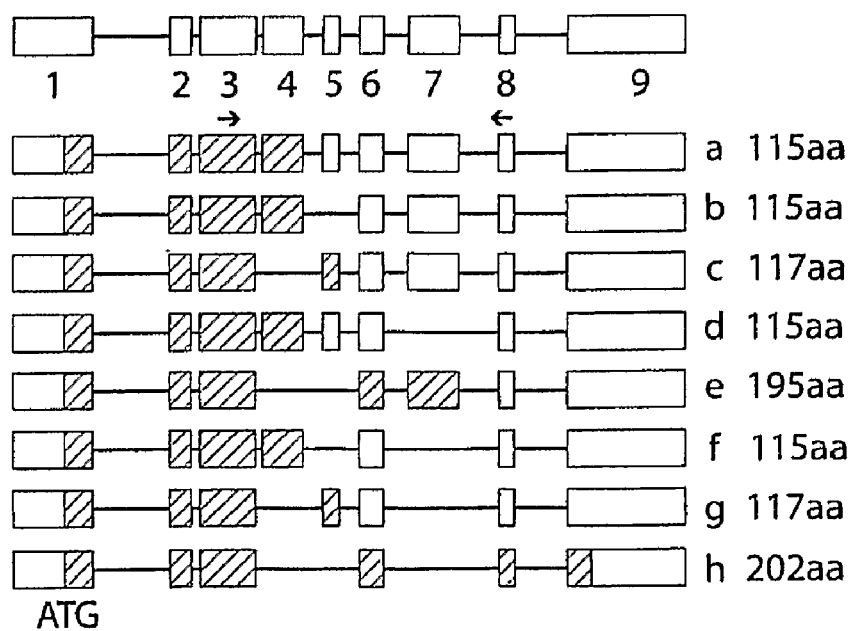

FIG. 3 depicts CTSP-1 alternative splicing isoforms. FIG. 3A provides a Southern blot of RT-PCR products amplified with CTSP-1 specific primers. Alternative splicing isoforms (a-h) are indicated with arrows. cDNA samples used were: normal testis (1), A172 glioblastoma cell line (2), A2058 melanoma cell line (3), H1155 lung tumor cell line (4), breast tumor samples (5,6), prostate tumor samples (7,8), no cDNA negative control (9). FIG. 3B provides a schematic representation of CTSP-1 alternative splicing isoforms (a-h). Exons are numbered from 1 to 9 and the coding exons are represented as gray boxes. Primers used in RT-PCR amplifications are represented as arrows and the size of the putative open reading frame for each splicing isoform is provided in amino acids (aa).

Figure 4A:
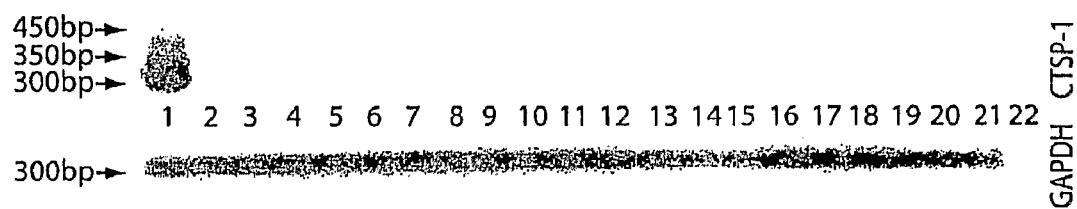
Figure 4B:
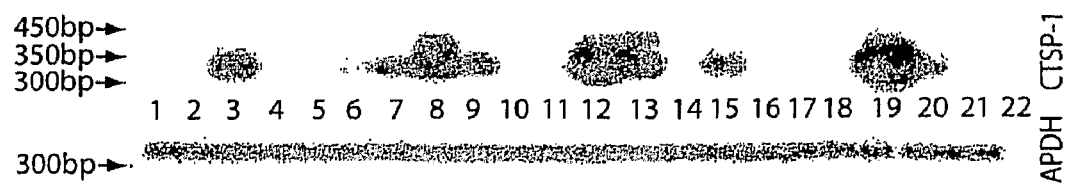

FIG. 4 depicts CTSP-1 mRNA expression patterns in normal tissues and tumor cell lines using a Southern blot of RT-PCR products amplified with CTSP-1 specific primers. FIG. 4A: Normal cDNA samples used were: 1—testis, 2—lung, 3—prostate, 4—small intestine, 5—breast, 6—brain, 7—heart, 8—uterus, 9—bone marrow, 10—placenta, 11—colon, 12—fetal brain, 13—liver, 14—fetal liver, 15—thymus, 16—salivary gland, 17—spinal cord, 18—kidney, 19—spleen, 20—skeletal muscle, 21—adrenal gland, 22—no cDNA negative control. FIG. 4B: cDNA samples from tumor cell lines used were: 1—Caski, 2—Hela, 3—A172, 4—T98G, 5—HL-60, 6—K562, 7—H358, 8—H1155, 9—Du145, 10—PC3, 11—SCABER, 12—IM9, 13—FADu, 14—MCF-7, 15—MDA436, 16—MDA-231, 17—SW-480, 18—SAOS-2, 19—A2058, 20—SKmel-25, 21—HEPG2, 22—no cDNA negative control. GAPDH amplification was used as positive control for cDNA synthesis.

Figure 5A:
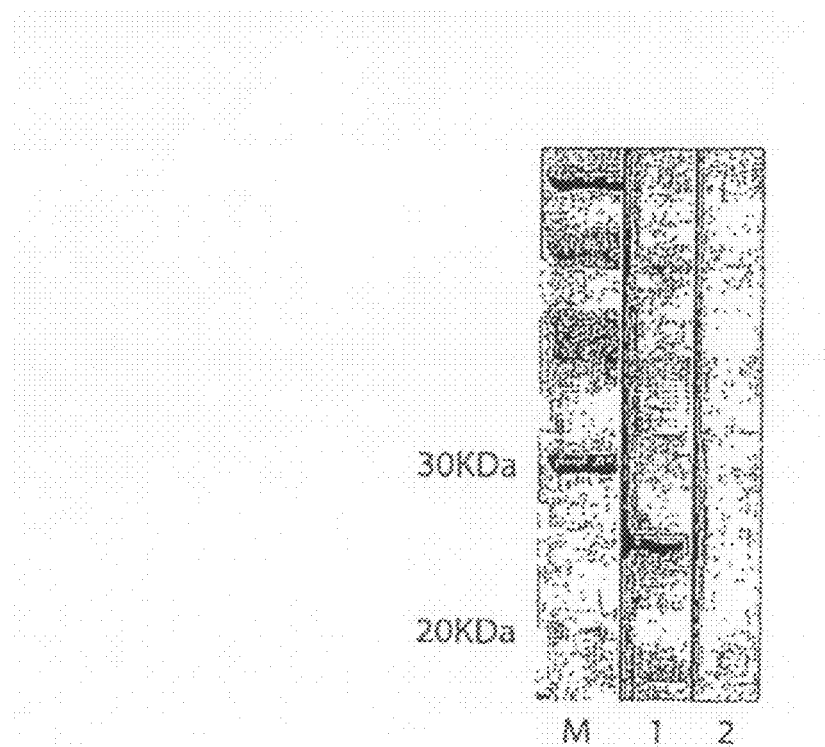
Figure 5B:
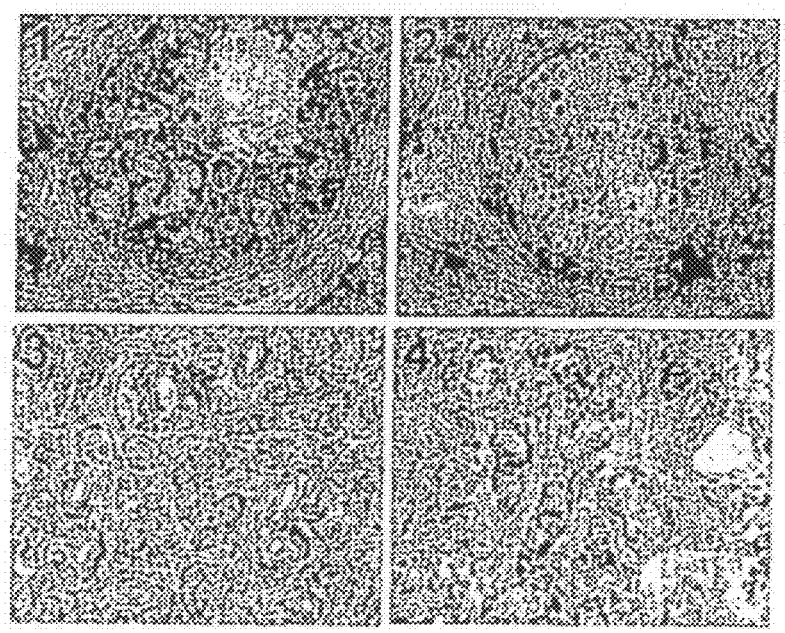

FIG. 5 depicts CTSP-1 protein expression in normal testis and in prostate tissue. FIG. 5A: CTSP-1 protein was detected by Western blot in protein extract from normal testis using a CTSP-1 polyclonal antibody (1) and pre-immune serum used as negative control (2). Molecular weight markers are indicated (M). FIG. 5B: Immunohistochemistry staining of CTSP-1 protein in normal testis (1), prostate tumor (3) and normal adjacent prostate tissue (4) using a anti-CTSP-1 antibody. Normal testis (2) incubated with pre-immune sera as negative control.

Figure 6:
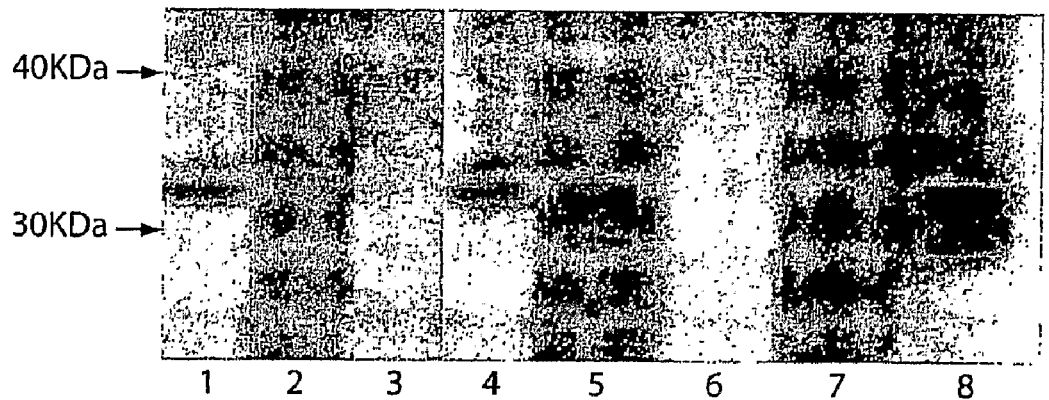

FIG. 6 is an image of Western blot analysis of antibodies in plasma samples from cancer patients that are reactive with CTSP-1 recombinant protein. A Western blot using CTSP-1 recombinant protein and plasma samples from prostate cancer patients (lanes 1-7). An anti-HisTag antibody was used as positive control in the Western blot experiments (lane 8). Molecular weight markers are indicated in kilodaltons (KDa).

Figure 7:
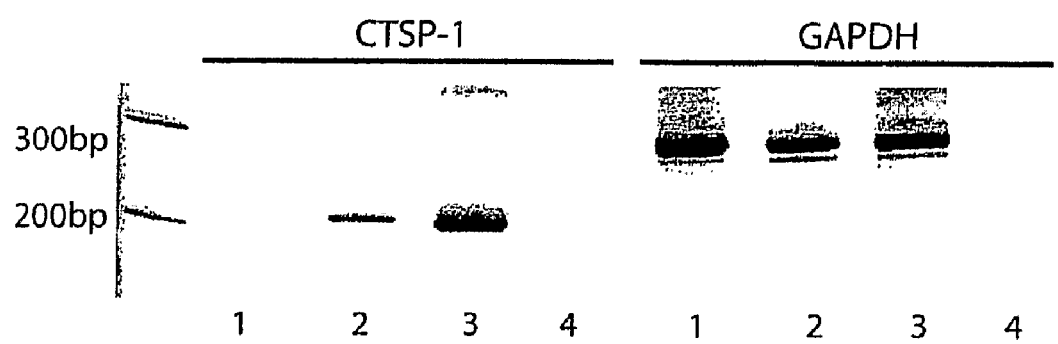

FIG. 7 depicts induction of CTSP-1 gene expression by treatment with a demethylating agent. The MCF-7 breast tumor cell line was treated with 5-Aza 2' deoxycytidine and CTSP-1 expression was detected by RT-PCR cDNAs used in the RT-PCR amplification were: MCF-7 mock (lanes marked 1), MCF-7 treated (lanes marked 2), normal testis as positive control (lanes marked 3) and no cDNA as negative control (lanes marked 4). GAPDH amplification was used as positive control for cDNA synthesis.

Figure 8A:
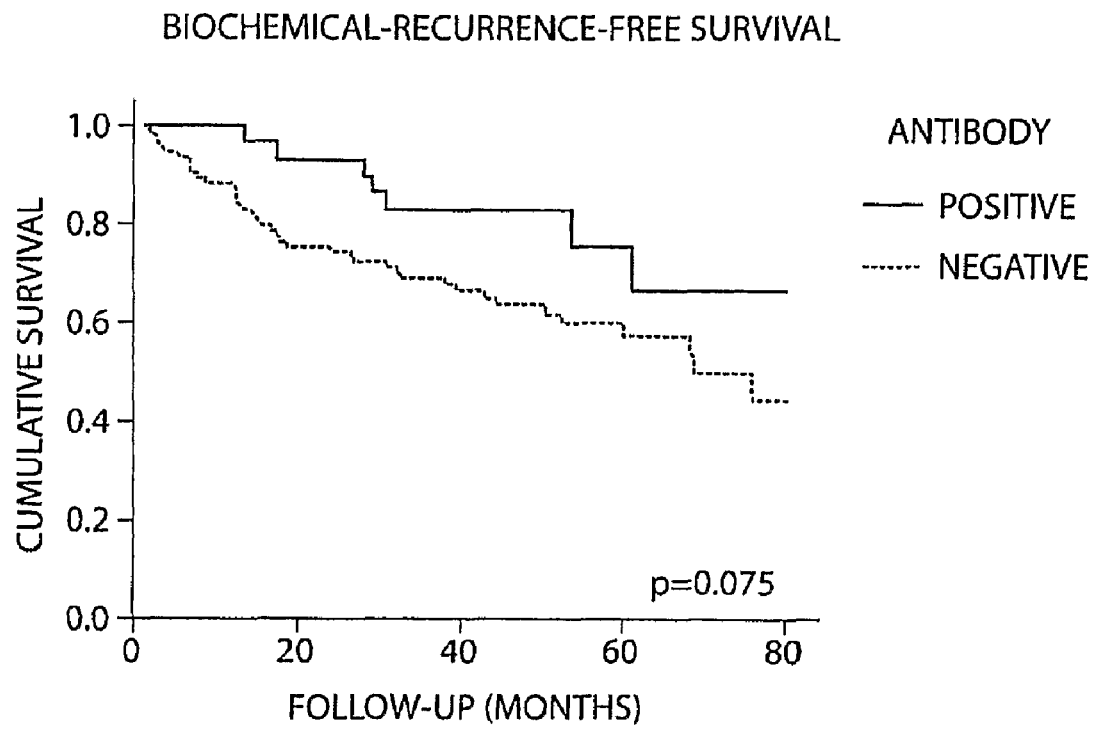
Figure 8B:
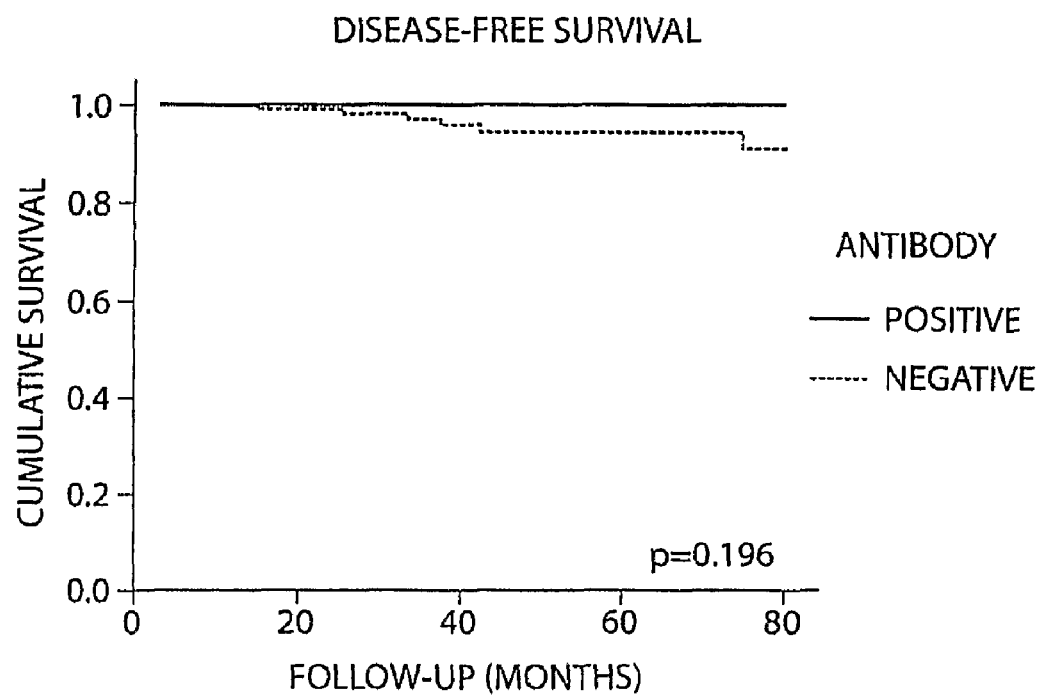

FIG. 8 provides two graphs showing survival curves according to the presence of an anti-CTSP-1 humoral immune response using two parameters: FIG. 8A depicts biochemical-recurrence-free survival; and FIG. 8B depicts disease-free survival.

BRIEF DESCRIPTION OF THE SEQUENCES

SEQ ID NO:1 is the nucleotide sequence of CTSP-1 variant a (complete mRNA sequence, 3915 bp).

SEQ ID NO:2 is the nucleotide sequence of CTSP-1 variant b (without exon 5).

SEQ ID NO:3 is the nucleotide sequence of CTSP-1 variant c (without exon 4).

SEQ ID NO:4 is the nucleotide sequence of CTSP-1 variant d (without exon 7).

SEQ ID NO:5 is the nucleotide sequence of CTSP-1 variant e (without exons 4 and 5).

SEQ ID NO:6 is the nucleotide sequence of CTSP-1 variant f (without exons 5 and 7).

SEQ ID NO:7 is the nucleotide sequence of CTSP-1 variant g (without exons 4 and 7).

SEQ ID NO:8 is the nucleotide sequence of CTSP-1 variant h (without exons 4, 5 and 7).

SEQ ID NO:9 is the nucleotide sequence of CTSP-2 (complete mRNA sequence, 3923 bp).

SEQ ID NO:10 is the nucleotide sequence of CTSP-3 (complete mRNA sequence, 3938 bp).

SEQ ID NO: 11 is the nucleotide sequence of CTSP-4 (complete mRNA sequence, 3907 bp).

SEQ ID NO:12 is the nucleotide sequence of C21orf99 (complete mRNA sequence, 579 bp).

SEQ ID NO: 13 is the amino acid sequence of polypeptide encoded by the open reading frame of CTSP-1 variant a (115 aa).

SEQ ID NO: 14 is the amino acid sequence of polypeptide encoded by the open reading frame of CTSP-1 variant b (115 aa).

SEQ ID NO: 15 is the amino acid sequence of polypeptide encoded by the open reading frame of CTSP-1 variant c (117 aa).

SEQ ID NO: 16 is the amino acid sequence of polypeptide encoded by the open reading frame of CTSP-1 variant d (115 aa).

SEQ ID NO: 17 is the amino acid sequence of polypeptide encoded by the open reading frame of CTSP-1 variant e (195 aa).

SEQ ID NO: 18 is the amino acid sequence of polypeptide encoded by the open reading frame of CTSP-1 variant f (115 aa).

SEQ ID NO: 19 is the amino acid sequence of polypeptide encoded by the open reading frame of CTSP-1 variant g (117 aa).

SEQ ID NO:20 is the amino acid sequence of polypeptide encoded by the open reading frame of CTSP-1 variant h (202 aa). This is the longest of the polypeptides encoded by CTSP-1 variants, and was used for generation of CTSP-1 recombinant protein.

SEQ ID NO:21 is the amino acid sequence of polypeptide encoded by the open reading frame of CTSP-2 (115 aa).

SEQ ID NO:22 is the amino acid sequence of polypeptide encoded by the open reading frame of CTSP-3 (115 aa).

SEQ ID NO:23 is the amino acid sequence of polypeptide encoded by the open reading frame of CTSP-4 (115 aa).

SEQ ID NO:24 is the amino acid sequence of polypeptide encoded by the open reading frame of C21 orf99 (78 aa).

SEQ ID NO:25 is the nucleotide sequence of the CTSP-F1 primer.

SEQ ID NO:26 is the nucleotide sequence of the CTSP-R1 primer.

SEQ ID NO:27 is the nucleotide sequence of the CTSP-F2 primer.

SEQ ID NO:28 is the nucleotide sequence of the CTSP-R2 primer.

SEQ ID NO:29 is the nucleotide sequence of the SP-RACE primer.

SEQ ID NO:30 is the nucleotide sequence of the Adaptor primer.

SEQ ID NO:31 is the nucleotide sequence of the SP-RACE-3N primer.

SEQ ID NO:32 is the nucleotide sequence of the Adaptor-N primer.

SEQ ID NO:33 is the nucleotide sequence of the CT1F primer.

SEQ ID NO:34 is the nucleotide sequence of the CT1R primer.

SEQ ID NO:35 is the nucleotide sequence of the CT2F primer.

SEQ ID NO:36 is the nucleotide sequence of the CT2R primer.

SEQ ID NO:37 is the nucleotide sequence of the CT3F primer.

SEQ ID NO:38 is the nucleotide sequence of the CT3R primer.

SEQ ID NO:39 is the nucleotide sequence of the CT4F primer.

SEQ ID NO:40 is the nucleotide sequence of the CT4R primer.

SEQ ID NO:41 is the nucleotide sequence of the CTSP1RecF primer.

SEQ ID NO:42 is the nucleotide sequence of the CTSP1RecR primer.

SEQ ID NO:43 is the nucleotide sequence of CTSP-1 exon 1.

SEQ ID NO:44 is the nucleotide sequence of CTSP-1 exon 2.

SEQ ID NO:45 is the nucleotide sequence of CTSP-1 exon 3.

SEQ ID NO:46 is the nucleotide sequence of CTSP-1 exon 4.

SEQ ID NO:47 is the nucleotide sequence of CTSP-1 exon 5.

SEQ ID NO:48 is the nucleotide sequence of CTSP-1 exon 6.

SEQ ID NO:49 is the nucleotide sequence of CTSP-1 exon 7.

SEQ ID NO:50 is the nucleotide sequence of CTSP-1 exon 8.

SEQ ID NO:51 is the nucleotide sequence of CTSP-1 exon 9 (contains a LTR repeat).

SEQ ID NO:52 is the nucleotide sequence of CTSP-1 exon 10.

SEQ ID NO:53 is the nucleotide sequence of CTSP-1 exon 11.

SEQ ID NO:54 is the nucleotide sequence of CTSP-1 exon 12 (contains an Alu repeat).

SEQ ID NO:55 is the nucleotide sequence of CTSP-1 exon 13.

SEQ ID NO:56 is the nucleotide sequence of CTSP-1 exon 14.

SEQ ID NO:57 is the nucleotide sequence of CTSP-1 exon 15.

DETAILED DESCRIPTION OF THE INVENTION

The invention relates to CTSP-1 antigen polypeptides provided herein and the nucleic acid molecules that encode them, as well as related nucleic acid and polypeptide sequences corresponding to the related genes CTSP-2, CTSP-3 and CTSP-4. The invention further relates to the use of the nucleic acid molecules, polypeptides and fragments thereof in methods and compositions for the diagnosis and treatment of cancer.

As used herein, the terms "CTSP nucleic acid", "CTSP polypeptide" and the like refer to a family of nucleic acids and polypeptides that are, or are related by a high degree of sequence identity to SEQ ID NOS: 1-8 (nucleic acid sequence of CTSP-1 and splice variants thereof) or any of SEQ ID NOS: 13-20 (polypeptide sequence of CTSP-1). Thus CTSP nucleic acids include SEQ ID NOs:1-11 (full length sequences), and partial sequences such as exons 1-15 of CTSP-1 (SEQ ID NOs:43-57) and exons of related genes CTSP-2, CTSP-3 and CTSP-4. CTSP polypeptides include SEQ ID NO: 13-23. The polypeptides elicit specific immune responses as is shown in the Examples below, and thus include CSTP polypeptides (including proteins) and fragments of CTSP polypeptides that are recognized by the immune system (e.g., by antibodies and/or T lymphocytes).

In part, the invention relates to CTSP polypeptides as well as the nucleic acid molecules that encode the CTSP polypeptides. As used herein, the "nucleic acid molecules that encode" means the nucleic acid molecules that code for the CTSP polypeptides or fragments thereof, particularly immunogenic fragments. These nucleic acid molecules may be DNA or may be RNA (e.g., mRNA). The CTSP nucleic acid molecules of the invention also encompass variants of the nucleic acid molecules described herein. These variants may be splice variants, some of which are described herein for CTSP-1, or allelic variants of certain sequences provided. Variants of the nucleic acid molecules of the invention are intended to include homologs and alleles which are described further below. Further, as used herein, the term "CTSP molecules" includes CTSP polypeptides and fragments thereof as well as CTSP nucleic acids and fragments (such as exon sequences). In all embodiments, human CTSP polypeptides and the nucleic acid molecules that encode them are preferred.

In one aspect, the invention provides isolated nucleic acid molecules that encode the CTSP polypeptides described herein. The isolated nucleic acid molecules of this aspect of the invention comprise: (a) nucleotide sequences set forth as SEQ ID NOs: 1-11 (b) isolated nucleic acid molecules which hybridize under highly stringent conditions to the nucleic acid molecules of (a) and preferably which code for a CTSP polypeptide, (c) nucleic acid molecules that differ from (a) or (b) due to the degeneracy of the genetic code, and (d) full-length complements of (a), (b) or (c).

As used herein the term "isolated nucleic acid molecule" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein because it is readily manipulable by standard techniques known to those of ordinary skill in the art.

The CTSP nucleic acid molecules of the invention also encompass homologs and alleles which can be identified by conventional techniques. Identification of human and other organisms' homologs of CTSP polypeptides will be familiar to those of skill in the art. In general, nucleic acid hybridization is a suitable method for identification of homologous sequences of another species (e.g., human, cow, sheep, dog, rat, mouse), which correspond to a known sequence. Standard nucleic acid hybridization procedures can be used to identify related nucleic acid sequences of selected percent identity. For example, one can construct a library of cDNAs reverse transcribed from the mRNA of a selected tissue and use the CTSP nucleic acid molecules identified herein to screen the library for related nucleotide sequences. The screening preferably is performed using high-stringency conditions to identify those sequences that are closely related by sequence identity. Nucleic acids so identified can be translated into polypeptides and the polypeptides can be tested for activity.

The term "high stringency" as used herein refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5× SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of the CTSP nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecule and sequencing.

In general, homologs and alleles typically will share at least 90% nucleotide identity and/or amino acid identity to the sequences of CTSP nucleic acids and polypeptides, respectively, in some instances will share at least 95% nucleotide identity and/or amino acid identity, in other instances will share at least 97% nucleotide identity and/or amino acid identity, in other instances will share at least 98% nucleotide identity and/or amino acid identity, and in other instances will share at least 99% nucleotide identity and/or amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using a number of sequence analysis software programs, such as the MacVector sequence analysis software (Accelrys Software Inc., San Diego, Calif.). Watson-Crick complements of the foregoing nucleic acids also are embraced by the invention.

In another aspect of the invention, unique fragments are provided which include unique fragments of the nucleotide sequences of the invention and complements thereof. The invention, in a preferred embodiment, provides unique fragments of SEQ ID NO: 1-11 and 43-57 and complements thereof. A unique fragment is one that is a 'signature' for the larger nucleic acid. It, for example, is long enough to assure that its precise sequence is not found in molecules outside of the nucleic acid molecules that encode the CTSP polypeptides defined above. Those of ordinary skill in the art may apply no more than routine procedures to determine if a fragment is unique within the human genome. In some instances the unique fragment is at least about 5, 6, 7, 8, 9, 10, 11, 12, 13, 14, 15, 16, 17, 18, 19, 20, 25, 30, 35, 40, 45, 50, 75, or 100 amino acids in length.

Unique fragments can be used as probes in Southern blot assays to identify such nucleic acid molecules, or can be used as probes in amplification assays such as those employing the polymerase chain reaction (PCR), including, but not limited to RT-PCR and RT-real-time PCR. As known to those skilled in the art, large probes such as 200 nucleotides or more are preferred for certain uses such as Southern blots, while smaller fragments will be preferred for uses such as PCR. Unique fragments also can be used to produce fusion proteins for generating antibodies or determining binding of the polypeptide fragments, or for generating immunoassay components. Likewise, unique fragments can be employed to produce nonfused fragments of the CTSP polypeptides useful, for example, in the preparation of antibodies and in immunoassays.

In screening for CTSP genes, a Southern blot may be performed using the foregoing conditions, together with a detectably labeled probe (e.g., radioactive or chemiluminescent probes). After washing the membrane to which the DNA is finally transferred, the membrane can be placed against X-ray film or analyzed using a phosphorimager device to detect the radioactive or chemiluminescent signal. In screening for the expression of CTSP nucleic acids, Northern blot hybridizations using the foregoing conditions can be performed on samples taken from cancer patients or subjects suspected of having a condition characterized by abnormal cell proliferation or neoplasia. Amplification protocols such as polymerase chain reaction using primers that hybridize to the sequences presented also can be used for detection of the CTSP genes or expression thereof.

Identification of related sequences can also be achieved using polymerase chain reaction (PCR) and other amplification techniques suitable for cloning related nucleic acid sequences. Preferably, PCR primers are selected to amplify portions of a nucleic acid sequence believed to be conserved (e.g., a catalytic domain, a DNA-binding domain, etc.). Again, nucleic acids are preferably amplified from a tissue-specific library (e.g., testis). One also can use expression cloning utilizing the antisera described herein to identify nucleic acids that encode related antigenic proteins in humans or other species using the SEREX procedure to screen the appropriate expression libraries. (See: Sahin et al., 1995, *Proc. Natl. Acad. Sci. U.S.A.* 92:11810-11813).

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating CTSP polypeptide. Similarly, nucleotide sequence triplets which encode other amino acid residues include, but are not limited to: CCA, CCC, CCG, and CCT (proline codons); CGA, CGC, COG, COT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides (preferably 1-20 nucleotides). In preferred embodiments, these modified nucleic acid molecules and/or the polypeptides they encode retain at least one activity or function of the unmodified nucleic acid molecule and/or the polypeptides, such as antigenicity, receptor binding, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on.

In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of activity or structural relation to the nucleic acids and/or polypeptides disclosed herein. As used herein the terms: "deletion", "addition", and "substitution" mean deletion, addition, and substitution changes to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more nucleic acids of a sequence of the invention.

According to yet another aspect of the invention, an expression vector comprising any of the isolated nucleic acid molecules of the invention, preferably operably linked to a promoter is provided. In a related aspect, host cells transformed or transfected with such expression vectors also are provided. As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids, and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art, e.g., β-galactosidase or alkaline phosphatase, and genes which visibly affect the phenotype of transformed or transfected cells, hosts, colonies or plaques, e.g., green fluorescent protein. Preferred vectors are those capable of autonomous replication and expression of the structural gene products present in the DNA segments to which they are operably joined.

As used herein, a coding sequence and regulatory sequences are said to be "operably joined" when they are covalently linked in such a way as to place the expression or transcription of the coding sequence under the influence or control of the regulatory sequences. As used herein, "operably joined" and "operably linked" are used interchangeably and should be construed to have the same meaning. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region is operably joined to a coding sequence if the promoter region is capable of effecting transcription of that DNA sequence such that the resulting transcript can be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Often, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

It will also be recognized that the invention embraces the use of the CTSP nucleic acid molecules and genomic sequences in expression vectors, as well as to transfect host cells and cell lines, be these prokaryotic, e.g., E. coli, or eukaryotic, e.g., CHO cells, COS cells, yeast expression systems, and recombinant baculovirus expression in insect cells. Especially useful are mammalian cells such as human, mouse, hamster, pig, goat, primate, etc. They may be of a wide variety of tissue types, including mast cells, fibroblasts, oocytes, and lymphocytes, and may be primary cells and cell lines. Specific examples include dendritic cells, peripheral blood leukocytes, bone marrow stem cells and embryonic stem cells. The expression vectors require that the pertinent sequence, i.e., those nucleic acids described supra, be operably linked to a promoter.

The invention, in one aspect, also permits the construction of CTSP gene "knock-outs" and "knock-ins" in cells and in animals, providing materials for studying certain aspects of cancer and immune system responses to cancer.

Expression vectors containing all the necessary elements for expression are commercially available and known to those skilled in the art. Cells are genetically engineered by the introduction into the cells of heterologous DNA or RNA encoding a CTSP polypeptide, a mutant CTSP polypeptide, fragments, or variants thereof. The heterologous DNA or RNA is placed under operable control of transcriptional elements to permit the expression of the heterologous DNA in the host cell.

Preferred systems for mRNA expression in mammalian cells are those such as pcDNA3.1 and pCDM8 (Invitrogen) that contain a selectable marker (which facilitates the selection of stably transfected cell lines) and contain the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1, which stimulates efficiently transcription in vitro. The plasmid is described by Mizushima and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992). The use of the adenovirus as an Adeno.P1A recombinant is described by Warnier et al., in intradermal injection in mice for immunization against P1A (*Int. J. Cancer,* 67:303-310, 1996).

The invention also embraces kits termed expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also includes kits for amplification of a CTSP nucleic acid, including at least one pair of amplification primers which hybridize to a CTSP nucleic acid. The primers preferably are about 12, 13, 14, 15, 16, 17, 18, 19, 20, 21, 22, 23, 24, 25, 26, 27, 28, 29, 30, 31 or 32 nucleotides in length and are non-overlapping to prevent formation of "primer-dimers". One of the primers will hybridize to one strand of the CTSP nucleic acid and the second primer will hybridize to the complementary sand of the CTSP nucleic acid, in an arrangement that permits amplification of the CTSP nucleic acid. Selection of appropriate primer pairs is standard in the art. For example, the selection can be made with assistance of a computer program designed for such a purpose, optionally followed by testing the primers for amplification specificity and efficiency.

The invention, in another aspect provides isolated polypeptides (including whole proteins and partial proteins) encoded by the foregoing CTSP nucleic acids. Examples of the amino acid sequences encoded by the foregoing CTSP nucleic acids are set forth as any of SEQ ID NOs: 13-23. The amino acids of the invention are also intended to encompass amino acid sequences that result from the translation of the nucleic acid sequences provided herein in a different reading frame. In one preferred embodiment of the invention a polypeptide is provided which comprises the polypeptide sequence set forth as any of SEQ ID NOS: 13-20.

Such polypeptides are useful, for example, alone or as fusion proteins to generate antibodies, and as components of an immunoassay or diagnostic assay. Immunogenic CTSP polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Fragments of the immunogenic CTSP polypeptides (including immunogenic peptides) also can be synthesized chemically using well-established methods of peptide synthesis. Thus, fragments of the disclosed polypeptides are useful for eliciting an immune response. In one embodiment fragments of a polypeptide which comprises any of SEQ ID NO: 13-23 that are at least eight amino acids in length and exhibit immunogenicity are provided. In one embodiment fragments of a polypeptide which comprises any of SEQ ID NOS: 13-20 that are at least eight amino acids in length and exhibit immunogenicity are provided.

Fragments of a polypeptide preferably are those fragments that retain a distinct functional capability of the polypeptide. Functional capabilities that can be retained in a fragment of a polypeptide include interaction with antibodies or MHC molecules (e.g. immunogenic fragments), interaction with other polypeptides or fragments thereof, selective binding of nucleic acids or proteins, and enzymatic activity. One important activity is the ability to provoke in a subject an immune response. As will be recognized by those skilled in the art, the size of the fragment that can be used for inducing an immune response will depend upon factors such as whether the epitope recognized by an antibody is a linear epitope or a conformational epitope or the particular MHC molecule that binds to and presents the fragment (e.g., HLA class I or II). Thus, some immunogenic fragments of CTSP polypeptides will consist of longer segments while others will consist of shorter segments, (e.g., about 5, 6, 7, 8, 9, 10, 11 or 12 or more amino acids long, including each integer up to the full length of the CTSP polypeptide). Those skilled in the art are well versed in methods for selecting immunogenic fragments of polypeptides.

The invention embraces variants of the CTSP polypeptides described above. As used herein, a "variant" of a CTSP polypeptide is a polypeptide which contains one or more modifications to the primary amino acid sequence of a CTSP polypeptide. Modifications which create a CTSP polypeptide variant can be made to a CTSP polypeptide 1) to reduce or eliminate an activity of a CTSP polypeptide; 2) to enhance a property of a CTSP polypeptide, such as protein stability in an expression system or the stability of protein-protein binding; 3) to provide a novel activity or property to a CTSP polypeptide, such as addition of an antigenic epitope or addition of a detectable moiety; or 4) to provide equivalent or better binding to a MHC molecule.

Modifications to a CTSP polypeptide are typically made to the nucleic acid which encodes the CTSP polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the CTSP polypeptide amino acid sequence. One of skill in the art will be familiar with methods for predicting the effect on protein conformation of a change in protein sequence, and can thus "design" a variant CTSP polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a CTSP polypeptide can be proposed and tested to determine whether the variant retains a desired conformation.

In general, variants include CTSP polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a CTSP polypeptide by eliminating proteolysis by proteases in an expression system (e.g., dibasic amino acid residues in yeast expression systems in which KEX2 protease activity is present).

Mutations of a nucleic acid which encode a CTSP polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant CTSP polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a CTSP gene or cDNA clone to enhance expression of the polypeptide. The activity of variants of CTSP polypeptides can be tested by cloning the gene encoding the variant CTSP polypeptide into a bacterial or mammalian expression vector, introducing the vector into an appropriate host cell, expressing the variant CTSP polypeptide, and testing for a functional capability of the CTSP polypeptides as disclosed herein. For example, the variant CTSP polypeptide can be tested for reaction with autologous or allogeneic sera as described in the Examples. Preparation of other variant polypeptides may favor testing of other activities, as will be known to one of ordinary skill in the art.

The skilled artisan will also realize that conservative amino acid substitutions may be made in immunogenic CTSP polypeptides to provide functionally equivalent variants, or homologs of the foregoing polypeptides, i.e., the variants retain the functional capabilities of the immunogenic CTSP polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants or homologs of the CTSP polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the CTSP polypeptides disclosed herein and retain the specific antibody-binding characteristics of the antigens.

Likewise, upon determining that a peptide derived from a CTSP polypeptide is presented by an MHC molecule and recognized by antibodies or T lymphocytes (e.g., helper T cells or CTLs), one can make conservative amino acid substitutions to the amino acid sequence of the peptide, particularly at residues which are thought not to be direct contact points with the MHC molecule. For example, methods for identifying functional variants of HLA class II binding peptides are provided in a published PCT application of Strominger and Wucherpfennig (PCT/US96/03182). Peptides bearing one or more amino acid substitutions also can be tested for concordance with known HLA/MHC motifs prior to synthesis using, e.g. the computer program described by D'Amaro and Drijfhout (D'Amaro et al., *Human Immunol.* 43:13-18, 1995; Drijfhout et al., *Human Immunol.* 43:1-12, 1995). The substituted peptides can then be tested for binding to the MHC molecule and recognition by antibodies or T lymphocytes when bound to MHC. These variants can be tested for improved stability and are useful, inter alia, in vaccine compositions.

Conservative amino-acid substitutions in the amino acid sequence of CTSP polypeptides to produce functionally equivalent variants of CTSP polypeptides typically are made by alteration of a nucleic acid encoding a CTSP polypeptide. Such substitutions can be made by a variety of methods known to one of ordinary skill in the art. For example, amino acid substitutions may be made by PCR-directed mutation, site-directed mutagenesis according to the method of Kunkel (Kunkel, 1985, *Proc. Nat. Acad. Sci. U.S.A.* 82:488-492), or by chemical synthesis of a gene encoding a CTSP polypeptide. Where amino acid substitutions are made to a small unique fragment of a CTSP polypeptide, such as an antigenic epitope recognized by autologous or allogeneic sera or T lymphocytes, the substitutions can be made by directly synthesizing the peptide. The activity of functionally equivalent variants of CTSP polypeptides can be tested by cloning the gene encoding the altered CTSP polypeptide into a bacterial or mammalian expression vector, introducing the vector into an appropriate host cell, expressing the altered polypeptide, and testing for a functional capability of the CTSP polypeptides as disclosed herein. Peptides that are chemically synthesized can be tested directly for function, e.g., for binding to antisera recognizing associated antigens.

The invention as described herein has a number of uses, some of which are described elsewhere herein. In one aspect of the invention a method of identifying polypeptides homologous to CTSP is provided. Novel CTSP polypeptides can be identified by obtaining a biological sample from a subject, determining the reactivity of the biological sample with one or more known CTSP polypeptides (as described herein), and subsequently using the reactive biological sample to screen an expression library to identify novel CTSP polypeptides.

As used herein, a "subject" is preferably a human, non-human primate, cow, horse, pig, sheep, goat, dog, cat or rodent. In all embodiments, human subjects are preferred. In some embodiments, the subject is suspected of having cancer or has been diagnosed with cancer. Cancers in which the CTSP nucleic acid or polypeptide are differentially expressed include cancers of the breast, colon, esophagus, glioblastoma, lung, melanoma, prostate, stomach, thyroid, and uterus.

As used herein, a biological sample includes, but is not limited to: tissue, cells, and/or body fluid (e.g., serum, blood, lymph node fluid, etc.). The fluid sample may include cells and/or fluid. The tissue and cells may be obtained from a subject or may be grown in culture (e.g., from a cell line). As used herein, a biological sample is body fluid, tissue or cells obtained from a subject using methods well-known to those of ordinary skill in the related medical arts. Typically, a biological sample may be obtained by collecting a blood sample or a biopsy sample from a subject. The biological sample can include tumor tissue or cells, normal tissue or cells, or combinations thereof.

The invention in another aspect permits the isolation of the cancer-associated antigens described herein. A variety of methodologies well-known to the skilled practitioner can be utilized to obtain isolated cancer-associated antigens. The proteins may be purified from cells which naturally produce the protein by chromatographic means or immunological recognition. Alternatively, an expression vector may be introduced into cells to cause production of the protein. In another method, mRNA transcripts may be microinjected or otherwise introduced into cells to cause production of the encoded protein. Translation of mRNA in cell-free extracts such as the reticulocyte lysate system also may be used to produce the protein. Those skilled in the art also can readily follow known methods for isolating cancer-associated antigens. These include, but are not limited to, chromatographic techniques such as immunochromatography, HPLC, size-exclusion chromatography, ion-exchange chromatography, and immune-affinity chromatography.

The invention also involves diagnosing or monitoring cancer in subjects by determining the presence of an immune response to one or more CTSP polypeptides of the invention. In preferred embodiments, this determination is performed by assaying a bodily fluid obtained from the subject, preferably serum, blood, or lymph node fluid for the presence of antibodies against the CTSP polypeptides described herein. This determination may also be performed by assaying a tissue or cells from the subject for the presence of one or more CTSP polypeptides (or nucleic acid molecules that encode these polypeptides) described herein. In another embodiment, the presence of antibodies against at least one additional cancer-associated antigen or cancer-testis antigen is determined for diagnosis of cancer. This determination may also be performed by assaying a tissue or cells from the subject for the presence of the CTSP polypeptides described herein.

Measurement of the expression of CTSP polypeptides or nucleic acid molecules, or the immune response against one of the CTSP polypeptides, over time by sequential determinations permits monitoring of the disease and/or the effects of a course of treatment. For example, a sample, such as serum, blood, or lymph node fluid, may be obtained from a subject, tested for expression of CTSP molecules or an immune response to one of the CTSP polypeptides, and at a second, subsequent time, another sample, may be obtained from the subject and similarly tested. The results of the first and second (or subsequent) tests can be compared as a measure of the onset, regression or progression of cancer, or, if cancer treatment was undertaken during the interval between obtaining the samples, the effectiveness of the treatment may be evaluated by comparing the results of the two tests. In preferred embodiments of immune response testing, the CTSP polypeptides are bound to a substrate and/or the immune response to the CTSP polypeptides is determined with ELISA. Other methods will be apparent to one of skill in the art.

Diagnostic methods of the invention also involve determining the aberrant expression of one or more of the CTSP polypeptides described herein or the nucleic acid molecules that encode them. Such determinations can be carried out via any standard nucleic acid assay, including the polymerase chain reaction or assaying with hybridization probes, which may be labeled, or by assaying biological samples with binding partners (e.g., antibodies) for CTSP polypeptides.

The diagnostic methods of the invention can be used to detect the presence of a disorder associated with aberrant expression of a CTSP molecule (e.g., onset of the disorder), as well as to assess the progression and/or regression of the disorder such as in response to treatment (e.g., chemotherapy, radiation). According to this aspect of the invention, the method for diagnosing a disorder characterized by aberrant expression of a CTSP molecule involve: detecting expression of a CTSP molecule in a first biological sample obtained from a subject, wherein differential expression of the CTSP molecule compared to a control sample indicates that the subject has a disorder characterized by aberrant expression of a CTSP molecule, such as cancer.

As described herein, CTSP molecules are expressed in testis tissue and certain other normal tissues (brain, fetal brain and spinal cord for CTSP-2). Therefore, in all of the diagnostic methods described herein, the biological sample preferably does not contain testis cells or testis tissue in order to avoid false-positive results. For CTSP-2, the sample preferably also does not contain brain, fetal brain or spinal cord cells or tissue.

As used herein, "aberrant expression" of a CTSP molecule is intended to include any expression that is statistically significant different from the expected (e.g., normal or baseline) amount of expression. For example, expression of a CTSP molecule (i.e., CTSP polypeptides or the nucleic acid molecules that encode them) in a tissue that is not expected to express the CTSP molecule would be included in the definition of "aberrant expression". Likewise, expression of the CTSP molecule that is determined to be expressed at a significantly higher or lower level than expected is also included. Therefore, a determination of the level of expression of one or more of the CTSP polypeptides and/or the nucleic acids that encode them is diagnostic of cancer if the level of expression is above a baseline level determined for that tissue type. The baseline level of expression can be determined using standard methods known to those of skill in the art. Such methods include, for example, assaying a number of histologically normal tissue samples (preferably not testis) from subjects that are clinically normal (i.e. do not have clinical signs of cancer in that tissue type) and determining the mean level of expression for the samples.

The level of expression of the nucleic acid molecules of the invention or the polypeptides they encode can indicate cancer in the tissue when the level of expression is significantly more in the tissue than in a control sample. In some embodiments, a level of expression in the tissues that is at least about 5%, 10%, 20%, 30%, 40%, 50%, 60%, 70%, 80%, 90%, 100%, 150%, 200%, 250%, 300%, 400%, or 500% more than the level of expression in the control tissue indicates cancer in the tissue.

As used herein the term "control" means predetermined values, and also means samples of materials tested in parallel with the experimental materials. Examples include samples from control populations, biopsy samples taken from tissue adjacent to a biopsy sample suspected of being cancerous and control samples generated through manufacture to be tested in parallel with the experimental samples.

As used herein the term "control" includes positive and negative controls which may be a predetermined value that can take a variety of forms. The control(s) can be a single cut-off value, such as a median or mean, or can be established based upon comparative groups, such as in groups having normal amounts of CTSP molecules of the invention and groups having abnormal amounts of CTSP molecules of the invention. Another example of a comparative group is a group having a particular disease, condition and/or symptoms and a group without the disease, condition and/or symptoms. Another comparative group is a group with a family history of a particular disease and a group without such a family history of the particular disease. The predetermined control value can be arranged, for example, where a tested population is divided equally (or unequally) into groups, such as a low-risk group, a medium-risk group and a high-risk group or into quadrants or quintiles, the lowest quadrant or quintile being individuals with the lowest risk or lowest expression levels of a CTSP molecule of the invention that is up-regulated in cancer and the highest quadrant or quintile being individuals with the highest risk or highest expression levels of a CTSP molecule of the invention that is up-regulated in cancer.

The predetermined value of a control will depend upon the particular population selected. For example, an apparently healthy population will have a different "normal" CTSP molecule expression level range than will a population which is known to have a condition characterized by aberrant expression of the CTSP molecule. Accordingly, the predetermined value selected may take into account the category in which an individual falls. Appropriate ranges and categories can be selected with no more than routine experimentation by those of ordinary skill in the art. Typically the control will be based on apparently healthy individuals in an appropriate age bracket. As used herein, the term "increased expression" means a higher level of expression relative to a selected control.

The invention involves in some aspects diagnosing or monitoring cancer by determining the level of expression of one or more CTSP nucleic acid molecules and/or determining the level of expression of one or more CTSP polypeptides they encode. In some important embodiments, this determination is performed by assaying a tissue sample from a subject for the level of expression of one or more CTSP nucleic acid molecules or for the level of expression of one or more CTSP polypeptides encoded by the nucleic acid molecules of the invention.

The expression of the molecules of the invention may be determined using routine methods known to those of ordinary skill in the art. These methods include, but are not limited to: direct RNA amplification, reverse transcription of RNA to cDNA, real-time RT-PCR, amplification of cDNA, hybridization, and immunologically based assay methods, which include, but are not limited to immunohistochemistry, antibody sandwich capture assay, ELISA, and enzyme-linked immunospot assay (EliSpot assay). For example, the determination of the presence of level of nucleic acid molecules of the invention in a subject or tissue can be carried out via any standard nucleic acid determination assay, including the polymerase chain reaction, or assaying with labeled hybridization probes. Such hybridization methods include, but are not limited to microarray techniques.

These methods of determining the presence and/or level of the molecules of the invention in cells and tissues may include use of labels to monitor the presence of the molecules of the invention. Such labels may include, but are not limited to, radiolabels or chemiluminescent labels, which may be utilized to determine whether a molecule of the invention is expressed in a cell or tissue, and to determine the level of expression in the cell or tissue. For example, a fluorescently labeled or radiolabeled antibody that selectively binds to a polypeptide of the invention may be contacted with a tissue or cell to visualize the polypeptide in vitro or in vivo. These and other in vitro and in vivo imaging methods for determining the presence of the nucleic acid and polypeptide molecules of the invention are well known to those of ordinary skill in the art.

The invention, therefore, also involves the use of agents such as polypeptides that bind to CTSP polypeptides. Such agents can be used in methods of the invention including the diagnosis and/or treatment of cancer. Such binding agents can be used, for example, in screening assays to detect the presence or absence of CTSP polypeptides and can be used in quantitative binding assays to determine levels of expression in biological samples and cells. Such agents also may be used to inhibit the native activity of the CTSP polypeptides, for example, by binding to such polypeptides.

According to this aspect, the binding polypeptides bind to an isolated nucleic acid or protein of the invention, including unique fragments thereof. Preferably, the binding polypeptides bind to a CTSP polypeptide, or a unique fragment thereof.

In preferred embodiments, the binding polypeptide is an antibody or antibody fragment, more preferably, an Fab or $F(ab)_2$ fragment of an antibody. Typically, the fragment includes a CDR3 region that is selective for the CTSP polypeptide. Any of the various types of antibodies can be used for this purpose, including polyclonal antibodies, monoclonal antibodies, humanized antibodies, and chimeric antibodies.

Thus, the invention provides agents which bind to CTSP polypeptides encoded by CTSP nucleic acid molecules of the invention, and in certain embodiments preferably to unique fragments of the CTSP polypeptides. Such binding partners can be used in screening assays to detect the presence or absence of a CTSP polypeptide and in purification protocols to isolate such CTSP polypeptides. Likewise, such binding partners can be used to selectively target drugs, toxins or other molecules (including detectable diagnostic molecules) to cells which express CTSP polypeptides. In this manner, for example, cells present in solid or non-solid tumors which express CTSP polypeptides can be treated with cytotoxic compounds that are selective for the CTSP molecules (nucleic acids and/or antigens). Such binding agents also can be used to inhibit the native activity of the CTSP polypeptide, for example, to further characterize the functions of these molecules.

The antibodies of the present invention thus are prepared by any of a variety of methods, including administering a protein, fragments of a protein, cells expressing the protein or fragments thereof and the like to an animal to induce polyclonal antibodies. The present invention also provides methods of producing monoclonal antibodies to the CTSP molecules of the invention described herein. The production of monoclonal antibodies is performed according to techniques well known in the art. As detailed herein, such antibodies may be used for example to identify tissues expressing protein or to purify protein. Antibodies also may be coupled to specific labeling agents or imaging agents, including, but not limited to a molecule preferably selected from the group consisting of fluorescent, enzyme, radioactive, metallic, biotin, chemiluminescent, bioluminescent, chromophore, or colored, etc. In some aspects of the invention, a label may be a combination of the foregoing molecule types.

Significantly, as is well-known in the art, only a small portion of an antibody molecule, the paratope, is involved in the binding of the antibody to its epitope (see, in general, Clark, W. R., 1986, *The Experimental Foundations of Modern Immunology*, Wiley & Sons, Inc., New York; Roitt, I., 1991, *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDR5, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816, 567, 5,225,539, 5,585,089, 5,693,762, and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')2, Fab, Fv, and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies, domain antibodies and heavy chain antibodies (Ablynx NV, Ghent, Belgium).

Thus, the invention involves polypeptides of numerous size and type that bind specifically to CTSP polypeptides. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptides and non-peptide synthetic moieties.

The CTSP polypeptides of the invention can be used to screen peptide libraries, including phage display libraries, to identify and select peptide binding partners of the CTSP molecules of the invention. Such molecules can be used, as described, for screening assays, for diagnostic assays, for purification protocols or for targeting drugs, toxins and/or labeling agents (e.g., radioisotopes, fluorescent molecules, etc.) to cells which express CTSP molecules such as cancer cells which have aberrant CTSP expression.

Phage display can be particularly effective in identifying binding peptides useful according to the invention. Briefly, one prepares a phage library (using e.g., m13, fd, or lambda phage), displaying inserts from 4 to about 80 amino acid residues using conventional procedures. The inserts may represent, for example, a completely degenerate or biased array. One then can select phage-bearing inserts which bind to the CTSP polypeptide. This process can be repeated through several cycles of reselection of phage that bind to the CTSP polypeptide. Repeated rounds lead to enrichment of phage bearing particular sequences. DNA sequence analysis can be conducted to identify the sequences of the expressed polypeptides. The minimal linear portion of the sequence that binds to the CTSP polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the CTSP polypeptides.

As detailed herein, the foregoing antibodies and other binding molecules may be used to identify tissues with normal or aberrant expression of a CTSP polypeptide. Antibodies also may be coupled to specific diagnostic labeling agents for imaging of cells and tissues with normal or aberrant CTSP polypeptide expression or to therapeutically useful agents according to standard coupling procedures. As used herein, "therapeutically useful agents" include any therapeutic molecule which desirably is targeted selectively to a cell or tissue selectively with an aberrant CTSP expression.

Diagnostic agents for in vivo use include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99, iodine-131 and indium-III, and nuclides for nuclear magnetic resonance such as fluorine and gadolinium. Other diagnostic agents useful in the invention will be apparent to one of ordinary skill in the art.

The antibodies of the present invention can also be used to therapeutically target CTSP polypeptides. In one embodiment, antibodies can be used to target CTSP antigens expressed on the cell surface, such as CTSP peptides presented by MHC molecules. This can be accomplished, for example, by raising antibodies that recognize the complex of CTSP peptides and MHC molecules.

These antibodies can be linked not only to a detectable marker but also an antitumor agent or an immunomodulator. Antitumor agents can include cytotoxic agents and agents that act on tumor neovasculature. Detectable markers include, for example, radioactive or fluorescent markers. Cytotoxic agents include cytotoxic radionuclides, chemical toxins and protein toxins.

The cytotoxic radionuclide or radiotherapeutic isotope preferably is an alpha-emitting isotope such as $^{225}$Ac, $^{211}$At, $^{212}$Bi, $^{213}$Bi, $^{212}$Pb, $^{224}$Ra or $^{223}$Ra. Alternatively, the cytotoxic radionuclide may a beta-emitting isotope such as $^{186}$Rh, $^{188}$Rh, $^{177}$Lu, $^{90}$Y, $^{131}$I, $^{67}$Cu, $^{64}$Cu, $^{153}$Sm or $^{166}$Ho. Further, the cytotoxic radionuclide may emit Auger and low energy electrons and include the isotopes $^{125}$I, $^{123}$I or $^{77}$Br.

Suitable chemical toxins or chemotherapeutic agents include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Other antineoplastic agents that may be conjugated to the antibodies of the present invention include dolastatins (U.S. Pat. Nos. 6,034,065 and 6,239,104) and derivatives thereof. Of particular interest is dolastatin 10 (dolavaline-valine-olaisoleuine-dolaproine-dolaphenine) and the derivatives auristatin PHE (dolavaline-valine-dolaisoleuine-dolaproine-phenylalanine-methyl ester) (Pettit, G. R. et al., 1998, *Anticancer Drug Des.* 13(4):243-277; Woyke, T. et al., 2001, *Antimicrob. Agents Chemother.* 45(12):3580-3584), and aurastatin E and the like. Toxins that are less preferred in the compositions and methods of the invention include poisonous lectins, plant toxins such as ricin, abrin, modeccin, botulinum and diphtheria toxins. Of course, combinations of the various toxins could also be coupled to one antibody molecule thereby accommodating variable cytotoxicity. Other chemotherapeutic agents are known to those skilled in the art.

Agents that act on the tumor vasculature can include tubulin-binding agents such as combrestatin A4 (Griggs et al., 2001, *Lancet Oncol.* 2:82), angiostatin and endostatin (reviewed in Rosen, 2000, *Oncologist* 5:20, incorporated by reference herein) and interferon inducible protein 10 (U.S. Pat. No. 5,994,292). A number of antiangiogenic agents currently in clinical trials are also contemplated. Agents currently in clinical trials include: 2ME2, Angiostatin, Angiozyme, Anti-VEGF RhuMAb, Apra (CT-2584), Avicine, Benefin, BMS275291, Carboxyamidotriazole, CC4047, CC5013, CC7085, CDC801, CGP41251 (PKC 412), CM101, Combretastatin A-4 Prodrug, EMD 121974, Endostatin, Flavopiridol, Genistein (GCP), Green Tea Extract, IM-862, ImmTher, Interferon alpha, Interleukin-12, Iressa (ZD1839), Marimastat, Metastat (Col-3), Neovastat, Octreotide, Paclitaxel, Penicillamine, Photofrin, Photopoint, PI-88, Prinomastat (AG-3340), PTK787 (ZK22584), R0317453, Solimastat, Squalamine, SU 101, SU 5416, SU-6668, Suradista (FCE 26644), Suramin (Metaret), Tetrathiomolybdate, Thalidomide, TNP470 and Vitaxin. Additional antiangiogenic agents are described by Kerbel, 2001, *J. Clin. Oncol.* 19(18s):45s-51s, which is incorporated by reference herein. Immunomodulators suitable for conjugation to the antibodies include α-interferon, γ-interferon, and tumor necrosis factor alpha (TNFα).

The coupling of one or more toxin molecules to the antibody is envisioned to include many chemical mechanisms, for instance covalent binding, affinity binding, intercalation, coordinate binding, and complexation. The toxic compounds used to prepare the immunotoxins are attached to the antibodies or antigen-binding fragments thereof by standard protocols known in the art.

In other aspects of the invention, the CTSP molecules and the antibodies and other binding molecules, as described herein, can be used for the treatment of disorders. When "disorder" is used herein, it refers to any pathological condition where the CTSP polypeptides are aberrantly expressed. An example of such a disorder is cancer, with breast cancer, lung cancer, colon cancer, prostate cancer, esophageal cancer, brain cancers such as glioblastoma, melanoma, stomach cancer, thyroid cancer, uterine cancer, ovarian cancer, renal cancer, sarcoma, leukemia, lymphoma, gastric cancer, glioma, bladder cancer, and hepatoma.

Conventional treatment for cancer may include, but is not limited to: surgical intervention, chemotherapy, radiotherapy, and adjuvant systemic therapies. In one aspect of the invention, treatment may include administering binding polypeptides such as antibodies that specifically bind to the CTSP polypeptide. These binding polypeptides can be optionally linked to one or more detectable markers, antitumor agents or immunomodulators as described above.

Cancer treatment, in another aspect of the invention may include administering antisense molecules or RNAi molecules to reduce expression level and/or function level of CTSP polypeptides of the invention in the subject in cancers where a CTSP molecule is up-regulated. The use of RNA interference or "RNAi" involves the use of double-stranded RNA (dsRNA) to block gene expression. (see: Sui G et al., 2002, *Proc Natl. Acad. Sci U.S.A.* 99:5515-5520). Methods of applying RNAi strategies in embodiments of the invention would be understood by one of ordinary skill in the art.

CTSP polypeptides as described herein, can also be used in one aspect of the invention to induce or enhance an immune response. For example, the CTSP polypeptides of the invention may be used to stimulate lymphocytes, eliciting a B cell response and/or T cell response. Non-limiting examples of T cell responses include CD4+ T cell responses and CD8+ cell responses. Some therapeutic approaches based upon the disclosure are premised on a response by a subject's immune system, leading to lysis of antigen presenting cells, such as cancer cells which present one or more CTSP polypeptides of the invention. One such approach is the administration of autologous CTLs specific to a CTSP polypeptide/MHC complex to a subject with abnormal cells of the phenotype at issue. It is within the ability of one of ordinary skill in the art to develop such CTLs in vitro. An example of a method for T cell differentiation is presented in International Application number PCT/US96/05607. Generally, a sample of cells taken from a subject, such as blood cells, are contacted with a cell presenting the complex and capable of provoking CTLs to proliferate. The target cell can be a transfectant, such as a COS cell. These transfectants present the desired complex of their surface and, when combined with a CTL of interest, stimulate its proliferation. COS cells are widely available, as are other suitable host cells. Specific production of CTL clones is well known in the art. The clonally expanded autologous CTLs then are administered to the subject.

Another method for selecting antigen-specific CTL clones has recently been described (Altman et al., 1996, *Science* 274:94-96; Dunbar et al., 1998, *Curr. Biol.* 8:413-416), in which fluorogenic tetramers of MHC class I molecule/peptide complexes are used to detect specific CTL clones. Briefly, soluble MHC class I molecules are folded in vitro in the presence of $\beta_2$-microglobulin and a peptide antigen which binds the class I molecule. After purification, the MHC/peptide complex is purified and labeled with biotin. Tetramers are formed by mixing the biotinylated peptide-MHC complex with labeled avidin (e.g., phycoerythrin) at a molar ratio or 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein.

To detail a therapeutic methodology, referred to as adoptive transfer (Greenberg, 1986, *J. Immunol.* 136(5): 1917; Riddel et al., 1992, *Science* 257: 238; Lynch et al., 1991, *Eur. J. Immunol.* 21: 1403-1410; Kast et al., 1989, *Cell* 59: 603-614), cells presenting the desired complex (e.g., dendritic cells) are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/cancer associated antigen complex. This can be determined very easily, as the art is very familiar with methods for identifying cells which present a particular HLA molecule, as well as how to identify cells expressing DNA of the pertinent sequences, in this case a CTSP polypeptide sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a CTSP polypeptide is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach is the use of non-proliferative cells expressing the complex. The cells used in this approach may be those that normally express the complex, such as irradiated tumor cells or cells transfected with one or both of the genes necessary for presentation of the complex (i.e., the antigenic peptide and the presenting MHC molecule). Chen et al. (*Proc. Natl. Acad. Sci. U.S.A.* 88: 110-114, 1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. For example, nucleic acids which encode a CTSP polypeptide may be operably linked to promoter and enhancer sequences which direct expression of the CTSP polypeptide in certain tissues or cell types. The nucleic acid may be incorporated into an expression vector.

Expression vectors may be unmodified extrachromosomal nucleic acids, plasmids or viral genomes constructed or modified to enable insertion of exogenous nucleic acids, such as those encoding CTSP polypeptide, as described elsewhere herein. Nucleic acids encoding a CTSP polypeptide also may be inserted into a retroviral genome, thereby facilitating integration of the nucleic acid into the genome of the target tissue or cell type. In these systems, the gene of interest is carried by a microorganism, e.g., a Vaccinia virus, pox virus, herpes simplex virus, retrovirus or adenovirus, and the materials de facto "infect" host cells. The cells which result present the complex of interest, and are recognized by autologous CTLs, which then proliferate.

A similar effect can be achieved by combining the CTSP polypeptide or a stimulatory fragment thereof with an adjuvant to facilitate incorporation into antigen presenting cells in vivo. The CTSP polypeptide is processed to yield the peptide partner of the MHC molecule while a CTSP fragment may be presented without the need for further processing. Generally, subjects can receive an intradermal injection of an effective amount of the CTSP polypeptide. Initial doses can be followed by booster doses, following immunization protocols standard in the art. Preferred CTSP polypeptides include those found to react with allogeneic cancer antisera, shown in the examples below.

The invention involves the use of various materials disclosed herein to "immunize" subjects or as "vaccines". As used herein, "immunization" or "vaccination" means increasing or activating an immune response against an antigen. It does not require elimination or eradication of a condition but rather contemplates the clinically favorable enhancement of an immune response toward an antigen. Generally accepted animal models, can be used for testing of immunization against cancer using a CTSP molecule. For example, human cancer cells can be introduced into a mouse to create a tumor, and one or more CTSP polypeptides or fragments thereof can be delivered, optionally combined with one or more adjuvants and/or cytokines to boost the immune response. The effect on the cancer cells (e.g., reduction of tumor size) can be assessed as a measure of the effectiveness of the CTSP immunization. Testing of the foregoing animal model using other methods for immunization include the administration of one or more CTSP nucleic acids or fragments derived therefrom.

Methods for immunization, including formulation of a vaccine composition and selection of doses, route of administration and the schedule of administration (e.g. primary and one or more booster doses), are well known in the art. The tests also can be performed in humans, where the end point is to test for the presence of enhanced levels of circulating CTLs against cells bearing the antigen, to test for levels of circulating antibodies against the antigen, to test for the presence of cells expressing the antigen and so forth.

As part of the immunization compositions, one or more CTSP polypeptides or immunogenic fragments thereof are administered with one or more adjuvants to induce an immune response or to increase an immune response. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella minnesota* Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); QS-7, QS-17, QS-18, and QS-L1 (So et al., 1997, *Mol. Cells.* 7:178-186); incomplete Freund's adjuvant; complete Freund's adjuvant; montanide; alum; CpG oligonucleotides (see e.g., Kreig et al., 1995, *Nature* 374:546-9); and various water-in-oil emulsions prepared from biodegradable oils such as squalene and/or tocopherol. Preferably, the antigens are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 μg to about 100 μg. Other adjuvants are known in the art and can be used in the invention (see, e.g., Goding, *Monoclonal Antibodies: Principles and Practice,* 2nd Ed., 1986). Methods for the preparation of mixtures or emulsions of polypeptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., Science 268: 1432-1434, 1995), GM-CSF and IL-18. Thus cytokines can be administered in conjunction with antigens and adjuvants to increase the immune response to the antigens.

There are a number of immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng P. et al., 1998, *Proc. Natl. Acad. Sci U.S.A.* 95 (11):6284-6289).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., 1995, *J. Immunol,* 154:5637-5648). Tumor cell transfection with B7 has been discussed in relation to in vitro CTL expansion for adoptive transfer immunotherapy by Wang et al., (*J. Immunol.,* 19:1-8, 1986). Other delivery mechanisms for the B7 molecule would include nucleic acid (naked DNA) immunization (Kim J., et al., 1997, *Nat. Biotechnol.,* 15(7):641-646) and recombinant viruses such as adeno and pox (Wendtner et al., 1997, *Gene Ther.,* 4(7):726-735). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., 1999, *Nature* 397:263-266).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., 1997, *J. Immunol.* 158:637-642; Fenton et al., 1998, *J. Immunother.,* 21(2):95-108).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B71CD28 costimulatory interaction (Fenton et al., 1998, *J. Immunother.,* 21(2):95-108). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., 1998, *Nature* 393:474; Bennett et al., 1998, *Nature* 393:478; Schoenberger et al., 1998, *Nature* 393:480). This mechanism of this costimulatory signal is likely to involve upregulation of B7 and associated W6/IL-12 production by the DC (APC). The CD40-CD40L interaction thus complements the signal 1 (antigen/MHC-TCR) and signal 2 (137-CD28) interactions.

The use of anti-CD40 antibodies to stimulate DC cells directly, would be expected to enhance a response to tumor antigens which are normally encountered outside of an inflammatory context or are presented by non-professional APCs (tumor cells). In these situations Th help and B7 costimulation signals are not provided.

The invention contemplates delivery of nucleic acids, polypeptides or fragments thereof for vaccination Delivery of polypeptides and fragments thereof can be accomplished according to standard vaccination protocols which are well known in the art. In another embodiment, the delivery of nucleic acid is accomplished by ex vivo methods, i.e. by removing a cell from a subject, genetically engineering the cell to express or include a CTSP polypeptide, and reintroducing the engineered cell into the subject. One example of such a procedure is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo nucleic acid delivery using vectors such as viruses and targeted liposomes also is contemplated according to the invention.

A virus vector for delivering a nucleic acid encoding a CTSP polypeptide is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., 1996, Virology 219:220-227; Eloit et al., 1997, J. Virol. 7:5375-5381; Chengalvala et al., 1997, Vaccine 15:335-339), a modified retrovirus (Townsend et al., 1997, J. Virol. 71:3365-3374), a nonreplicating retrovirus (Irwin et al., 1994, J. Virol. 68:5036-5044), a replication defective Semliki Forest virus (Zhao et al., 1995, Proc. Natl. Acad. Sci. U.S.A. 92:3009-3013), canarypox virus and highly attenuated vaccinia virus derivative (Paoletti, 1996, Proc. Natl. Acad. Sci. U.S.A. 93:11349-11353), non-replicative vaccinia virus (Moss, 1996, Proc. Natl. Acad. Sci. U.S.A. 93:11341-11348), replicative vaccinia virus (Moss, 1994, Dev. Biol. Stand. 82:55-63), Venzuelan equine encephalitis virus (Davis et al., 1996, J. Virol. 70:3781-3787), Sindbis virus (Pugachev et al., 1995, Virology 212:587-594), and Ty virus-like particle (Allsopp et al., 1996, Eur. J. Immunol. 26:1951-1959). A preferred virus vector is an adenovirus.

Preferably the foregoing nucleic acid delivery vectors: (1) contain exogenous genetic material that can be transcribed and translated in a mammalian cell and that can induce an immune response in a host, and (2) contain on a surface a ligand that selectively binds to a receptor on the surface of a target cell, such as a mammalian cell, and thereby gains entry to the target cell.

Various techniques may be employed for introducing nucleic acids of the invention into cells, depending on whether the nucleic acids are introduced in vitro or in vivo in a host. Such techniques include transfection of nucleic acid-CaPO$_4$ precipitates, transfection of nucleic acids associated with DEAE, transfection or infection with the foregoing viruses including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. Preferred antibodies include antibodies which selectively bind a CTSP polypeptide, alone or as a complex with a MHC molecule. Especially preferred are monoclonal antibodies. Where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

The invention further embraces methods for assessing prognosis of a subject diagnosed with cancer, such as cancers that include abnormal CTSP expression. As used herein, "assessing prognosis" means determining the likelihood of survival of a subject having or diagnosed with a disorder based on one or more biological and/or pathological parameters. Such prognostic application of the invention is particularly useful for assessing the prognosis for a subject previously diagnosed with a cancer, such as a carcinoma, preferably prostate cancer. In case of prostate cancer, for example, more than one in three patients that have undergone radical prostatectomy (RRP) show biochemical recurrence within ten years. Therefore, novel biomarkers that can be used to assess prognosis, for example by predicting the risk of biochemical recurrence in cancer patients are of clinical interest.

In general, "biochemical recurrence" is defined as an increase of a PSA level in a biological sample to >0.2 ng/mL (Roehl et al., 2004, J Urol. 172(3):910-4; Hull et al., 2002, J. Urol. 167(2 Pt 1):528-34; Amling et al., 2000 J Urol. 2000, 164(1):101-5; Grossfeld et al., 2003, J Urol. 169(1):157-63).

As shown in more detail below, the invention provides methods for assessing the prognosis of a subject with prostate cancer. The method involves obtaining a biological sample, e.g., plasma sample and a biopsy sample, from a subject and determining the presence of anti-CTSP-1 antibodies in the sample. The CTSP-1 polypeptides described herein, and fragments thereof that bind antibodies, are useful in the immunodetection of anti-CTSP-1 antibodies in the biological sample. The absence of anti-CTSP-1 antibodies in a biological sample is indicative of poor prognosis. In contrast, the presence of anti-CTSP-1 antibodies in a biological sample is indicative of good prognosis.

As used herein, "poor prognosis" means that there is a shortened period between the time a patient receives a treatment (e.g., RRP) and the time the patient presents biochemical recurrence of the disease. As used herein, "good prognosis" means that there is better outlook of survival, i.e., extended survival, (for example, after five years) among patients, as compared to control patients.

As will be clear to those skilled in the art, in some cases, the prognostic methods provided in the invention may be used in combination with other biomarkers of the disease. Accordingly, the methods described herein may be used, for example, in conjunction with other prostate cancer markers, such as prostate specific antigen (PSA), prostate specific membrane antigen (PSMA), prostatic acid phosphatase (PAP) or NY-ESO-1 in assessing prognosis. For example, the prognostic methods of the invention may further comprise determining the presence, absence or level of expression of NY-ESO-1 mRNA and/or NY-ESO-1 polypeptide in a biological sample using detection techniques well known in the art, such as PCR-based methods and hybridization-based methods for mRNA detection and immunological methods for detection of polypeptide. In such methods, the presence of NY-ESO-1 mRNA and/or NY-ESO-1 polypeptide in the biological sample is indicative of poor prognosis. Similarly, in some cases, the methods may comprise determining the presence or absence anti-NY-ESO-1 antibodies in a biological sample using immunological detection techniques well known in the art. In such methods, the presence of anti-NY-ESO-1 antibodies in the biological sample is indicative of poor prognosis.

According to a further aspect of the invention, compositions containing the nucleic acid molecules, proteins, and binding polypeptides of the invention are provided. The compositions contain any of the foregoing therapeutic agents in a carrier, optionally a pharmaceutically acceptable carrier. Thus, in a related aspect, the invention provides a method for forming a medicament that involves placing a therapeutically effective amount of the therapeutic agent in the pharmaceutically acceptable carrier to form one or more doses. The effectiveness of treatment or prevention methods of the invention can be determined using standard diagnostic methods described herein.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The therapeutics of the invention can be administered by any conventional route, including injection or by gradual infusion over time. The administration may, for example, be oral, intravenous, intratumoral, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694-1712). Those of skill in the art can readily determine the various parameters and conditions for producing antibody aerosols without undue experimentation. When using antisense preparations of the invention, slow intravenous administration is preferred.

The compositions of the invention are administered in effective amounts. An "effective amount" is that amount of a CTSP polypeptide composition that alone, or together with further doses, produces the desired response, e.g. increases an immune response to the CTSP polypeptide. In the case of treating a particular disease or condition characterized by expression of one or more CTSP polypeptides, such as cancer, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of CTSP polypeptide or nucleic acid encoding CTSP polypeptide for producing the desired response in a unit of weight or volume suitable for administration to a patient. The response can, for example, be measured by determining the immune response following administration of the CTSP polypeptide composition via a reporter system by measuring downstream effects such as gene expression, or by measuring the physiological effects of the CTSP polypeptide composition, such as regression of a tumor or decrease of disease symptoms. Other assays will be known to one of ordinary skill in the art and can be employed for measuring the level of the response.

The doses of CTSP polypeptide compositions (e.g., polypeptide, peptide, antibody, cell or nucleic acid) administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, for treatments for eliciting or increasing an immune response, doses of CTSP polypeptide are formulated and administered in doses between 1 ng and 1 mg, and preferably between 10 ng and 100 µg, according to any standard procedure in the art. Where nucleic acids encoding CTSP polypeptides or variants thereof are employed, doses of between 1 ng and 0.1 mg generally will be formulated and administered according to standard procedures. Other protocols for the administration of CTSP polypeptide compositions will be known to one of ordinary skill in the art, in which the dose amount, schedule of injections, sites of injections, mode of administration (e.g., intra-tumoral) and the like vary from the foregoing. Administration of CTSP polypeptide compositions to mammals other than humans, e.g. for testing purposes or veterinary therapeutic purposes, is carried out under substantially the same conditions as described above.

Where CTSP polypeptides are used for vaccination, modes of administration which effectively deliver the CTSP polypeptide and adjuvant, such that an immune response to the polypeptide is increased, can be used. For administration of a CTSP polypeptide in adjuvant, preferred methods include intradermal, intravenous, intramuscular and subcutaneous administration. Although these are preferred embodiments, the invention is not limited by the particular modes of administration disclosed herein. Standard references in the art (e.g., *Remington's Pharmaceutical Sciences*, 18th edition, 1990) provide modes of administration and formulations for delivery of immunogens with adjuvant or in a non-adjuvant carrier.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, and lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases, and the like.

The pharmaceutical agents of the invention may be administered alone, in combination with each other, and/or in combination with other anti-cancer drug therapies and/or treatments. These therapies and/or treatments may include, but are not limited to: surgical intervention, chemotherapy, radiotherapy, and adjuvant systemic therapies.

The invention also provides a pharmaceutical kit comprising one or more containers comprising one or more of the pharmaceutical compounds or agents of the invention. Additional materials may be included in any or all kits of the invention, and such materials may include, but are not limited to buffers, water, enzymes, tubes, control molecules, etc. The kit may also include instructions for the use of the one or more pharmaceutical compounds or agents of the invention for the treatment of cancer.

The invention includes kits for assaying the presence of CTSP polypeptides and/or antibodies that specifically bind to CTSP polypeptides. An example of such a kit may include the above-mentioned polypeptides bound to a substrate, for example a dipstick, which is dipped into a blood or body fluid sample of a subject. The surface of the substrate may then be processed using procedures well known to those of skill in the art, to assess whether specific binding occurred between the polypeptides and agents (e.g., antibodies) in the subject's sample. For example, procedures may include, but are not limited to, contact with a secondary antibody, or other method that indicates the presence of specific binding.

Another example of a kit may include an antibody or antigen-binding fragment thereof, that binds specifically to a CTSP polypeptide. The antibody, or antigen-binding fragment thereof, may be applied to a tissue or cell sample from a patient with cancer and the sample then processed to assess whether specific binding occurs between the antibody and an antigen or other component of the sample. In addition, the antibody, or antigen-binding fragment thereof, may be applied to a body fluid sample, such as serum, from a subject, either suspected of having cancer, diagnosed with cancer, or believed to be free of cancer. As will be understood by one of skill in the art, such binding assays may also be performed with a sample or object contacted with an antibody and/or CTSP polypeptide that is in solution, for example in a 96-well plate, or applied directly to a solid support (i.e., an object's surface).

Another example of a kit of the invention is a kit that provides components necessary to determine the level of expression of one or more CTSP nucleic acid molecules of the invention. Such components may include primers useful for amplification of one or more CTSP nucleic acid molecules and/or other chemicals for PCR amplification.

Another example of a kit of the invention is a kit that provides components necessary to determine the level of expression of one or more CTSP nucleic acid molecules of the invention using a method of hybridization.

The foregoing kits can include instructions or other printed material on how to use the various components of the kits for diagnostic purposes.

The invention further includes nucleic acid or protein microarrays (including antibody arrays) for the analysis of expression of CTSP polypeptides or nucleic acids encoding such antigens. In this aspect of the invention, standard techniques of microarray technology are utilized to assess expression of the CTSP polypeptides and/or identify biological constituents that bind such antigens. The constituents of biological samples include antibodies, lymphocytes (particularly T lymphocytes), and the like. Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezoelectric delivery. Probes may be covalently linked to the substrate. Nucleic acid probes preferably are linked using UV irradiation or heat.

Protein microarray technology, which is also known by other names including protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G.

MacBeath and S. L. Schreiber, "Printing Proteins as Microarrays for High-Throughput Function Determination," *Science* 289(5485):1760-1763, 2000.

Targets are peptides or proteins and may be natural or synthetic. The tissue may be obtained from a subject or may be grown in culture (e.g., from a cell line).

In some embodiments of the invention, one or more control peptide or protein molecules are attached to the substrate. Preferably, control peptide or protein molecules allow determination of factors such as peptide or protein quality and binding characteristics, reagent quality and effectiveness, hybridization success, and analysis thresholds and success.

Nucleic acid arrays, particularly arrays that bind CTSP nucleic acid sequences, also can be used for diagnostic applications, such as for identifying subjects that have a condition characterized by aberrant CTSP molecule expression, e.g., cancer. Nucleic acid microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast, Nature Genetics*, Vol. 21, January 1999, the entire contents of which is incorporated by reference herein.

According to the invention, probes are selected from the group of nucleic acids including, but not limited to: DNA, genomic DNA, cDNA, and oligonucleotides; and may be natural or synthetic. Oligonucleotide probes preferably are 15 to 40-mer oligonucleotides and DNA/cDNA probes preferably are 200 to 5000 bases in length, although other lengths may be used. Appropriate probe length may be determined by one of ordinary skill in the art by following art-known procedures. In one embodiment, preferred probes are sets of one or more of the CTSP nucleic acid molecules as described herein. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or oligonucleotide to the substrate. These agents or groups may include, for example, amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, nucleic acid probes are synthesized directly on the substrate in a predetermined grid pattern using methods such as light-directed chemical synthesis, photochemical deprotection, or delivery of nucleotide precursors to the substrate and subsequent probe production.

Targets for microarrays are nucleic acids selected from the group, including but not limited to: DNA, genomic DNA, cDNA, RNA, mRNA and may be natural or synthetic. In all embodiments, nucleic acid target molecules from human tissue are preferred. The tissue may be obtained from a subject or may be grown in culture (e.g., from a cell line).

In embodiments of the invention one or more control nucleic acid molecules are attached to the substrate. Preferably, control nucleic acid molecules allow determination of factors such as nucleic acid quality and binding characteristics, reagent quality and effectiveness, hybridization success, and analysis thresholds and success. Control nucleic acids may include but are not limited to expression products of genes such as housekeeping genes or fragments thereof.

EXAMPLES

Materials and Methods

Generation of CTSP-1 Full-Length Sequence cDNA sequencing: C21ORF99 sequence (SEQ ID NO: 12) was initially obtained by sequencing the full insert of cDNA clones from which the ESTs aligning to human chromosome 21 (HC21) were derived. cDNA clones (IMAGE 1461135 and 2909444) were obtained from Research Genetics (Invitrogen Corporation, Carlsbad Calif.) and were sequenced directly using the vector's primers.

RT-PCR: NYBR-1 and NYBR1.1 sequences were aligned to HC21 genomic sequence using the BLASTN program. Primers for RT-PCR were designed based on the HC21 genomic sequence in regions that showed similarity to NYBR-1 and NYBR-1.1 sequences and that were not covered by the C21ORF99 sequence. Primers were manually designed in order to avoid unspecific amplification of NYBR-1 or NYBR-1.1. RT-PCR reactions were carried out in a 25 µL reaction containing 10 of first strand testis cDNA, 1×Taq DNA polymerase buffer (Invitrogen, Carlsbad, Calif.), 0.11 mM dNTP, 2 mM $MgCl_2$, 1 unit Taq DNA polymerase (Invitrogen) and 6 µmol of the following primers CTSP-F15' CTGAAAGCTTGGTGGAAAG 3' (SEQ ID NO: 25) and CTSP-R15' GTTCCTTCTTCCAAAACTTC 3' (SEQ ID NO: 26) or CTSP-F2 5' AAGACTGAATGAGTGGCAG 3' (SEQ ID NO: 27) and CTSP-R25' CTGATTCAAATTACT-TCTTACAG 3' (SEQ ID NO: 28). Amplification conditions were: initial denaturation for 4 min at 94° C. followed by 40 cycles of 45 sec at 94° C., 45 sec at 58° C. and 1 min at 72° C. and a final extension of 10 min at 72° C. PCR products were analyzed on 8% silver-stained polyacrylamide gels and cloned using the TA cloning kit (Invitrogen). Individual colonies were sequenced using Dynamic ET terminator cycle sequencing (Amersham, Piscataway, N.J.) and an ABI3100 Prism sequencer. Sequences were aligned to HC21 sequence using BLASTN to confirm their specificity.

Rapid Amplification of cDNA Ends: 3' RACE was performed on normal testis poly(A)+ RNA using the Marathon cDNA Amplification Kit (Clontech, Mountain View, Calif.). Double-strand cDNA synthesis and adaptors ligation to the synthesized cDNAs were carried out according to the manufacturers' instructions. Amplification reactions were performed in a 25 µl reaction using 5 µl of cDNA, 0.2 mM dNTPs, 0.2 µM of CTSP-1 specific primer (SP-RACE 5' CCATGGCTCACACCTGTAATCTCATCAC 3'; SEQ ID NO: 29), 0.2 µM of the adaptor primers (ADPT 5' CGACGTGGACTATCCATGAACGCACG- CAGTCGGTAC(T)₁₃ 3'; SEQ ID NO: 30) and 1 unit of Advantage Taq DNA polymerase (Clontech). PCR conditions were: 1 min at 94° C. followed by 5 cycles of 5 sec at 94° C. and 4 min at 70° C., 5 cycles of 5 sec at 94° C. and 4 min at 68° C., and 25 cycles of 5 sec at 94° C., 30 sec at 65° C. with a final extension step of 4 min at 68° C. Nested-PCR was carried out in the same conditions using 1 µl of the first reaction product and the following primers: SP-RACE3N 5' GAAAAAGTTA-GAAGTGAAGCAACTTGAG 3' (SEQ ID NO: 31) and ADPTN 5' TCGAGCGGCCGCCCGGGCAGGTC-GACGTGGACTATCCATGAACGCA 3' (SEQ ID NO: 32).

PCR products were cloned using the TA cloning kit (Invitrogen) and sequenced as described above.

Computational Analysis

The CTSP-1 consensus sequence was obtained by assembling the C21ORF99 sequence, the two RT-PCR fragments and the 3' RACE fragments using Phred/Phrap/Consed (Gordon et al., 1998, Genome Res. 8:195-202). Repetitive elements along the CTSP-1 sequence were identified with RepeatMasker (A. F. A. Smit, R. Hubley & P. Green RepeatMasker at repeatmasker.org). CTSP family members and partial copies were identified by aligning CTSP-1 consensus sequence against the human genome assembly (May 2004) available at the UCSC Genome Browser using BLAT (Kent, 2002, Genome Res. 12:656-664). CTSP-2, 3 and 4 exon-intron structure and consensus sequences were predicted by pairwise alignments of the CTSP-1 consensus sequence with the human genome sequence using Sim4 (Florea et al., 1998, Genome Res. 8:967-974). Consensus sequences including all predicted exons were translated in all six reading frames and putative proteins were aligned using ClustalW (Higgins et al., 1996, Methods Enzymol. 266: 383-402). Protein motif searches were performed with PROSITE (Sigrist et al., 2002, Brief. Bioinform. 3: 265-274) and Pfam databases (Bateman et al., 2004, Nucleic Acids Res. 32: D138-D141).

Expression Analysis

Samples: Human tumor cell lines A1172 and T98G (glioblastoma); FaDu (squamous cell carcinoma); SW480 (colorectal adenocarcinoma); Skmel-28 and A2058 (malignant melanoma); DU145 and PC3 (prostate carcinoma); HeLa and CasKi (cervix adenocarcinoma); MDA-MB-231, MCF-7 and MDA-MB436 (breast ductal carcinoma); IM9 (B transformed lymphoblasts); HL60 and K562 (lymphocytes); Help G2 (hepatocarcinoma); H1155 and H358 (lung carcinoma); SCABER (urinary bladder carcinoma); SAOS-2 (osteosarcoma) were obtained from the American Type Culture Collection (ATCC) and maintained in appropriate medium as recommended by this organization (atcc.org). Tumor samples were collected from patients treated at Hospital A. C. Camargo. All samples were collected after explicit informed consent and with local ethical committee approval. Total RNA derived from 21 normal human tissues (testis, lung, prostate, small intestine, breast, brain, heart, uterus, bone marrow, placenta, colon, fetal brain, liver, fetal liver, thymus, salivary gland, spinal cord, kidney, spleen, skeletal muscle, and adrenal gland) was purchased from Clontech.

RNA extraction, cDNA synthesis and RT-PCR: Total RNA was extracted by the conventional CsCl-guanidine thiocyanate gradient method (MacDonald et al., 1987, *Methods Enzymol.* 152: 219-227). RNA samples were checked for integrity by agarose gel electrophoresis and 2 µg were used for cDNA synthesis. Reverse transcription was performed with DNA-free RNA using SUPERSCRIPT II Reverse Transcriptase (Invitrogen) and oligo dT. Primers used for expression analysis of CTSP-1, CTSP-2, CTSP3 and CTSP-4 were:

| | | |
|---|---|---|
| CT1F 5'GCTGTCCATTATGCTGTTAAC 3', | (SEQ ID NO: 33) |
| CT1R 5'TTTTGAGAATTTTTAGATATC 3', | (SEQ ID NO: 34) |
| CT2F 5'CCTGTGGTGCAGACATCG 3', | (SEQ ID NO: 35) |
| CT2R 5'ATTCCAAAAGTTGTTGATGAAC 3', | (SEQ ID NO: 36) |
| CT3F 5'CTGTCCATTATGCTGTTTATG 3', | (SEQ ID NO: 37) |
| CT3R 5'AATTTTTAGATATCTTTTGTTTG 3', | (SEQ ID NO: 38) |
| CT4F 5'TGCTGATCCAAATATTGTAGG 3' and | (SEQ ID NO: 39) |
| CT4R 5'CATTTAAACTTATCAACTGCAA 3'. | (SEQ ID NO: 40) |

PCR fragments were analyzed either on agarose gels followed by Southern blot analysis or on 8% silver-stained polyacrylamide gels. PCR fragments were cloned and sequenced as mentioned above to confirm their specificity.

5-Aza 2'Deoxycytidine Treatment

MCF-7 breast tumor cell line was treated with 30 µM of 5-Aza 2'deoxycytidine for 48 hours. After treatment the cells were harvested and used for RNA extraction and cDNA synthesis as described above. RT-PCR amplifications were carried out using the same CTSP-1 primers used for gene expression analysis. Amplification products were analyzed on 8% silver-stained polyacrylamide gels.

CTSP-1 Protein Detection

CTSP-1 recombinant protein: CTSP-1 longest ORF was amplified from normal testis cDNA using the following primers: CTSP1RecF 5' CGGGATCCATGAAGAAGACGA-CAATG 3' (SEQ ID NO: 41) and CTSP1RecR 5' CGGAAT-TCCTATTCGTCAGGTGTTCT 3' (SEQ ID NO: 42). The PCR product was digested with BamH I and EcoR I and cloned into the expression vector pET28a (Stratagene). After sequencing, the recombinant plasmid pET28a/CTSP-1 was transformed into *E. coli* BL-21 A494. After induction with 1 mM IPTG at 37° C. for 4 hours the CTSP-1 recombinant protein fused with a His-tag was purified by Ni²⁺ affinity chromatography using the NiNTA agarose resin (Invitrogen). The purified protein was analyzed by Western blot using an anti-His-tag monoclonal antibody (Amersham Biosciences) to confirm the purification specificity.

CTSP-1 polyclonal antibody: C57 mice (3-months old females) were immunized subcutaneously with 25 µg of CTSP-1 recombinant protein using Freund's Complete Adjuvant (Sigma, St. Louis, Mo.) and Mg(OH)₂ (EMS). Three weeks latter, the mice were boosted with a subcutaneous injection of 25 µg of the recombinant protein using Freund's Incomplete Adjuvant and a final boost was repeated 3 weeks later. Two weeks after the final boost, the sera were collected and analyzed by ELISA to determine antibody titer. A total of 250 ng/well of CTSP-1 recombinant in coating buffer (0.015M Sodium Carbonate and 0.03 µM Sodium Bicarbonate, pH 9.6) were adsorbed to ELISA plates (DYNEX Immulon® 2HB) overnight at 4° C. Plates were washed with PBS and blocked with 5% BSA in PBS-Tween (10 mM phosphate buffer, 140 mM NaCl, 0.05% Tween® 20, pH 7.4). The sera were diluted with PBS-Tween plus 0.1% BSA and incubated on the plates for 1 hour at room temperature. After washing with PBS-Tween, the bound antibodies were detected with peroxidase-conjugated anti-mouse IgG antibody (1:10000, Amersham Biosciences) using SIGMA FAST™ OPD tablets as substrate (Sigma).

Western blot: Normal testis tissue was homogenized in sample buffer (240 mM Tris pH 6.8, 0.8% SDS, 200 mM β-mercaptoethanol, 40% glycerol and 0.2% bromophenol blue). A total of 100 μg of the lysate was loaded on 12% SDS/PAGE gels and after fractionation transferred to Hybond-P PDVF membranes (Amersham Biosciences). After blocking with PBS solution containing 5% low-fat milk, the membranes were incubated with mice sera at a 1:10000 dilution for 1 hour at room temperature. Sera antibodies binding to CTSP-1 protein were detected by incubation with rabbit anti-mouse IgG HRP-conjugate (Amersham Biosciences) and visualized with ECLM Western Blotting Detection Reagents (Amersham Biosciences).

Immunohistochemistry

Normal testis and prostate specimens were fixed with buffered formalin and embedded in paraffin. Sections of 3 μm were placed on glass slides, heated at 60° C. for 20 minutes and then placed three times in a solution of xylene for 5 min, four times in 100% methanol for 30 sec and then washed in water rinses for 5 min. Slides were placed three times in 3% hydrogen peroxide for 5 min and washed in water rinses for 5 min prior to incubation for 24 hours in a humidified chamber with the primary antibody diluted 1:100. Slides were washed in PBS, incubated with biotinylated goat antirabbit IgG for 20 min and then with streptavidin-biotin peroxidase LSAB kit (Dako®, Carpinteria, USA) in a humidified chamber. The immunostaining was performed by incubating slides in diaminobenzidine (Dako) solution containing 1 μl of chromogen for 50 μl of buffer substrate during 5 min. After chromogen development, slides were washed, dehydrate with alcohol and xylene, and mounted with coverslips using a permanent mounting medium.

Antibody Response in Cancer Patients

Plasmas were obtained from patients with various tumor types (breast, colon, esophagus, lung, melanoma, prostate, stomach, thyroid and uterus) treated at the Hospital A.C. Camargo. All samples were collected after explicit informed consent and with local ethical committee approval. In addition, plasma samples from 50 healthy individuals were collected from blood donors at the Hospital A.C. Camargo Blood Center. Antibodies against CTSP-1 recombinant protein were detected by Western blot. Five hundred nanograms of purified CTSP-1 recombinant protein were fractioned on 12% SDS-PAGE gel electrophoresis and transferred to Hybond-P PVDF membranes. After blocking with PBS solution containing 5% low-fat milk, the membranes were incubated for 1 hour at room temperature with plasma from healthy individuals or cancer patients at a 1:25 dilution. Plasma antibodies binding to CTSP-1 protein were detected by incubation with goat anti-human IgG HRP-conjugate (Amersham Biosciences) and visualized with ECL™ Western Blotting Detection Reagents (Amersham Biosciences).

Example 1

Identification and Expression of CTSP-1

CTSP-1 Gene Structure and Alternative Polyadenylation Isoforms

Using the information generated by alignments between expressed sequence tags (ESTs) and the genomic sequence of the human chromosome 21 (HC21) (Reymond et al, 2002, *Genomics* 79: 824-832), a gene was identified and has been named C21ORF99 (AF427490; SEQ ID NO: 12), which was predominantly expressed in normal testis and showed high similarity to the amino-terminal region of the breast differentiation tumor antigen NYBR-1 and to its paralog NYBR-1.1 located at chromosomes 10 and 18, respectively (SEQ ID NO: 24). NYBR-1 cDNA was isolated by serological screening of a breast cancer library and expression analysis reveled a restricted mRNA expression in normal breast and testis tissues (Jager et al., 2001, *Cancer Res.* 61:2055-2061). NYBR-1 expression was also found in 21 of 25 breast tumors but in only 2 of 82 nonmammary tumors. NYBR-1.1 shares 54% amino acid identity with NYBR-1 and shows also a tissue restricted mRNA expression. However, unlike NYBR-1, NYBR-1.1 is expressed in normal brain in addition to breast and testis (Jager et al., 2001, *Cancer Res.* 61: 2055-2061).

Figure 1:
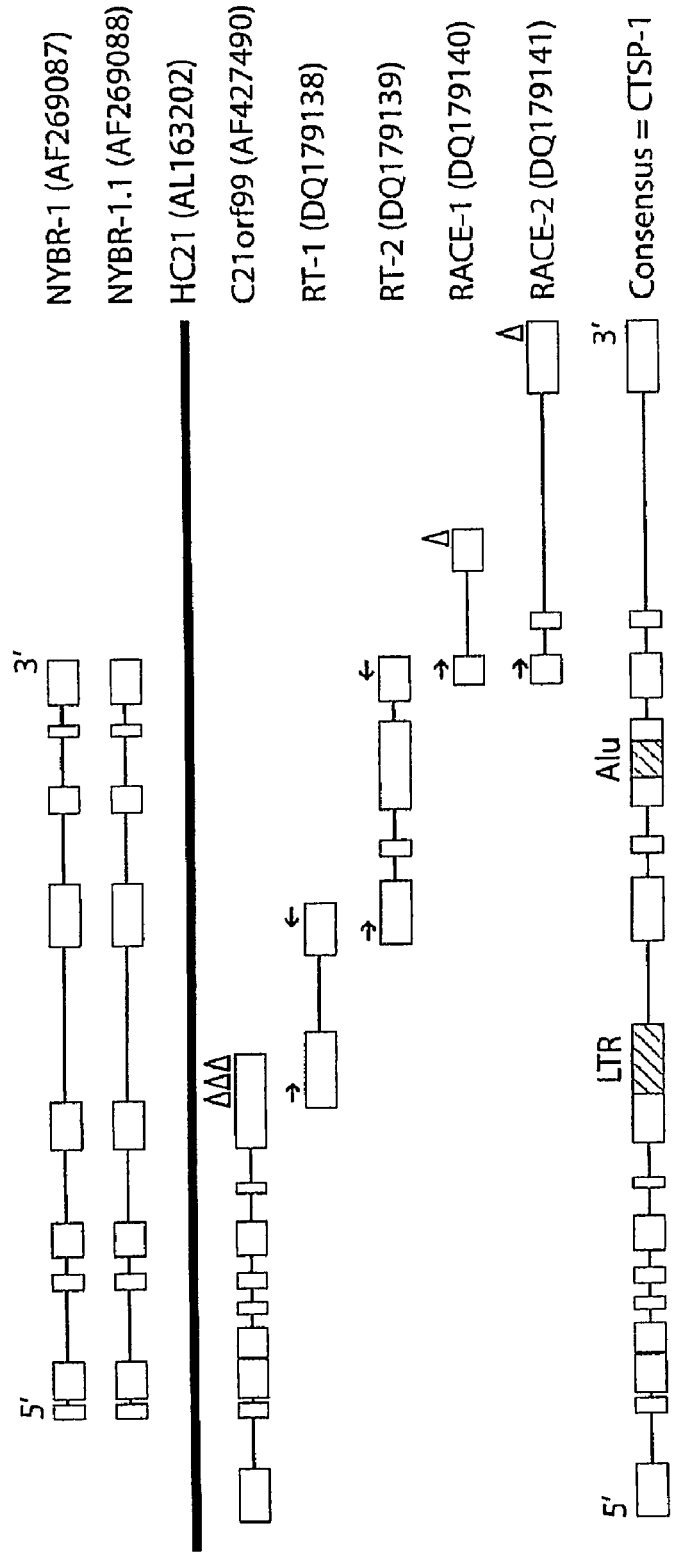
FIG. 1 provides a schematic representation of the strategies used in the generation of CTSP-1 consensus sequence.

C21ORF99 sequence was initially obtained by sequencing the full insert of cDNA clones from which the ESTs aligning to HC21 were derived (Reymond et al, 2002, *Genomics* 79: 824-832). However, based on the mapping of NYBR-1 and NYBR-1.1 to HC21 genomic sequence, it was suspected that the initial sequence obtained for C21ORF99 (derived from cDNA clones containing both polyA signal and tail) corresponded to a shorter alternative polyadenylation isoform (FIG. 1).

A combination of RT-PCR and 3' RACE experiments was used to extend the initial C21ORF99 sequence and to verify the existence of additional polyadenylation isoforms. First, two pairs of primers were designed which are specific for HC21 sequence in regions that showed similarity to NYBR-1 and NYBR-1.1. RT-PCR products obtained with these primers were cloned and sequenced and the original C21ORF99 sequence was extended as illustrated in FIG. 1.

Since the 3 end of NYBR-1 (from nt 3,199 to 4,458) and NYBR-1.1 (from nt 3,220 to 3,673) did not show significant similarity to the HC21 sequence, 3' RACE experiments were performed in order to generate a full-length sequence. Two distinct 3' RACE fragments corresponding to two additional alternative polyadenylation isoforms were amplified and sequenced (FIG. 1). All 3' ESTs available in public databases and corresponding to CTSP-1 are derived from the shortest isoform suggesting that it is the most abundantly expressed isoform (data not shown).

A consensus mRNA sequence of 3,915 bp (SEQ ID NO: 1), organized in 15 exons (SEQ ID NOs:43-57), was obtained by assembling the C21ORF99 sequence, the RT-PCR products and the longest 3' RACE fragment (FIG. 1) and was named CTSP-1. Careful analysis of this consensus sequence revealed the presence of two transcribed repetitive elements located within exons 9 (LTR repeat) and 12 (Alu repeat), which could not be found in the NYBR-1 and NYBR-1.1 sequences (FIG. 1).

Interestingly, since the polyadenylation sites associated with the shorter polyadenylation isoform are contained within the LTR repeat, it is tempting to speculate that the presence of this repetitive element within exon 9 is associated with the occurrence of alternative polyadenylation. It is well known that the insertion of retroelements in the human genome can affect gene expression by sequence disruption; however it has recently been shown that these sequences can also modulate gene expression by introducing intragenic polyadenylation signals (Roy-Engel et al., 2005, *Cytogenet. Genome Res.* 110: 365-371).

CTSP-4 Gene Family

The CTSP-1 sequence was aligned to the human genome sequence in order to identify additional family members. Three complete copies of highly similar genes were found on chromosomes 2 (CTSP-2, 98.0% identity), 14 (CTSP-3, 95.4% identity) and 18 (CTSP-4, 98.3% identity). The exon-intron structure seems to be highly conserved among these 4 members including the presence of both LTR and Alu repeats what suggests that they are products of recent gene-duplication events (FIG. 2). However, since the exon-intron structure for these loci were predicted based on the alignment of CTSP-1 to the genomic sequence, confirmation of this structure will depend on the generation of expressed sequences covering the full extension of all these genes. Recent duplication events have also been described for other CT antigens such as NY-ESO-1 and SSX, resulting in two or more identical copies with identical coding sequences (Aradhya et al., 2001, *Hum. Mol. Genet.* 10: 2557-2567; Gure et al., 2002, *Int. J. Cancer* 101: 448-453). ESTs and/or cDNA clones corresponding to all these family members can be found in public databases suggesting that all of them are transcribed. As for CTSP-1, all ESTs and cDNA clones corresponding to these family members represent the first 9 exons and are probably derived from the shorter polyadenylation isoform.

In addition to these complete copies, two partial copies were identified in tandem but in opposite directions on a region spanning ~318 kb on chromosome 9. These partial copies also contain the LTR and Alu repeats although, their exon-intron structure is slightly different and exons 6, 8, 14 and 15 are missing when compared to the complete copies (FIG. 2). Additionally, partial copies covering less than 58% of the CTSP-1 mRNA length and with a lower similarity (<95%) were found on chromosomes 22, 15 and 10 (FIG. 2) and they probably result from failed duplication events, as has also been observed for other CT-gene families, such as SSX. An extended analysis of the evolution and conservation of this gene family among primates will be presented elsewhere.

Expression Profile and Alternative Splicing Isoforms

Since one of the criteria for identifying CT antigen genes is their specific expression in tumors, but not in normal tissues except in testis, the mRNA expression pattern of CTSP-1 was determined by RT-PCR. Primers used in the expression analysis were manually designed to assure specific amplification and RT-PCR products were sequenced to confirm their specificity. A panel of cDNA samples was analyzed, including 21 samples derived from normal tissues, 21 derived from tumor cell lines and 169 derived from tumors of 10 different histological types.

CTSP-1 mRNA expression was first examined by RT-PCR in normal testis cDNA. A pair of primers located in exons 3 and 8 was used in the RT-PCR with 40 cycles of amplification. Three predominant fragments of 239,376 and 402 bp were obtained from testis cDNA (FIG. 3A) and the whole amplification product was cloned without prior gel purification. Clones with different insert sizes were selected for sequencing. Using this strategy we were able to identify at least 8 splicing variants in which exons 4, 5 and 7 were alternatively spliced as illustrated in FIG. 3B.

CTSP-1 mRNA expression was then analyzed in cDNA samples derived from 20 additional normal tissues and 21 tumor cell lines. In order to favor the detection of all splicing variants, RT-PCR products were transferred to nylon membranes and hybridized with a cDNA probe corresponding to exon 3, which is present in all splicing isoforms. Among the 21 normal tissues, CTSP-1 expression was restricted to testis and could also be detected in 47.6% (10/21) of all analyzed tumor cell lines (FIG. 4). Interestingly, although the expression of several alternative splicing isoforms was detected in normal testis cDNA a less complex pattern of alternative splicing could be visualized in cDNA derived from tumor cell lines (FIG. 3A). The shortest isoform, in which exons 4, 5 and 7 are skipped, appears to be the most abundant and frequently expressed isoform. Alternative splicing is an important regulatory mechanism that increases the diversity of proteins transcribed from a single gene. This process seems to be particularly important in testis development and spermatogenesis since a higher proportion of alternative splicing isoforms has been described in testis (Huang et al., 2005, *J. Androl.* 26:189-196).

The expression profile of CTSP-1 was then analyzed in 169 tumor samples derived from 10 different histological types of tumors. Positive expression was detected in 44.4% (75/169) of the samples (Table 1). The highest percentages of positive expression were observed in melanomas (59.0%) followed by prostate (58.0%) and lung (57%) tumors. As observed in the tumor cell lines, the shorter isoform was the most abundant and frequently expressed. This expression pattern is partially in agreement with the classification proposed by Scanlan et al. (Scanlan et al., 2004, *Cancer Immun.* 23(4):1. Review). In the proposed classification, melanomas and lung tumors were defined as tissues with higher CT expression tissues; breast, prostate and esophagus were classified as having moderate CT expression and stomach and colon as having low CT expression. Gliomas, thyroid and uterus tumors were not classified in this analysis due to the insufficient number of samples analyzed.

The expression pattern of the other 3 family members was also analyzed by RT-PCR. Primers used in the expression analysis were also manually designed to assure specific amplification and RT-PCR products were sequenced to confirm their specificity. Although the expression of the other CTSP-1 family members was also restricted among normal tissues, they were not frequently expressed in tumor cell lines and tumor samples. This fact has also been observed for other CT-antigen members of the MAGE and SSX families (Gure et al., 1997, *Int. J. Cancer* 72: 965-971; Lucas et al., 1999, *Cancer Res.* 59: 41004103; Pold et al., 1999, *Genomics* 59:161-167). A positive expression in normal testis was detected for CTSP-2 and 4, the first also being expressed in brain, fetal brain and spinal cord among the 21 normal tissues analyzed. Expression of CTSP-2 and CTSP-4 was not detected in any of the tumor cell lines, although CTSP-2 expression was detected in tumor samples at a lower frequency when compared to CTSP-1 (Table 1). CTSP-3 expression was not detected in any of the samples analyzed. Alternative splicing isoforms were also detected for CTSP-2 and CTSP-4.

TABLE 1

Frequency of mRNA expression of CTSP family members in tumor samples.

| Tumor | CTSP-1 | CTSP-2 | CTSP-4 |
| --- | --- | --- | --- |
| Breast | 9/25 (36.0%) | 1/6 (16.5%) | 0/6 (0.0%) |
| Colon | 7/18 (39.0%) | 0/14 (0.0%) | 0/14 (0.0%) |
| Esophagus | 2/5 (40.0%) | 2/4 (50.0%) | 0/4 (0.0%) |
| Glioblastoma | 6/13 (46.0%) | not done | not done |
| Lung | 8/14 (57.0%) | 2/11 (18.8%) | 0/11 (0.0%) |
| Melanoma | 10/17 (59.0%) | 1/9 (11.0%) | 0/9 (0.0%) |
| Prostate | 14/24 (58.0%) | 8/17 (47.0%) | 0/17 (0.0%) |
| Stomach | 4/9 (44.0%) | 1/3 (33.3%) | 0/3 (0.0%) |
| Thyroid | 7/24 (29.0%) | 0/6 (0.0%) | 0/6 (0.0%) |
| Uterus | 8/20 (40.0%) | 4/14 (28.5%) | 0/14 (0.0%) |
| Total | 75/169 (44.4%) | 19/84 (22.6%) | 0/84 (0.0%) |

An important element in the induction of CT antigen gene expression is promoter demethylation. It has been shown that demethylation of CT gene promoters with 5-Aza-2'deoxycytidine induces antigen expression in cells that do not normally produce them (Weber et al., 1994, *Cancer Res.* 54: 1766-1771; De Smet et al., 1999, *Mol. Cell. Biol.* 19: 7327-7335; Coral et al., 2002, *Clin. Cancer Res.* 8: 2690-2695). CTSP-1 gene expression was induced in the MCF-7 breast tumor cell line after treatment with 5-Aza-2'deoxycytidine, suggesting that methylation indeed plays an important role in CTSP-1 gene expression regulation (FIG. 7).

CTSP-1 Protein

The CTSP-1 sequence was translated to amino acid sequence and the presence of a stop codon was detected in exon 4, generating a 115 amino acid-long putative protein (SEQ ID NO: 13), which is much shorter than the NYBR-1 and NYBR-1.1 proteins. The presence of "premature" stop codons was also detected in all splicing variants, generating small "truncated" proteins of size ranging from 115 to 202 amino acids (FIG. 3B, SEQ ID NOs: 14-20). Interestingly, the longest open reading frame was predicted from the shortest splicing variant (variant h, without exons 4, 5 and 7), which is the most frequently expressed isoform in testis, tumor cell lines and tumor samples (FIG. 3).

All other members of the family seem to have "premature" stop codons as evaluated by aligning the CTSP-1 consensus sequence to the genomic sequence of chromosomes 2, 14 and 18. All exons predicted by the alignments were translated to protein. Since exon-intron structure for these loci were only predicted based on the alignment of CTSP-1 to the genomic sequence, confirmation of putative protein structures will depend on the generation of expressed sequences from these genes.

The existence of the CTSP-1 protein was confirmed by Western blot experiments using a polyclonal antibody generated against the CTSP-1 recombinant protein. As shown in FIG. 5A, a single band with the expected molecular mass (~22 kDa) was detected in total protein extracts from normal testis. No higher molecular mass bands were detected.

CTSP-1 protein was also detected by immunohistochemistry in normal testis and in a prostate tumor sample. CTSP-1 exhibited an intense staining in testis and the staining was restricted to germ cells. No reactivity in other structures of the testis was observed. Among the germ cells, an intense staining was detected in both the nucleus and the cytoplasm of the cells in later stages of differentiation such as spermatocytes and spermatids (FIG. 5B). It should be noted, however, that spermatogonias were mostly negative. A similar expression pattern has been observed for other non-X CT antigens (CT antigens mapped outside the chromosome X) (Simpson et al., 2005, *Nat Rev Cancer.* 5(8):615-25. Review). In the prostate tumor sample, staining was restricted to the tumor cells and the stroma, as well as the adjacent normal tissue were not stained by the anti-CTSP-1 antibody (FIG. 5B). Due to the high similarity observed among all family members, a possibility remains that the Western blot and immunohistochemistry results represent the accumulated expression of all or some of the CTSP members.

Structural analysis of NYBR-1 and NYBR-1.1 putative protein sequences revealed the presence of a bipartite nuclear signal and of a bZIP site (DNA-binding site followed by leucine zipper motif) suggesting that NYBR-1 and NYBR-1.1 are transcription factors (Jager et al., 2001, *Cancer Res.* 61: 2055-2061). NYBR-1 and NYBR-1.1 protein also present five tandem ankyrin repeats and tandem repetitive elements of unknown function, implying a role in protein-protein interactions. Motif analysis of the amino acid sequence corresponding to the longest open reading frame of CTSP-1 identified a bipartite nuclear localization signal (3-19 amino acids) and four tandem ankyrin repeats (14-47, 48-80, 81-103, 114-146 amino acids; these amino acid numbers correspond to the numbering of the longest protein, SEQ ID NO:20). However, the bZIP site and the tandem repetitive elements could not be found in the CTSP-1 sequence, suggesting that CTSP-1 is a nuclear protein that retained the ability to interact with other proteins but had lost the ability to interact with DNA. A similar protein structure is present in the other CTSP-1 family members.

Example 2

Humoral Response Against CTSP-1 in Cancer Patients

To evaluate the presence of antibodies against proteins from the CTSP-1 gene family in plasma from cancer patients, we established an immunobloting assay using recombinant his-tagged CTSP-1. Another his-tagged unrelated recombinant protein purified under the same conditions served as internal negative control.

A total of 141 plasma samples from cancer patients with different histological types of tumors were used in the immunoblotting assay (Table 2, FIG. 6). Among the 141 plasmas analyzed, 14 (10.0%) were reactive to the CTSP-1 recombinant protein. Plasma samples from 50 healthy donors were used as negative controls. Reactivity against CTSP-1 recombinant protein was only detected in one sample from this control group. Antibodies against CT antigens have been detected in patients with autoimmune disorders such as lupus erythematosus (McCurdy et al., 1998, *Mol. Genet. Metab.* 63: 3-13) and vitiligo (Rocha et al., 2000, *Int. J. Dermatol.* 39: 840-843) as well as in men subjected to vasectomy (Lea et al., 1997, *Fertil. Steril.* 67: 355-361). In addition, a possibility remains that a not yet diagnosed cancer patient within the healthy control group has been identified.

The highest percentages of antibody response against CTSP-1 were observed in patients with prostate (20.8%), thyroid (20.0%) and breast (16.6%) tumors (Table 2). With the exception of NY-ESO-1, humoral immune responses to CT antigens are relatively rare, occurring in less than 10% of the cancer patients (Stockert et al., 1998, *J. Exp. Med.* 187: 1349-1354). Serum antibody to NY-ESO-1 has been detected at a higher frequency in ovarian cancer, melanoma and breast cancer (Stockert et al., 1998, *J. Exp. Med.* 187: 1349-1354; Yakirevich et al., 2003, *Clin. Cancer Res.* 9: 6453-6460; Sugita et al., 2004, *Clin. Cancer Res.* 9: 6453-6460; Jager et al., 1999, *Int. J. Cancer* 84: 506-510).

TABLE 2

Frequency of anti-CTSP-1 antibodies in plasma samples from cancer patients.

| Tumor | Antibody Response |
|---|---|
| Breast | 3/18 (16.6%) |
| Colon | 0/20 (0.0%) |
| Esophagus | 0/4 (0.0%) |
| Lung | 1/13 (8.0%) |
| Melanoma | 1/22 (4.5%) |
| Prostate | 5/24 (20.8%) |
| Stomach | 1/8 (12.5%) |
| Thyroid | 2/10 (20.0%) |
| Uterus | 1/22 (4.5%) |
| Total | 14/141 (10.0%) |

For 121 out of the 141 patients included in this study, a correlation between CTSP-1 mRNA expression and the presence of a humoral immune response could be analyzed since both RNA and plasma samples were available (Table 3). A significant percentage (15.5%) of patients bearing CTSP-1 expressing tumors developed a humoral immune response against the protein. However, antibodies against CTSP-1 were also detected in 6.3% of patients with CTSP-1 negative tumors.

TABLE 3

Correlation between CTSP-1 mRNA expression and
CTSP-1 antibody response in cancer patients.

| Tumor | RT+/Ab+ | RT+/Ab− | RT−/Ab+ | RT−/Ab− | Total |
|---|---|---|---|---|---|
| Breast | 2 | 4 | 3 | 6 | 15 |
| Colon | 3 | 4 | 1 | 9 | 17 |
| Esophagus | 0 | 2 | 0 | 2 | 4 |
| Lung | 1 | 7 | 0 | 5 | 13 |
| Melanoma | 1 | 8 | 0 | 7 | 16 |
| Prostate | 7 | 4 | 1 | 9 | 21 |
| Stomach | 0 | 4 | 1 | 3 | 8 |
| Thyroid | 1 | 3 | 1 | 3 | 8 |
| Uterus | 1 | 6 | 0 | 12 | 19 |
| Total | 16 | 42 | 7 | 56 | 121 |

CTSP-1 mRNA expression was evaluated by RT-PCR (RT) and the presence of antibodies (Ab) was evaluated by Western blot.

A possible explanation for this apparent discrepancy would be the presence of an immune response against other CTSP family members. The expression of CTSP2 and CTSP-4 in these CTSP-1 negative tumors was then assayed by RT-PCR. Of the 7 CTSP-1 negative tumors analyzed, only one showed expression of CTSP-2 and none of them showed expression of CTSP-4. CTSP-2 and CTSP-4 mRNA expression were also analyzed in 84 of the 121 samples from which the corresponding plasma was available. The small percentage of positive expression of CTSP-2 (22.6%) and CTSP-4 (0%) in these samples suggests that the immune response observed in these patients is likely to be directed to CTSP-1. Alternative explanations for the discrepancy between CTSP-1 expression and antibody response would be the presence of tumor heterogeneity not represented in the small tissue fragment analyzed by RT-PCR; the presence of undetected metastases expressing CTSP-1 or the clearance of CTSP-1 positive tumor cells by the immune system.

Example 3

Antibodies Against the Cancer-Testis Antigen CTSP-1 as an Independent Prognostic Factor for Prostate Cancer Introduction Prostate cancer is a significant health problem that is common in men above the age of 50. It is the most commonly diagnosed malignancy, and the second leading cause of cancer-related death in men in the United States (Jemal et al., 2006, *CA Cancer J Clin.* 56(2):106-30). Radical prostatectomy (RRP) is the most common and effective treatment for clinically localized prostate cancer. However, approximately 35% of prostate cancer patients will have biochemical recurrence of the disease within 10 years after surgery. Subsequently, these patients will develop clinical relapse of the disease typically featuring bone metastases.

The ability to predict biochemical recurrence and cancer progression after RRP using clinical and pathological variables has been extensively investigated (Buhmeida et al., 2006, *Diagn Pathol.* 1:4; Blute et al., 2001, *J. Urol.* 165(1):119-25; Stamey et al., 1999, *JAMA.* 281(15):1395-400; Quinn et al., 2005, *Eur J Cancer* 41(6):858-87. Review). Recurrence of prostate cancer has been associated with multiple factors including preoperative PSA level and velocity, clinical stage, Gleason score, level of extracapsular extension, seminal vesicle invasion, pelvic lymph node status and surgical margin status (Buhmeida et al., 2006, *Diagn Pathol.* 1:4; Blute et al., 2001, *J Urol.* 165(1):119-25; Stamey et al., 1999, *JAMA.* 281(15):1395-400; Quinn et al., 2005, *Eur J Cancer* 41(6):858-87. Review). However, due to the significant clinical heterogeneity of the disease, these factors are far from accurate and the identification of novel biomarkers that are able to identify patients that are at high risk for cancer progression is thus clearly needed (Harding et al., 1998-1999, *Cancer Metastasis Rev.* 17(4):429-37. Review; Chin et al., 2004, *Clin Prostate Cancer.* 3(3):157-64. Review; Zimmerman et al., 2003, *Clin Prostate Cancer.* 2(3):160-6. Review).

Radiation therapy and surgical resection can be curative in localized disease (Roehl et al., 2004, *J Urol.* 172(3):910-4; Hull et al., 2002, *J Urol.* 167(2 Pt 1):528-34; Stephenson et al., 2004, *JAMA.* 291(11):1325-32). However, at present there is no cure for metastatic prostate cancer and the development of molecularly target therapies for prostate cancer is of considerable interest. Tumor vaccines represent one type of molecularly target therapy being investigated for prostate cancer (Harada et al., 2003, *Int J Clin Oncol.* 8(4): 193-9. Review; Webster et al., 2005, *J Clin Oncol.* 23(32):8262-9. Review; Fong et al., 2006, *Curr Urol Rep.* 7(3):239-46. Review; Madan et al., 2006, *Expert Rev Vaccines.* 5(2):199-209. Review). Preclinical and early clinical data suggest that tumor vaccine therapies are feasible and safe and provide clinical benefits to patients with prostate cancer.

Cancer/Testis (CT) antigens are proteins expressed in normal gametogenic tissues and in different types of tumors (Scanlan et al., 2002, *Immunol Rev.* 188:22-32. Review; Scanlan et al., 2004, *Cancer Immun.* 4:1. Review; Simpson et al., 2005, *Nat Rev Cancer.* 5(8):615-25. Review; Zendman et al., 2003, *J Cell Physiol.* 194(3):272-88. Review). Most CT antigens are highly immunogenic, eliciting both humoral and cellular immune response in cancer patients. Due to their restricted expression pattern and immunogenicity, CT antigens are considered to be ideal targets for cancer immunotherapy (Scanlan et al., 2002, *Immunol Rev.* 188:22-32. Review; Bodey, 2002, *Expert Opin Biol Ther.* 2(6):577-84. Review).

As described above, the novel CT antigen, CTSP-1, is exclusively expressed in normal testis and is aberrantly expressed in 47% of tumor cell lines and in 44% of tumors from different histological types (Parmigiani et al., 2006, *Proc. Natl. Acad. Sci. USA.* 103(48):18066-71). CTSP-1 is part of a highly conserved gene family, and antibodies against members of this gene family were detected in 10% of plasma samples from patients with a wide spectrum of tumors. CTSP-1 was found to be aberrantly expressed in 58% of prostate tumors and capable of eliciting a humoral immune response in approximately 20% of prostate cancer patients (Parmigiani et al., 2006, *Proc. Natl. Acad. Sci. U.S.A.* 103 (48):18066-71).

Here we confirm that antibodies against CTSP-1 are frequently found in prostate cancer patients, suggesting that this antigen might be a promising candidate for prostate cancer immunotherapy. Moreover, patients presenting antibodies against CTSP-1 had a longer biochemical recurrence-free survival, indicating that the presence of a spontaneous humoral immune response against CTSP-1 could be used as a novel biomarker for biochemical recurrence in prostate cancer patients with clinically localized disease.

Patients and Methods

Patients and surgical specimens The study included 147 consecutive localized prostate cancer patients who underwent radical retropubic prostatectomy with simultaneous bilateral pelvic lymphadenectomy at the Urology Division of the Pelvic Surgery Department of the Hospital do Cancer, São Paulo, Brazil, between November 1998 and July 2005. All cases had clinically localized disease suspected by elevated serum PSA levels or palpable nodules on a digital rectal examination, and were diagnosed by transrectal ultrasound-guided needle biopsy of the prostate. Serum PSA levels were measured with Elecsys chemiluminescent assay on a Elecsys analyser 1010, Roche®. Patients with PSA levels higher than 15 ng/mL or Gleason score higher than 7 were submitted to bone scan and patients with positive preoperative imaging were excluded from this analysis. Patients with a second non-prostate primary tumour, or that were submitted to radiotherapy before the surgery, were also excluded from this study. Twenty-seven patients received neoadjuvant androgen suppression.

After RRP, patients were followed up with serum PSA tests every 3 months during the first year, twice a year between the second and the fifth year and then annually thereafter. Patients with an increase in PSA levels after RRP were submitted to rectal digital examination, pelvic and abdominal computerized tomography and transrectal ultrasound-guided needle biopsy to confirm local recurrence and bone scan to detect distant metastasis.

Surgical specimens were staged according to the 1997 American Joint Committee on Cancer System and graded using the Gleason system. Specimens were also evaluated for surgical margin status, perineural, angiolymphatic, extracapsular and seminal vesicle invasion as well as for the presence of metastasis in all removed lymph nodes. Clinicopathological data and follow-up information were obtained retrospectively from patient's medical records. Patients that did not return to the institution for their regular follow-up were contacted by telephone to update their health status and most recent PSA test. The mean follow up time of this cohort was 52.1 months (range 2.9 to 96.2). Biochemical recurrence was defined as a serum PSA level>0.2 ng/ml on two consecutive PSA tests after RRP.

Immunobloting analysis Plasma samples were collected after explicit informed consent and the study was reviewed and approved by the institution's ethical committee. Patient identifiers were removed and samples were coded to protect confidentiality. Serum antibody responses against the recombinant CTSP-1 protein were tested by standard Western blot analysis as previously described (Parmigiani et al., 2006, Proc. Natl. Acad. Sci. U.S.A. 103(48):18066-71). Briefly, purified CTSP-1 recombinant protein was fractioned on SDS/PAGE gel electrophoresis and transferred to Hybond-P PVDF membranes. After blocking with PBS solution containing 5% low-fat milk, the membranes were incubated for 1 h at room temperature with plasma from prostate cancer patients. Plasma antibodies binding to CTSP-1 protein were detected by incubation with goat anti-human IgG HRP-conjugate (Amersham Biosciences) and visualized with ECLM Western Blotting Detection Reagents (Amersham Biosciences).

Statistical Analysis Fisher exact test or Chi-square tests were used to evaluate the association between serum antibody response against CTSP-1 and clinicopathological parameters, for continuous variables Mann-Whitney U was used to compare the values between the two groups considering CTSP-1. The preoperative PSA level was considered as a continuous variable, the pathological Gleason score was divided in two categorical variables (4 to 6 and 7 to 8) and tumor volume was divided in 4 categorical variables (1 to 10, 11-30, 31-50 and 51-100). Biochemical recurrence free survival (from the date of the RRP until the date of the first PSA measurement>0.2 ng/ml or to the date of the last follow up) and clinical recurrence free survival (from the date of the RRP until the date of detection of local or distant disease or until the date of the last follow up) curves were calculated with Kaplan-Meier method. Log-rank test was used to assess statistical differences between the curves. Multivariate analysis was carried out using Cox proportional hazard regression model. All variables presenting p-value<0.20 on the univariate analysis were selected for building a multiple model (stepwise forward method), since this level of significance eliminates many insignificant variables and ensures that all potential explanatory variables are included. For all tests, type 1 error (alpha) was established as 0.05 and results were considered statistically significant when p<0.05. All of the statistical analyses were performed using SPSS Software 10.0 (SPSS Inc., Chicago, Ill.).

Humoral response against CTSP-1 and pathological parameters. The pathological parameters of the 147 patients analyzed in this study are summarized in Table 4 below. The mean age of the patients at diagnosis was 61.6 years (range 41-75) and the mean preoperative PSA level was 10.8 ng/ml (range 1.2 to 44). Humoral response against CTSP-1 was detected in 37 (25.2%) patients by Western blot.

TABLE 4

Pathological characteristics of the prostate cancer patients.

| Characteristic | Category | No. (%) |
|---|---|---|
| Pathologic T staging | T2a | 16 (10.9) |
| | T2b | 82 (55.8) |
| | T3a | 27 (18.4) |
| | T3b | 14 (9.5) |
| | T4 | 8 (5.4) |
| Pathologic N staging | N0 | 145 (98.6) |
| | N1 | 2 (1.4) |
| Gleason score | 4-6 | 98 (66.7) |
| | 7-8 | 49 (33.4) |
| Tumour volume (%) | 1-10 | 54 (38.8) |
| | 11-30 | 59 (42.4) |
| | 31-50 | 17 (12.2) |
| | 51-100 | 9 (6.5) |
| Perineural invasion | No | 40 (27.4) |
| | Yes | 106 (72.6) |
| Angiolymphatic invasion | No | 22 (15.1) |
| | Yes | 124 (84.9) |
| Extracapsular invasion | No | 70 (47.6) |
| | Focal | 65 (44.2) |
| | Diffuse | 12 (8.2) |
| Margins | Negative | 115 (78.2) |
| | Positive | 32 (21.8) |
| Siminal vesical invasion | No | 134 (91.2) |
| | Yes | 13 (8.8) |

The distribution of pathological parameters according to the presence of humoral response against CTSP-1 is listed in Table 5 below. No statistically significant association was observed between the presence of antibodies against CTSP-1 and the following parameters: preoperative PSA level (p=0.173), tumor stage (p=0.126), lymph node status (p=0.409), Gleason score (p=0.139), tumor volume (p=0.478), perineural invasion (p=0.427), angiolymphatic invasion (p=0.427), extracapsular invasion (p=0.319), seminal vesicle invasion (p=0.128) and surgical margins (p=0.344).

TABLE 5

Patient's distribution according to the existence of humoral response against CTSP-1.

| | Humoral Response | | |
|---|---|---|---|
| Characteristic | No | Yes | p-value |
| Pathologic T staging | | | |
| T2a | 13 (81.3%) | 3 (18.7%) | 0.126 |
| T2b | 60 (73.2%) | 22 (26.8%) | |
| T3a | 17 (63.0%) | 10 (37.0%) | |
| T3b | 14 (100.0%) | 0 (0.0%) | |
| T4 | 6 (75.0%) | 2 (25.0%) | |

TABLE 5-continued

Patient's distribution according to the existence of humoral response against CTSP-1.

| Characteristic | Humoral Response | | p-value |
|---|---|---|---|
| | No | Yes | |
| Pathologic N staging | | | |
| N0 | 108 (74.5%) | 37 (25.5%) | 0.409 |
| N1 | 2 (100.0%) | 0 (0.0%) | |
| Gleason score | | | |
| 4-6 | 77 (78.6%) | 21 (21.4%) | 0.139 |
| 7-8 | 33 (67.3%) | 16 32.7%) | |
| Tumour volume (%) | | | |
| 1-10 | 40 (74.1%) | 14 (25.9%) | 0.478 |
| 11-30 | 41 (69.5%) | 18 (30.5%) | |
| 31-50 | 15 (88.2%) | 2 (11.8%) | |
| 51-100 | 7 (77.8%) | 2 (22.2%) | |
| Perineural invation | | | |
| No | 28 (70.0%) | 12 (30.0%) | 0.427 |
| Yes | 81 (76.4%) | 25 (23.6%) | |
| Angiolymphatic invasion | | | |
| No | 28 (70.0%) | 12 (30.0%) | 0.427 |
| Yes | 81 (76.4%) | 25 (23.6%) | |
| Extracapsular invasion | | | |
| No | 55 (78.6%) | 15 (12.4%) | 0.319 |
| Focal | 48 (73.8%) | 17 (26.2%) | |
| Diffuse | 7 (58.3%) | 5 (41.7%) | |
| Margins | | | |
| Negative | 84 (73.0%) | 31 (27.0%) | 0.344 |
| Positive | 26 (81.3%) | 6 (18.7%) | |
| Seminal vesicle invasion | | | |
| No | 98 (73.1%) | 36 (26.9%) | 0.128 |
| Yes | 12 (92.3%) | 1 (7.7%) | |

Humoral response against CTSP-1 and biochemical recurrence. Kaplan-Meier analysis was then used to estimate the relationship between the presence of humoral response against CTSP-1 and the risk of biochemical recurrence of the disease. The probability of 5-year biochemical recurrence-free survival among all of the 147 patients evaluated was 61.8%. Patients that did not present antibodies against CTSP-1 had a shorter biochemical recurrence-free interval than did those presenting anti-CTSP-1 antibodies, although the difference between the groups was not statistically significant (57.2 versus 75.6%, p=0.075, FIG. 8A). Interestingly, none of the patients presenting antibodies against CTSP-1 developed clinical symptoms of the disease (FIG. 8B). Five-year biochemical recurrence-free survival in our patient population was also influenced by the following parameters (Table 6): preoperative PSA level (p<0.001), tumor stage (p<0.001), Gleason score (p=0.016), tumor volume (p<0.001), seminal vesicle invasion (p<0.001) and surgical margins (p<0.001).

TABLE 6

Univariate analysis of biochemical-recurrence-free survival.

| Characteristic | Category | 5-year BRFS (%) | p-value |
|---|---|---|---|
| Pathologic T staging | T2a | 0 | 0.001 |
| | T2b | 66.6 | |
| | T3a | 80.3 | |
| | T3b | 23.6 | |
| | T4 | 18.8 | |

TABLE 6-continued

Univariate analysis of biochemical-recurrence-free survival.

| Characteristic | Category | 5-year BRFS (%) | p-value |
|---|---|---|---|
| Pathologic N staging | N0 | 62.0 | 0.341 |
| | N1 | 50.0 | |
| Gleason score | 4-6 | 69.1 | 0.016 |
| | 7-8 | 49.9 | |
| Tumour volume (%) | 1-10 | 73.0 | <0.001 |
| | 11-30 | 67.7 | |
| | 31-50 | 61.5 | |
| | 51-100 | 22.2 | |
| Perineural invasion | No | 67.3 | 0.134 |
| | Yes | 58.9 | |
| Angiolymphatic invasion | No | 64.0 | 0.093 |
| | Yes | 48.5 | |
| Extracapsular invasion | No | 73.1 | 0.161 |
| | Focal | 54.1 | |
| | Diffuse | 41.6 | |
| Margins | Negative | 68.4 | <0.001 |
| | Positive | 40.5 | |
| Seminal vesicle invasion | No | 66.9 | <0.001 |
| | Yes | 40.5 | |
| Preoperative PSA | Continuous | | <0.001 |
| Antibody | Positive | 75.6 | 0.075 |
| | Negative | 57.2 | |

Humoral response against CTSP-1 as an independent prognostic marker for biochemical recurrence. A multivariate analysis was then performed in order to determine whether the presence of a humoral immune response against CTSP-1 is an independent factor in predicting biochemical recurrence of the disease. The preoperative PSA level, the Gleason score and the presence of antibodies against CTSP-1 were considered as independent prognostic factors for biochemical recurrence free survival (Table 7). Patients presenting antibodies against CTSP-1 had a lower risk for biochemical recurrence than patients without anti-CTSP-1 (HR 0.36, $_{95\%}$CI 0.2-0.8, p=0.013).

TABLE 7

Multivariate analysis of biochemical-recurrence-free survival.

| Variables | Category | HR | 95% CI | p-value |
|---|---|---|---|---|
| Preoperative PSA | Continuous | 1.09 | 1.06-1.13 | <0.001 |
| Antibody | Negative | 1.0 | Ref. | 0.013 |
| | Positive | 0.36 | 0.2-0.8 | |
| Gleason score | 4-6 | 1.0 | Ref. | 0.018 |
| | 7-8 | 2.0 | 1.3-3.7 | |

Discussion

It is widely held that the discovery of novel biomarkers that are capable of predicting the risk of biochemical recurrence and/or that could be used as targets for alternative anti-cancer therapy, such as immunotherapy, are clearly needed for prostate cancer.

Among various types of epithelial cancers, prostate cancer appears to be one of the best targets for specific immunotherapy. It is generally recognized that the human immune system is capable of mounting a significant immune response against the prostate tissue that can be both unremitting and destructive in nature (Nelson et al., 2004, *J Urol.* 172(5 Pt 2):S6-11; discussion S11-2. Review). Relevant to this, inverse relationships between the rates of disease recurrence and the number of infiltrating T lymphocytes within prostate tumors, as well as, advanced tumor grades and the number of macrophages within prostate tissue, imply that patient cell-mediated immunity may actively suppress prostate tumor progression (Vesalainen et al., 1994, *Eur J Cancer.* 30A(12):

1797-803; Shimura et al., 2000, *Cancer Res.* 60(20):5857-61). Moreover, it has been demonstrated that immunity against normal and cancerous prostate tissue can be induced by a variety of manipulations of the immune system, including peptide, DNA, virus-based, dendritic cell and genetically-modified tumor vaccines (Harada et al., 2003, *Int J Clin Oncol.* 8(4):193-9. Review; Webster et al., 2005, *J Clin Oncol.* 23(32):8262-9. Review; Fong et al., 2006, *Curr Urol Rep.* 7(3):239-46. Review; Madan et al., 2006, *Expert Rev Vaccines.* 5(2):199-209. Review). In addition, the generally slow progression of prostate cancer provides relatively long interval of time for the induction and potentiation of T-cell mediated anti-tumoral immunity during immunotherapeutic treatment. Finally, given that prostate is a relatively dispensable organ, often removed by surgery as part of prostate cancer treatment, immune response to prostate-related antigens can be considered as tumor specific in patients with recurrent metastases.

The results of several clinical vaccine trials suggest a clinical benefit to patients with prostate cancer and phase III trials are current underway in patients with androgen-independent prostate cancer. The antigens included in these studies are mainly proteins with known prostate-restricted expression (e.g., PSA, PSMA, PAP) and most of them are not natural targets of an immune response in patients with cancer (Harada et al., 2003, *Int J Clin Oncol.* 8(4):193-9. Review; Webster et al., 2005, *J Clin Oncol.* 23(32):8262-9. Review; Fong et al., 2006, *Curr Urol Rep.* 7(3):239-46. Review; Madan et al., 2006, *Expert Rev Vaccines.* 5(2):199-209. Review). Identifying immunologically recognized proteins in patients with prostate cancer could thus lead to the development of other potential vaccine target antigens.

CT antigens represent a novel and expanding family of proteins which are expressed in normal gametogenic tissues and in different types of tumors and are also immunogenic in cancer patients (Scanlan et al., 2002, *Immunol Rev.* 188:22-32. Review; Scanlan et al., 2004, *Cancer Immun.* 4:1. Review; Simpson et al., 2005, *Nat Rev Cancer.* 5(8):615-25. Review; Zendman et al., 2003, *J Cell Physiol.* 194(3):272-88. Review). To date, 89 individual CT antigen genes have been described, which are organized into 44 families (Simpson et al., 2005, *Nat Rev Cancer.* 5(8):615-25. Review). It is believed that these antigens escape normal immune response, due to their restricted expression in MRC class I-negative germ cells (Scanlan et al., 2002, *Immunol Rev.* 188:22-32. Review; Bodey, 2002, *Expert Opin Biol Ther.* 2(6):577-84. Review). Thus, CT antigens have been considered to be ideal targets for cancer immunotherapy as they may serve essentially as tumor-restricted antigens that are at a lower risk for preexisting immune tolerance and for creating potential autoimmune reactions in normal tissues (Scanlan et al., 2002, *Immunol Rev.* 188:22-32. Review; Bodey, 2002, *Expert Opin Biol Ther.* 2(6):577-84. Review).

Several members of the CT antigen family are expressed in prostate tumors including PAGE-4, NY-ESO-1, LAGE-1, XAGE-1 and members of the MAGE-A family. However, little is known about their ability to induce humoral and cellular immune responses in prostate cancer patients and their utility as target for prostate cancer immunotherapy remains poorly unexplored (Prikler et al., 2004, *Aktuelle Urol.* 35(4):326-30; Nakada et al., 2003, *Cancer Immun.* 3:10; Lethe et al. 1998, *Int J Cancer.* 76(6):903-8; Egland et al., 2002, *Mol Cancer Ther.* 1(7):441-50; Kufer et al., 2002, *Cancer Res.* 62(1):251-61).

As shown above, a novel CT antigen named CTSP-1, is exclusively expressed in normal testis among normal tissues and is aberrantly expressed in 58% of prostate tumors. CTSP-1 is part of a highly conserved gene family, and antibodies against members of this gene family were detected in approximately 20% of prostate cancer patients (Parmigiani et al., 2006, *Proc. Natl. Acad. Sci. U.S.A.* 103(48):18066-71). In this study, a natural humoral immune response against CTSP-1 was detected in 25.2% of the patients with clinically localized prostate cancer. Since the antibodies detected against CTSP-1 are of the IgG class, the activation of CD4+ T-cell response to CTSP-1 could also be present in these patients. Further experiments are ongoing to test if the CTSP-1 protein is able to induce CD4+ and CD8+ T-cell responses in cancer patients. These results confirm our initial observations and suggest that CTSP-1 might be a promising candidate for prostate cancer immunotherapy.

Here, we demonstrated that the presence of antibodies against CTSP-1 is an independent prognostic predictor of biochemical recurrence after RRP. Reports on the association of expression and the presence of immune response against CT antigens with clinical events and prognosis are limited to a few studies involving a limited number of patients. Most of these studies are on the highly immunogenic CT antigen NY-ESO-1. NY-ESO-1 mRNA and/or protein expression was predominantly detected in higher grade and advanced breast and esophageal tumors, transitional cell bladder carcinomas and medullary thyroid carcinomas, however no association with disease outcome was established. Similarly, immunological assessment of patients with NY-ESO-1 positive tumors revealed no association with clinicopathological parameters and disease outcome (Sharma et al., 2003, *Cancer Immun.* 3:19; Sugita et al., 2004, *Cancer Res.* 64(6):2199-204; Maio et al., 2003, *J Clin Endocrinol Metab.* 88(2):748-54; Akcakanat et al., 2004, *Cancer Chemother Pharmacol.* 54(1):95-100). In prostate cancer, NY-ESO-1 protein was predominantly expressed in hormone-refractory prostate tumors when compared to localized tumors and anti-NY-ESO-1 antibodies were also more frequently found in the serum of patients with advanced disease. Spontaneous serological response against NY-ESO-1 was associated with poor survival (Fossa et al., 2004, *Prostate.* 59(4):440-7). Together with our own data, these results suggests that the presence of a natural immune response against CT antigens could be used as prognostic factors, specially in prostate cancer, and deserves further evaluation.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

The invention claimed is:

1. An isolated polypeptide, comprising the amino acid sequence selected from the group consisting of SEQ ID NO:13, SEQ ID NO:15, and SEQ ID NO:20.

2. The isolated polypeptide of claim 1, wherein the polypeptide has the amino acid sequence set forth as SEQ ID NO:20.

3. A composition, comprising the isolated polypeptide of claim 1 and a carrier.

4. The composition of claim 3, further comprising an adjuvant.

5. A composition, comprising the isolated polypeptide of claim 1, which is attached to a solid substrate.

6. A composition, comprising the isolated polypeptide of claim 1 and at least one additional cancer-testis antigen polypeptide.

7. The composition of claim 6, wherein the at least one additional cancer-testis antigen is a NY-ESO-1, MAGE or SSX polypeptide.

8. The composition of claim 7, further comprising a carrier.

9. The composition of claim 8, further comprising an adjuvant.

10. A method for stimulating an immune response in a subject, comprising:
    administering to the subject a composition that comprises the polypeptide of claim 1 to stimulate an immune response against the polypeptide.

11. The method of claim 10, wherein the composition further comprises an adjuvant or a cytokine.

* * * * *